(12) United States Patent
Cheng et al.

(10) Patent No.: US 7,534,455 B2
(45) Date of Patent: *May 19, 2009

(54) HERBAL COMPOSITION PHY906 AND ITS USE IN CHEMOTHERAPY

(75) Inventors: Yung-Chi Cheng, Woodbridge, CT (US); Shwu-Huey Liu, Madison, CT (US)

(73) Assignee: Yale University, New Haven, CT (US)

( * ) Notice: Subject to any disclaimer, the term of this patent is extended or adjusted under 35 U.S.C. 154(b) by 376 days.

This patent is subject to a terminal disclaimer.

(21) Appl. No.: 11/100,433

(22) Filed: Apr. 7, 2005

(65) Prior Publication Data

US 2005/0196473 A1    Sep. 8, 2005

Related U.S. Application Data

(63) Continuation-in-part of application No. 10/220,876, filed as application No. PCT/US01/07353 on Mar. 8, 2001, now Pat. No. 7,025,993, which is a continuation-in-part of application No. 09/522,055, filed on Mar. 9, 2000, now abandoned.

(60) Provisional application No. 60/625,943, filed on Nov. 9, 2004.

(51) Int. Cl.
*A61K 36/484* (2006.01)
*A61K 36/725* (2006.01)
*A61K 36/539* (2006.01)
*A61K 36/65* (2006.01)

(52) U.S. Cl. .................................................. 424/725

(58) Field of Classification Search ........................ None
See application file for complete search history.

(56) References Cited

U.S. PATENT DOCUMENTS

| 4,618,495 | A  | * | 10/1986 | Okuda et al. | 424/728 |
|---|---|---|---|---|---|
| 5,595,756 | A  | * | 1/1997 | Bally et al. | 424/450 |
| 5,665,393 | A  | * | 9/1997 | Chen et al. | 424/489 |
| 6,048,847 | A  | * | 4/2000 | Ramadoss et al. | 514/169 |
| 6,630,176 | B2 | * | 10/2003 | Li et al. | 424/728 |
| 2003/0180395 | A1 | * | 9/2003 | Bueter | 424/725 |

OTHER PUBLICATIONS

Suzuki et al. Supressor Macrophages: A Role on the Growth of Transplanted Tumors and Regulation by an Extract of Licorice, Glycyrrhizin; Oncologia (Tokyo), 1987, 20(5), pp. 124-133; one page Abstract from STN database only provided.*

Raskin et al. Can an Apple a Day Keep the Doctor Away? Current Pharmaceutical Design, 2004, 10, pp. 3419-3429.*

H.B. MacPhillamy; Plant Science Bulletin, Apr. 1963, vol. 9, Issue 2, pp. 1-15.*

* cited by examiner

*Primary Examiner*—Patricia Leith
(74) *Attorney, Agent, or Firm*—Cooley Godward Kronish LLP

(57) ABSTRACT

This invention provides herbal compositions useful for increasing the therapeutic index of drugs, including those used in the treatment of disease, especially viral infections and neoplasms of cancer. This invention provides methods useful for improving the quality of life of an individual undergoing chemotherapy. Furthermore, this invention improves the treatment of disease by increasing the therapeutic index of chemotherapy drugs by administering the herbal composition PHY906 to a person undergoing such chemotherapy.

4 Claims, 38 Drawing Sheets

| t-tst (*PVALUE) AT DAY 14 | CONTROL (VEHICLE) | CPT-11 | PHY 906 |
|---|---|---|---|
| CPT011 | 0.02 | — | 0.02 |
| PHY 906 | 0.6 | 0.02 | — |
| CPT-11 + PHY 906 | 0.002 | 0.01 | 0.003 |

HERBAL COMPOSITION PHY906 AND ITS USE IN CHEMOTHERAPY

RELATED APPLICATIONS

This application is a Continuation-in-Part of U.S. application Ser. No. 10/220,876, filed on Dec. 30, 2002, now U.S. Pat. No. 7,025,993, which is the National Stage of International Application PCT/US01/07353, filed on Mar. 8, 2001, which is a Continuation-in-Part of U.S. application Ser. No. 09/522,055, filed Mar. 9, 2000, now abandoned, all of which are herein incorporated by reference in their entirety. This application also claims the benefit of U.S. Provisional Application 60/625,943, filed Nov. 9, 2004, which is herein incorporated by reference in its entirety.

FIELD OF THE INVENTION

The present invention relates to herbal compositions and herbal extracts useful for increasing the therapeutic index of drugs, including those used in the treatment of disease, especially viral infections and neoplasms of cancer. The methods of the present invention can be used to improve the quality of life of an individual undergoing chemotherapy. Specifically, the invention relates to the treatment of disease by increasing the therapeutic index of chemotherapy drugs by the herbal composition PHY906. More specifically, the invention relates to the treatment of cancer by increasing the therapeutic index of cancer chemotherapy drugs by the herbal composition PHY906.

BACKGROUND OF THE INVENTION

All publications and patent applications herein are incorporated by reference to the same extent as if each individual publication or patent application was specifically and individually indicated to be incorporated by reference.

Herbal Medicine

Herbal medicine has been in use for centuries by people of Asia and Europe. In the United States (US), herbs have become commercially valuable in the dietary supplement industry as well as in holistic medicine. Approximately one third of the US population has tried some form of alternative medicine at least once (Eisenberg et al., N. Engl. J. Med., 328:246-252 (1993)). Botanicals have also become a focal point for the identification of new active agents to treat diseases. Active compounds, derived from plant extracts, are of continuing interest to the pharmaceutical industry. For example, taxol an antineoplastic drug obtained from the bark of the western yew tree, has been found to be useful in the treatment of breast cancer (Gomez-Espuch et al., Bone Marrow Transplant, 25(3):231-235 (2000)).

There are many branches of herbal medicine around the world, such as Ayurveda, Unani, Sida and Traditional Chinese medicine (TCM). While modern Western medicine typically consists of administering a single chemical entity capable of intervening a specific biochemical pathway, each formula of TCM contains hundreds of chemical entities from several herbs which are designed to interact with multiple targets in the body in a coordinated manner. Although empirical practice contributed in a significant way to the herbal composition and prescription of these ancient herbal medicines, they are also supported, to a varying degree, by a set of theories which all are distinct from that of modern Western medicine in terms of anatomy, pharmacology, pathology, diagnosis treatment, etc. Among the different herbal medicine fields, TCM has developed a more complete set of theories over several centuries which have been well documented and practiced by local physicians caring for a huge population (>1.3 billion people) in greater China and in East Asia including Korea and Japan.

Traditional Chinese Medicine

Western medicine generally uses purified compounds, either natural or synthetic, mostly directed towards a single physiological target. However, the compositions used in TCM are usually composed of multiple herbs and compounds which are aimed at multiple targets in the body based on unique and holistic concepts. TCM mainly use processed crude natural products, with various combinations and formulations, to treat different conformations resulting in fewer side effects. The great potential of TCM has yet to be realized for the majority of the world's people.

Mixtures of botanical extracts, rather than a single compound are widely used throughout the world for the management of disease and are slowly gaining increased acceptance in Western countries (Okada, F., Lancet 348: 5-6(1996); Xiao P G, Xing S T and Wang L W, Journal of Ethnopharmacol 38: 167-175(1993)). The use of Traditional Chinese medicine is based on the interaction of many chemical components in an herbal preparation that act simultaneously and synergistically on multiple molecular targets and cellular mechanisms. These components serve various functions; some may be responsible for efficacy while others may decrease toxicity or increase bioavailability. Chinese herbal formulations are perhaps the best known botanical drugs and have been derived from empiric observations in humans over the millennia. The claimed indication of a given Chinese medicinal preparation, in many cases, is multiple rather than single. This is not surprising, due to the many phyto-chemical ingredients in a formulation that could exert actions at multiple targets. It is possible that one Chinese medicinal formulation may relieve more than one side effect associated with the use of cancer chemotherapeutic agents.

The herbs in a typical TCM prescription are assigned roles as the principal herb and the secondary herbs, including assistant, adjuvant and guiding herbs. The principal herb produces the leading effects in treating the cause or the main symptom of a disease. An assistant herb helps to strengthen the effect of the principal herb and produces leading effects in the treatment of the accompanying symptoms. There are three types of adjuvant herbs: 1) those that enhance the therapeutic effects of the principal and assistant herbs or treat tertiary symptoms, 2) those that reduce or eliminate the toxicity and other side effects of the principal and the assistant herbs and 3) those that act on complementary target tissues not specifically affected by the principal herb. A guiding herb directs the effect of other herbs to the affected site and/or coordinates and mediates the effects of the other herbs in the prescription or formulation. In contrast to most of the herbal medicines or supplements that consist of one or more parts of a single plant, the intended effects of TCM are directed at multiple tissues.

For example, a well-known TCM recipe, "Ephedra Decoction" used for treating asthma is composed of ephedra, cinnamon twig, bitter apricot kernel and licorice. Ephedra, as the principal herb, which expels cold, induces diaphoresis and facilitates the flow of the Lung Qi to relieve asthma, the main symptom. Cinnamon twig, as the assistant herb, enhances ephedra's induction of diaphoresis and warms the Channels to ensure the flow of Yang Qi for reducing headache and pantalgia. Bitter apricot kernel, as the adjuvant herb, facilitates the adverse flow of the Lung Qi and strengthens the asthma relief by ephedra. Licorice as the guiding herb moderates the effects of both ephedra and cinnamon to ensure a homeostasis of the vital Qi. While each of the four herbs clearly exhibits its respective activity, they complement as well as supplement each other when they are combined. In practice, the principal herb can be prescribed with one or more secondary herbs, depending on the symptoms at a patient's presentation (*Prescriptions of Traditional Chinese medicine*, Chapter One, pp 10-16, E. Zhang, editor in Chief, Publishing House, Shanghai University of Traditional Chinese medicine, 1998).

Qi refers to the total energy of the body. Herbs are used to achieve the optimum balance of Qi; that balance is believed to manifest itself in the overall health and vigor of the patient (K. C. Huang, The Pharmacology of Chinses Herbs, Second Edition, Page 2, 1999, CRC Press).

The main theories of TCM that guide the treatment of sickness with herbal medicine and other means, such as acupuncture, are 1) the theory of Yin and Yang; 2) the theory of Five Elements; 3) the theory of Viscera and Bowels; 4) the theory of Qi, Blood and Body Fluid; and 5) the theory of Channels and Collaterals.

In TCM, the first important aspect of making the proper diagnosis is to ascertain whether the disease is Yin or Yang, the two forces which the Chinese believe control the workings of the universe. Yin represents the feminine side of nature, encompassing darkness, tranquility, depth, cold, and wetness, while Yang represents a masculine principle, encompassing light, activity, height, heat, and dryness (K. C. Huang, The Pharmacology of Chinese Herbs, Second Edition, Page 2, 1999, CRC Press). Yin is commonly interpreted to be a negative force, while yang represents a positive force. The two forces are complementary, and neither can exist without the other. Thus, TCM attempts to achieve a balance between Yin and Yang.

In diagnosing a patient based on the philosophy of Yin and Yang, those patients who have a fever, are thirsty, constipated or have a rapid pulse condition are of Yang character. Those individuals who have an aversion to cold, are not thirsty, and diarrhea and a slow pulse condition are of Yin character. The property, flavor and function of herbs can also be classified according to Yin and Yang theory. For example, herbs of cold and cool nature belong to Yin, while herbs which are warm and hot in nature belong to Yang. Herbs with sour, bitter and salty flavor belong to Yin, while herbs with pungent, sweet and bland flavor belong to Yang. Herbs with astringent and subsiding function belong to Yin, while herbs with dispersing, ascending and floating function belong to Yang. In TCM, the principles of treatment are based on the predominance or weakness of Yin and Yang. Herbs are prescribed according to their property of Yin and Yang and their function for restoring the imbalance of the Yin and Yang. In so doing, the benefit of treatment is achieved.

According to the theory of Five Elements there are five basic substances that constitute the material world (i.e., wood, fire, earth, metal and water). In TCM this theory has been used to explain the physiology and pathology of the human body and to guide clinical diagnosis and treatment. Herbal physicians have applied the laws of generation, restriction, subjugation, and reverse restriction of the five elements to work out many effective and specific treatment regimens, such as reinforcing earth to generate metal (strengthening the function of the spleen to benefit the lung), replenishing water to nourish wood (nourishing the essence of the kidney to benefit the liver), supporting earth to restrict the wood (supplementing the function of the spleen to treat the hyperactivity of the liver), and strengthening water to control fire (replenishing the essence of the kidney to treat hyperactivity of the heart). Specifically, the property of some herbs is assigned to each of the five Elements for the purposes of guiding the prescription of a TCM recipe.

In TCM, the internal organs of the human body are divided into three groups: five Viscera (the Heart, the Liver, the Spleen, the Lung and the Kidney), Six Bowels (the Gall Bladder, the Stomach, the Large Intestine, the Small Intestine, the Urinary Bladder, and the Triple Warmer), the Extraordinary Organs (the Brain, the Medulla, the Bone, the Blood Vessel, the Gall Bladder, and the Uterus). In TCM, the Viscera or the Bowel are not only anatomic units, but also concepts of physiology and pathology concerning interactions among different organs. For example, the heart also refers to some of the mental functions and influence functions of blood, hair, tongue, and skin. Yin and Yang and the Five Elements influence the interactions among these internal organs, Viscera, Bowels, and Extraordinary Organs. The complexity of interplay of the theories is used to explain the pathology of diseases to which herbs are prescribed, as discussed below.

The prescription of herbal medicine in TCM starts with the diagnosis, which consists of four main items: interrogation, inspection, auscultation and olfaction, pulse taking and palpation. During the interrogation phase, much information is gathered, including the characteristics of the main symptoms. For instance, if the main symptom is characterized by the dull pain of the epigastric region, which may be relieved by warming and pressing, this suggests the insufficiency of the Spleen-Yang. Soreness and weakness of the loins and knees, intolerance of coldness with cold extremities manifests a weakness of the Kidney-Yang. During inspection, observations are made for vitality, skin color, and the general appearance and the condition of the tongue. For example, a pale complexion corresponds internally to the Lung of autumn, whose Qi is dry. This may occur when Yang Qi is lacking and the circulation of Qi and blood is impeded, or when the coldness in the channels and collaterals causes them to contract.

In TCM, it is from Qi, blood, and body fluid that come energy needed by the Viscera and Bowels, Channels and Collaterals, tissues, and other organs for carrying-out their physiological functions; and on which the formation and metabolism of Qi, blood and body fluid depend. Prescriptions of TCM consider the herbal effects on Qi and blood for treatments.

TCM holds that Channels, Collaterals, and their subsidiary parts are distributed over the entire body It is through them that herbs exert influence on pathological targets and achieve the improvement of sickness. For example, ephedra acts on the Channels of the Lung and Urinary Bladder so as to induce sweat for relieving asthma and promoting diuresis. As noted above, clinical applications of acupuncture are also guided by the theory of Channels and Collaterals.

In summary, while the nature or property of each herb in TCM may be assigned as Yin or Yang, and to one of the Five Elements, they act through Channels and Collaterals and are mediated via Qi, Blood and Fluid to yield therapeutic effects on targets, such as Viscera and Bowels. Pathogenic factors may be disguised as decoys through the very same systems of Channels and Collaterals to adversely affect the functions of Viscera and Bowels and thus cause sickness.

The Patenting of Herbal Compositions in the United States

U.S. Patents have been issued for herbal compositions used for the treatment of various diseases and other health-related problems afflicting mammals, including humans. For example, herbal compositions which include *Paeonia suffuticosa* have been found useful for treating viral infections, including infection from herpes and polio virus (U.S. Pat. No. 5,411,733).

Ocular inflammation can be treated with a pharmaceutical composition containing the plant alkaloid tetrandrine (U.S. Pat. No. 5,627,195). U.S. Pat. No. 5,683,697 discloses a pharmaceutical composition having anti-inflammatory, anti-fever, expectorant or anti-tussive action, wherein the composition includes plant parts from the species *Melia, Angepica, Dendrobium, Impatiens, Citrus, Loranthus, Celosia, Cynanchum* and *Glehnia*. An herbal formulation comprising extracts of the roots, rhizomes, and/or vegetation of *Alphinia, Smilax, Tinospora, Tribulus, Withania* and *Zingiber* has been found to reduce or alleviate the symptoms associated with rheumatoid arthritis, osteoarthritis, and reactive arthritis and to reduce the production of proinflammatory cytokines (U.S. Pat. No. 5,683,698). Compositions containing talc, silkworm excrement, and the ingredients of twelve different herbs have been shown to be effective in reducing inflammation, pain, and fever in mammals (U.S. Pat. No. 5,908,628).

Patents have also been issued for herbal compositions which find use in the treatment of cancer and cancer-related health problems. For example, U.S. Pat. No. 5,437,866 discloses a composition comprising a mixture of herbs, including species of *Scutellaria barbata*, as well as their extracts, which is used to ameliorate the effects of malignancy in humans. U.S. Pat. No. 5,665,393 discloses various herbal compositions which include *Glycyrrhiza glabra L.* and *Scutellaria baicalensis Georgi, Rabdosia rubescens*, and *Serenoa repens* for the treatment of prostate carcinoma. Further, antitumor herbal compositions include *Astragali radix, Paeonia radix, Cinnamomi cortex, Rhemannia radi* and *Glycyrrhizae radix* for use in increasing antitumor activity of mitomycin D and doxorubicin (U.S. Pat. No. 4,613,591 and U.S. Pat. No. 4,618,495).

Cancer and the Adverse Effects of Cancer Chemotherapy.

Cancer remains the second overall cause of death in the United States. There is an interest for a method for treating gastrointestinal cancers, including colorectal, liver, and pancreatic cancers, not because of their high incidence rates but rather, because of the high mortality rates, especially of pancreatic and liver cancer patients (Bergsland et al. Current Opinion in Oncology, 12: 357-361 (2000); Fernandez-et al. Curr Opin Gastroenterol, 18: 563-567 (2002); Jemal et al. Cancer J Clin, 52: 23-47 (2002); Skolnick et al., The Journal of the AMerican Medical Association, 276: 1457-1458 (1996)). From years 1992-1999, the study revealed that the five-year relative survival rates of colorectal cancer was 62.3% while that of liver cancer was 6.9% and 4.4% for pancreatic cancer. The median survivals of liver cancer was 3.5 weeks to 6 months while it was 4 to 6 months for pancreatic cancer (Jemal et al. Cancer J Clin, 52: 23-47 (2002)). With only very poor chemotherapeutic regimens available, pancreatic cancer has the highest mortality rate among all cancers in the United States, with a less than 5% survival rate 5 years from diagnosis (Jemal et al. Cancer J Clin, 52: 23-47 (2002)). Although several regimens are currently used in the clinical trials for hepatocellular carcinoma, there is no FDA-approved chemotherapeutic agent available. The low survival rates for both pancreatic and hepatocellular cancers are because diagnosis is difficult, the tumor growth is highly aggressive, surgical removal of tumor is of low probability, and the tumor has a high rate of chemotherapy resistance.

Gemcitabine is the only clinically approved chemotherapeutic agent for pancreatic cancer; however, the response rate in patients to gemcitabine is only 6-11% and the overall survival time is generally 4-6 months. Gemcitabine is a nucleoside analog with two mechanisms of action, including the inhibition of ribonucleotide reductase, an enzyme that converts nucleotide diphosphate to deoxynucleotide triphosphate and that is required for DNA synthesis and that competes with deoxycytidine triphosphate as a fraudulent base in DNA synthesis (Jemal et al., CA Cancer J Clin, 52: 23-47, 2002; Abbruzzese et al., Cancer Supplement, 95: 941-945, 2002; Hertel et al., Cancer Res., 50: 4417-4422, 1990; Pettersson et al., Pancreas, 23: 273-279, 2001; Philip et al., Cancer Supplement, 95: 908-911, 2002; Schultz et al., Oncology Research, 5: 223-228, 1993; Von Hoff et al., Current Opinion in Oncology, 14: 621-627, 2002). With the low response and survival rates of gemcitabine monotherapy, several gemcitabine-combination drug regimens have been tested clinically for improving therapeutic efficacy. These trials include gemcitabine with other commonly used and FDA-approved anti-cancer drugs including CPT-11, capecitabine and oxaliplatin (Bruns et al., Clinical Cancer Research, 6: 1936-1948, 2000; Jacobs et al., Cancer Supplement, 95: 923-927, 2002; Mcginn et al., Cancer Supplement, 95: 933-940, 2002; Oettle et al., Cancer Supplement, 95: 912-922, 2002). Unfortunately, no satisfactory combination drug regimens have been discovered and an effective regimen for pancreatic cancer is urgently needed.

Hepatocellular carcinoma is currently treated by surgical procedures and chemotherapy. Surgical removal and postoperative therapies may improve the outlook for some patients. Unfortunately, the vast majority of patients with hepatocellular carcinoma will have unresectable cancers. Although several regimens are currently used in the clinical trials for hepatocellular carcinoma, there is no FDA-approved chemotherapeutic agent available. Systemic chemotherapy has historically been of little to no value, although 5-fluorouracil (5-FU) and adriamycin (ADM) have demonstrated response rates from 10 to 20% (Suart et al., Am. J. Clin. Oncol., 19: 136-139, 1996). Capecitabine (Xeloda®) is rationally designed to be efficiently absorbed from the gastrointestinal tract as an oral prodrug and converted to 5-FU, preferentially in neoplastic tissues. Currently, capecitabine is approved as firstline therapy for the treatment of colorectal cancer and breast cancer with reduced toxicities (Berg et al., Semin. Oncol., 25: 53-59, 1998; Schwetz et al., JAMA, 286: 2085, 2001). Capecitabine is potentially an exciting new therapeutic agent. Although sharing the similar clinical response (13%) as 5-FU or ADM in liver cancer, capecitabine has distinct advantages, such as being an orally administered drug with relatively low toxicity that will improve the quality of life for hepatocellular carcinoma patients (Aguayo et al., Seminars In Oncology, 28: 503-513, 2001; Leung et al., Seminars In Oncology, 28: 514-520, 2001; Lozano et al, Oral Capecitabine (Xeloda®) for the Treatment of Hepatobillary Cancers (Hepatocellular Carcinoma, Cholangiocarcinoma, and Gallbladder Cancer). 19. 2000. Proceedings of ASCO).

Colorectal cancer has been reported to be the third most common cause of death from cancer in the United States (ACS Cancer Facts and Figures. American Cancer Society, 2004). Recently, the FDA approved the triple combination use of Oxaliplatin/5-FU/LV as firstline treatment for patients with advanced colorectal cancer. Oxaliplatin is a synthesized diaminocyclohexane platinum compound, which like cisplatin, causes platinum-DNA adduct formation and destroys the integrity of DNA (Eric Raymond et al., Molecular Cancer Therapeutics, 1: 227-235, 2002). Other types of chemotherapeutic agents, such as 5-FU, CPT-11, are common chemotherapeutic agents used in the treatment of colorectal cancer. Unfortunately, severe diarrhea has been identified as one of the dose-limiting toxicities among patients treated with chemotherapy.

Medical oncology has had a great impact in changing the practice of medicine in the past several decades as curative treatments for a variety of previously fatal malignancies have been identified. However, few categories of drugs in common use have a narrower therapeutic index and a greater potential for causing harmful side effects than do the antineoplastic drugs (Calabresi and Chabner, 1996).

Anticancer agents, like many other potent drugs with only moderate selectivity, may cause severe toxicity. Common adverse effects associated with cancer chemotherapy include, but are not limited to, gastrointestinal complications (e.g., diarrhea, nausea, vomiting, anorexia and mucositis), pain, appetite loss, bone marrow/hematologic complications (e.g., leukopenia, neutropenia, anemia, hemorrhage, thrombocytopenia), fatigue and sleep disturbance.

of the Han Dynasty; Hong-Yen Hsu and Chau-Shin Hsu, Commonly used Chinese Herb Formulas with Illustrations, Oriental Healing Art Institute, California, (1980)). PHY906 consists of four herbs with proportion of *Scutellariae baicalensis Georgi* (scute), *Paeonia lactiflora pall* (white peony root), *Glycyrrhizae uralensis Fisch* (licorice) and the fruit of *Fructus ziziphi* (date) mixed in the proportions 1.5:1.0:1.0:1.0 by dry weight, respectively. It should be noted that each herb possesses a distinct pharmacological profile that includes anticancer and antiviral activity, hematological and immunological stimulation, analgesic activity, vasodilation, liver protection, antioxidation, and appetite improvement, as shown in Table 1.

TABLE 1

Putative Biological Activities of Individual Herbs in the PHY906 Formulation.

| | Anti-Cancer | Immuno-Modulation | Anti-Bacteria | Anti-Inflammatory | Nervous System | Others |
|---|---|---|---|---|---|---|
| *Scuellaria baicalensis Georgi* | + | + <br> ↑↓ lymphocyte & macrophage activity bifunctional | + | + | − | antiviral, antibacterial antidiarrhea, diuretic, vasodilation, ↓ lipid, anticoagulation, antioxidant, antiemetic, liver protection |
| *Paeonia lactiflora pall* | + | + <br> ↑↓ macrophage activity bifunctional modulator | + | + | + <br> analgesic | vasodilation, liver protection, diuretic anticoagulation, ↓ intestine movement |
| *Fructus ziziphi* | + | + <br> anti IgE action | − | − | + <br> ↑ sleep | liver protection, muscle endurance, improve appetite |
| *Glycyrrhiza uralensis Fisch* | + | + <br> ↑ macrophage activity <br> ↑ interferon & ↑ IL-1 <br> ↑ lymphocyte <br> ↑ interferon & ↑ IL-2 <br> ↑ NK activity <br> ↓ IgE | + | + | + <br> analgesic | Antidiuretic <br> ↓ intestine movement <br> ↓ lipid (LDL, TC) <br> antioxidant <br> antiviral <br> anticoagulation <br> anticomplement |

↑: increase
↓: decrease
↑↓: decrease or increase
+: effect
−: no effect

The inventors of the present invention performed a literature search for Chinese medicinal formulations that have been used for the treatment of symptoms associated with cancer chemotherapy. TJ-14, a botanical formulation with seven herbs, was reported to potently prevent diarrhea caused by CPT-11 in cancer patients (Kase, Y, Hayakawa T, and Aburada M. et al., Jpn. J. Pharmacol. 75, 407-413 (1997); Marita M., Nagai E and Hagiwara H. et al., Xenobiotica. 23, 5-10 (1993)). The diarrhea was hypothesized to occur from the accumulation of SN-38, an active metabolite of CPT-11, created by intestinal microorganisms. The inventors believe that baicalin, an inhibitor of β-glucuronidase, is the active ingredient in TJ-14 that alleviates diarrhea caused by CPT-11 (Kase, Y, Hayakawa T, and Aburada M. et al., Jpn. J. Pharmacol. 75, 407-413 (1997); Marita M., Nagai E and Hagiwara H. et al., Xenobiotica. 23, 5-10 (1993); Takasuna K, Takehiro H, Hirohashi M, et al., Cancer Chemother Pharmacol. 42:280-286 (1998); Takasuna K, Takehiro H, Hirohashi M, Kato M, et al., Cancer Res. 56:3752-3757 (1996)). Therefore, several Chinese herbal formulations containing the root of *Scuellaria baicalensis Georgi*, which is rich in baicalin, were evaluated. Among several formulations examined in the laboratory, the inventors chose PHY906. This specific formulation was established more than 1500 years ago for the treatment of diarrhea, abdominal spasms, fever, headache, vomiting, nausea, extreme thirst, and subcardial distention (Shang Han Lun Until now, PHY906 has been prescribed as a single medicine only, rather than in combination with synthetic drugs. However, it is conceivable that one of the documented uses of PHY906 might actually be useful in alleviating the side effects induced by chemotherapy. Although some of the major chemical components in each of the four herbs of PHY906 have been identified, and their pharmacological activities have been examined (Chinese Botany Shanghai Science and Technology Publishing Company (1999); Huang, H-C, Wang, H-R, and Hsieh, L-M., Eur J of Pharmacol 251:91-93 (1994); Lin, C-C and Shieh, Am J Chinese Med 1:31-36 (1996); Tang, W. and Eisenbrand, G., Chinese Drugs of Plant Origin: Chemistry, Pharmacology and Use in Traditional and Modern Medicine pp. 919-929. Springer-Verlag Press, New York, (1992)), the biological properties of PHY906 may not be fully predicted by the identified ingredients.

SUMMARY OF THE INVENTION

The inventors of the present invention have unexpectedly discovered that the herbal composition PHY906 can be used in various methods for increasing the therapeutic index of one or more chemotherapeutic compounds and for modulating hematopoietic activity. The methods disclosed herein can be used to improve the quality of life for chemotherapy patients by increasing the efficacy of chemotherapeutic agents and decreasing the toxicity of the agents when they are administered with PHY906.

This invention provides the herbal composition PHY906 combined with a pharmaceutically acceptable carrier and optionally including one or more chemotherapeutic compounds or antiviral agents. The four plant species which are chosen to make a particular formulation of PHY906 are each selected from one of four different groups of herbs: Scutellaria, Licorice, Peony Alba and Ziziphi fruit. The herbs are chosen so as to obtain one or more of the desirable attributes of PHY906, wherein such attributes include, but are not limited to, increasing the therapeutic index of one or more chemotherapeutic compounds, enhancing the antitumor activity of one or more chemotherapeutic compounds or enhancing the antiviral activity of one or more antiviral agents, modulating hematopoietic activity, modulating hematological and immunological activity, and improving the quality of life of a mammal undergoing chemotherapy or antiviral therapy.

Chemotherapeutic compounds or agents encompassed by this invention include, but are not limited to, those useful for treating cancer, parasitic infections, and microbial infections.

Antiviral compounds or agents encompassed by this invention include those that are useful for treating viral infections, diseases, or conditions.

The compositions and methods of the present invention are useful for treating any mammal. More specifically, the methods of the present invention are useful for treating humans.

This invention further provides compositions which include a pharmaceutically acceptable carrier; material or chemical from a plant species of each of the following genera of herbs: *Scutellaria, Glycyrrhiza, Ziziphus* and *Paeonia*; and one or more chemotherapeutic compounds. Preferably, the composition comprises a pharmaceutically acceptable carrier, an herbal preparation comprising *Scutellaria, Glycyrrhiza, Ziziphus* and *Paeonia*, and a chemotherapeutic formulation comprising one or more chemotherapeutics or antiviral agents. More preferably, the herbal preparation comprises material or chemical from *Scutellaria, Glycyrrhiza, Ziziphus* and *Paeonia*. Most preferably, this invention provides such compositions which include *Scutellaria baicalensis, Glycyrrhiza uralensis, Ziziphus jujuba*, and *Paeonia lactiflora*.

The herbal compositions of the present invention are particularly useful with cancer chemotherapies, such as, but not limited to, treatment with irinotecan (CPT-11, Camptosar®), 5-fluorouracil (FU or 5-FU), leucovorin (LV), VP-16, beta-L-Dioxolane-cytidine (L-OddC), capecitabine, gemicitabine, oxaliplatin, doxorubicin, thalidomide, and combinations thereof, such as but not limited to FU/LV, CPT-11/FU/LV, oxaliplatin/FU/LV, and gemcitabine/oxaliplatin. The present invention provides compositions comprising PHY906 and one or more chemotherapeutic agents such as but not limited to CPT-11, 5-FU, VP-16, L-OddC, capecitabine, gemicitabine, oxaliplatin, and combinations thereof, such as but not limited to FU/LV, CPT-11/FU/LV, and oxaliplatin/FU/LV. The present invention also provides compositions comprising PHY906 and one or more analogs and derivatives of chemotherapeutic agents, such as CPT-11, 5-FU, VP-16, L-OddC, LV, capecitabine, gemicitabine, doxorubicin, thalidomide, and oxaliplatin.

The herbal compositions of the present invention are particularly useful with antiviral therapies. Preferably, the herbal compositions are administered with antiviral agents useful for treating AIDS. More preferably, the herbal compositions are administered with antiviral agents selected from the group consisting of AZT, D4T, DDI, 3TC, ddC, and FTG.

The present invention provides methods for increasing the therapeutic index of cancer therapeutic compounds used in the treatment of cancer. The present invention also provides methods for increasing the therapeutic index of antiviral agents used in the treatment of antiviral diseases. More specifically, the present invention provides such methods which include administering one or more anticancer or antiviral agent in combination with a therapeutically effective amount of a composition comprising a pharmaceutically acceptable carrier and material or chemical from, or herbal preparation comprising a plant species of each of the following genera of herbs: *Scutellaria, Glycyrrhiza, Ziziphus* and *Paeonia*. The methods of the present invention provide the use of material or chemical from, or herbal preparation comprising such herbs which is in the form of a granulated extract from an aqueous solution that includes but is not limited to water and alcohol. Such compositions can be in an ingestible form, such as, but not limited to, powders, capsules, liquids and tablets. Alternatively, the methods of the present invention use such compositions in the form of a suppository.

The present invention also provides methods of treating diseases in mammals in need of such treatment which includes administering a therapeutically effective amount of a composition comprising a pharmaceutically acceptable carrier; material or chemical from, or herbal preparation comprising a plant species of each of the following genera of herbs: *Scutellaria, Glycyrrhiza, Ziziphus* and *Paeonia*; and one or more chemotherapeutic compounds.

The present invention further provides methods of treating diseases in a mammal in need of such treatment which includes administering a therapeutically effective amount of one or more chemotherapeutic compounds or antiviral agents and a composition which includes a pharmaceutically acceptable carrier; material or chemical from, or herbal preparation comprising a plant species of each of the following genera of herbs: *Scutellaria, Glycyrrhiza, Ziziphus* and *Paeonia*. The present invention includes such methods wherein the composition is administered before the administration of the one or more chemotherapeutic compounds. The present invention also includes such methods wherein the composition is administered after the administration of the one or more chemotherapeutic compounds.

The present invention provides methods of modulating hematopoietic activity for the treatment of a disease by administering to a mammal in need of such treatment a therapeutically effective amount of a composition consisting essentially of a pharmaceutically acceptable carrier and material or chemical from or herbal preparation comprising a plant species of each of the following genera of herbs: *Scutellaria, Glycyrrhiza, Ziziphus* and *Paeonia*. The present invention provides such methods wherein the material or chemical from the herbs is in the form of a granulated extract from an aqueous solution that includes but is not limited to water and alcohol. Specifically, the present invention provides such methods wherein the composition is in an ingestible form, such as, but not limited to, powders, capsules, liquids and tablets. Alternatively, the present invention provides such methods wherein the composition is in the form of a suppository.

The present invention also provides methods of improving the quality of life of a mammal undergoing chemotherapy or antiviral therapy which comprises administering a therapeutically effective amount of one or more chemotherapeutic compounds and a composition comprising:

i) a pharmaceutically acceptable carrier; and ii) material or chemical from a plant species of each of the following genera of herbs: *Scutellaria, Glycyrrhiza, Ziziphus* and *Paeonia*.

The present invention contemplates administering a chemotherapeutic formulation comprising one or more chemotherapeutic agents in combination with a composition comprising a pharmaceutically acceptable carrier and an herbal preparation comprising a plant species of each of the following genera of herbs: Scutellaria, Glycyrrhiza, Ziziphus and Paeonia.

The present invention also contemplates administering an antiviral formulation comprising one or more antiviral agents in combination with a composition comprising a pharmaceutically acceptable carrier and an herbal preparation comprising a plant species of each of the following genera of herbs: Scutellaria, Glycyrrhiza, Ziziphus and Paeonia.

The present invention uses the disclosed herbal compositions for increasing the antitumor activity of chemotherapeutic agents, increasing the antiviral activity of antiviral agents, decreasing the toxicity of the chemotherapeutic or antiviral agent, modulating the hematological and immunological activity of a mammal, and improving the quality of life of a mammal undergoing chemotherapy or antiviral therapy.

In one aspect, the present invention discloses a method of treatment comprising a chemotherapeutic regimen comprising one or more chemotherapeutic compounds and a composition comprising a pharmaceutically acceptable carrier and an herbal preparation comprising Scutellaria, Glycyrrhiza, Ziziphus and Paeonia. In another aspect, the present invention discloses a method of treatment comprising an antiviral regimen comprising one or more antiviral agents and a composition comprising a pharmaceutically acceptable carrier and an herbal preparation comprising Scutellaria, Glycyrrhiza, Ziziphus and Paeonia.

Further, the present invention provides a therapeutic regimen comprising one or more chemotherapeutic or antiviral compound and a composition comprising a pharmaceutically acceptable carrier and an herbal preparation comprising Scutellaria, Glycyrrhiza, Ziziphus and Paeonia.

Additionally, the present invention discloses chemotherapeutic regimens and compositions comprising three chemotherapeutic compounds, preferably, CPT-11/FU/LV or oxaliplatin/CPT-11/FU/LV and an herbal preparation comprising Scutellaria, Glycyrrhiza, Ziziphus and Paeonia or material or chemical from a plant species of each of the following genera of herbs Scutellaria, Glycyrrhiza, Ziziphus and Paeonia. The present invention contemplates antiviral therapies comprising one or more antiviral agents.

DETAILED DESCRIPTION OF THE PREFERRED EMBODIMENTS

I. General Description

The present invention is based in part on the finding that PHY906 reduced chemotherapy-induced toxicities including body weight loss and mortality, and that PHY906 also enhanced the antitumor efficacy of a broad-spectrum of anticancer agents, such as CPT-11, 5-FU, VP-16, L-OddC, capecitabine, gemcitabine, oxaliplatin, doxorubicin, thalidomide, CPT-11/5-FU/LV, gemcitabine/oxaliplatin, and oxaliplatin/5-FU/LV in in vivo animal models. PHY906 is a traditional Chinese botanical formulation consisting of 4 different herbs, and it has been used for some 1800 years to treat gastrointestinal ailments, some of which are commonly observed side effects in cancer patients undergoing chemotherapy.

The present invention is also based in part on the finding that PHY906 significantly enhanced the therapeutic index of chemotherapeutic agents studied in both hepatocellular and pancreatic cancer models. PHY906 was co-administered with either the oral 5-FU prodrug capecitabine, CPT-11, doxorubicin, or thalidomide in human hepatocellular xenografts mouse model, and with gemcitabine, oxliplatin, gemcitabine/oxaliplatin in mouse pancreatic cancer model. Co-administration of PHY906 with either capecitabine or gemcitabine in animal models did not alter the pharmacokinetic profile of capecitabine, gemcitabine, or their respective metabolites.

Figure 35:
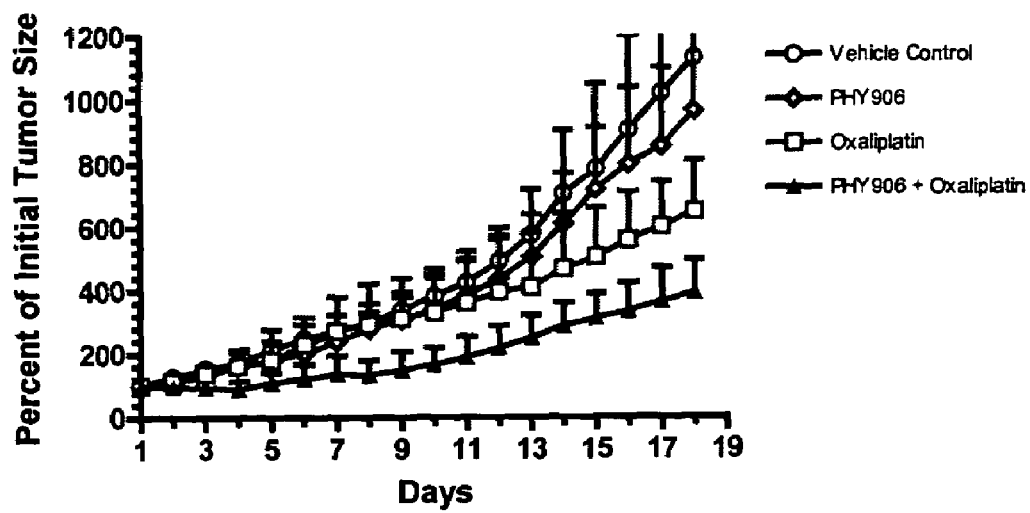
FIG. 35. Effect of PHY906 on Anti-Tumor Activity of Oxaliplatin in Colon 38 Bearing BDF-1 Mice. Oxaliplatin (10 mg/kg, D1) was given intraperitoneally on day 1. PHY906 was given orally 30 min before oxaliplatin twice a day on days 1-4 at 500 mg/kg (N=5 in each group).
Figure 36:
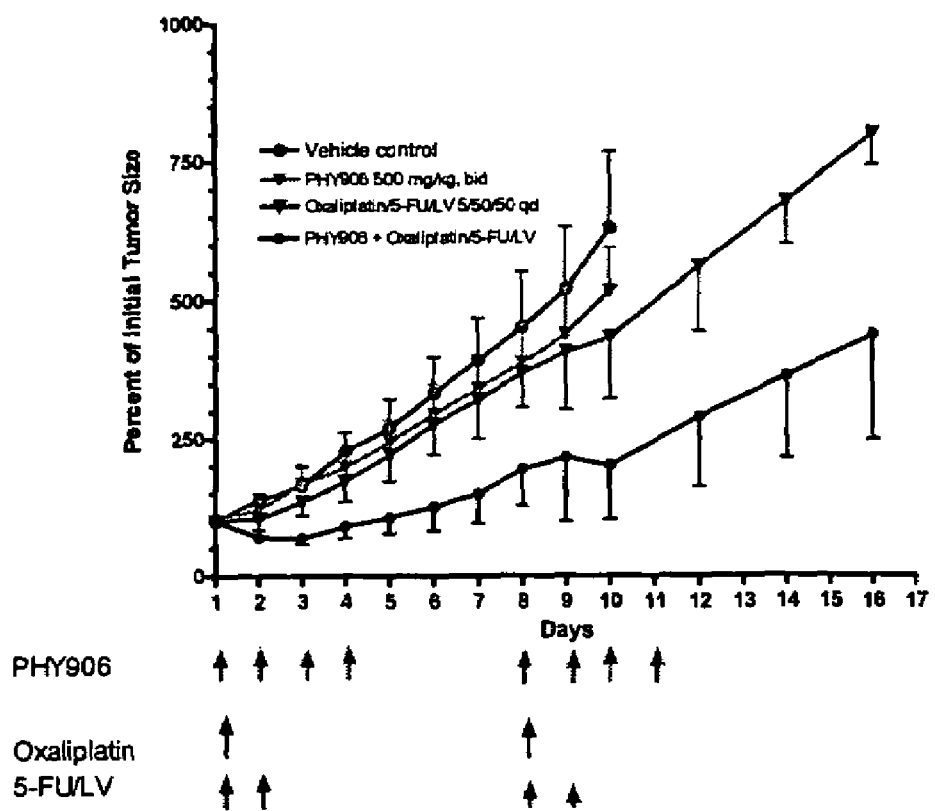
FIG. 36. Effect of PHY906 on Anti-Tumor Activity of Oxaliplatin/5-FU/LV in Colon 38 Bearing BDF-1 Mice. 5-FU and LV (50 mg/kg each) were given intraperitoneally on days 1, 2, 8 and 9. Oxaliplatin (5 mg/kg) was given intraperitoneally on days 1 and 8. PHY906 was given orally 30 min before 5-FU/LV twice a day on days 1-4 and days 8-11 at 500 mg/kg (N=5 in each group).
Figure 37:
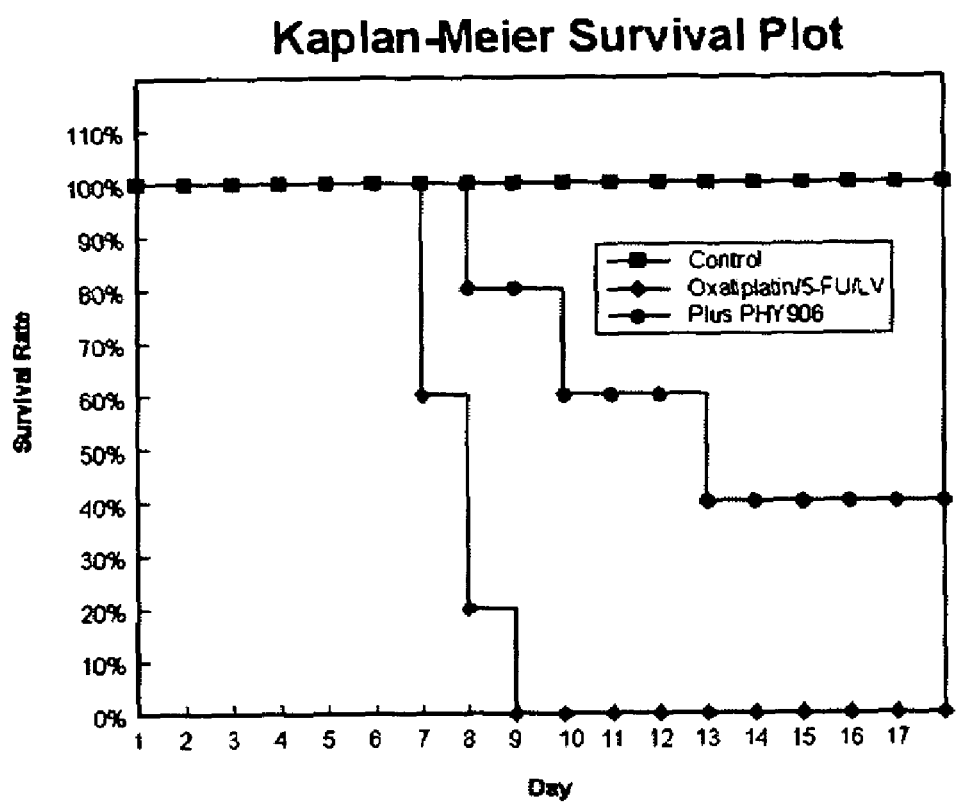
FIG. 37. Kaplan-Meier Survival Plot on Colon 38 Bearing BDF-1 Mice Treated With (A) Vehicle; (B) Oxaliplatin/5-FU/LV; or (C) PHY906 plus Oxaliplatin/5-FU/LV. Oxaliplatin (10 mg/kg, D1) and 5-FU/LV (50 mg/kg each, D1-2) were given intraperitoneally starting on day 1. PHY906 was given orally 30 min before oxaliplatin/5-FU/LV twice a day on days 1-4 at 500 mg/kg (N=5 in each group).

The effect of PHY906 was also examined on the antitumor activities of oxaliplatin, 5-FU/LV, and oxaliplatin/5-FU/LV in colorectal cancer mouse models. The present invention is based in part on the finding that PHY906 enhanced the anti-tumor activities of oxaliplatin, and oxaliplatin/5-FU/LV as shown in FIGS. 35 and 36. PHY906 not only reduced the mortality to 60%, but also delayed the onset of animal death caused by oxaliplatin/5-FU/LV, as shown in FIG. 37.

Biochemical studies revealed that the PHY906 formulation possesses a wide range of pharmacological activities. The potential mechanisms of action of PHY906 include (1) enhancement of oral uptake of pharmacologically active agents with inhibition in intestinal CYP3A4; (2) inhibition of NF-κB activity; (3) inhibition of MMP activity; and (4) destruction of the integrity of sinusoids in hepatoma.

These preclinical in vivo studies have provided the rationale for developing PHY906 in the clinical setting. A phase I/IIA double-blind, placebo-controlled, dose-escalation study of PHY906 was initiated to evaluate the potential effect of PHY906 in modulating CPT-11-induced diarrhea associated with the bolus, weekly schedule of CPT-11/5-FU/LV in advanced colorectal cancer patients. A second phase I/II open-label, dose-escalation clinical trial has been opened to patient accrual to evaluate the role of PHY906 in combination with capecitabine in the treatment of hepatocellular carcinoma.

PHY906 has also been shown in mouse models to enhance the therapeutic index of several anticancer agents such as irinotecan (CPT-11), 5-fluorouracil (5-FU), irinotecan/5-fluorouracil/leucovorin (LV), etoposide (VP-16) and L-OddC by both potentiating the antitumor effects of the therapeutic agents as well as reducing various host toxicities. To investigate whether there is a need of all four botanicals to achieve the full observed biological activity, five formulations were studied: the complete formulation with all four botanicals and each of four formulations missing one of the botanical ingredients (A=*Scutellaria*, B=*Paeonia*, C=*Ziziphus* and D=*Glycyrrhiz*). In the BDF-1 mice bearing Colon 38 tumor model, the potentiation of the antitumor effect of CPT-11 was impaired when either botanical A or botanical B was removed from the PHY906 formulation. In contrast, botanicals C and D were not found to contribute to the potentiation of the antitumor effect of CPT-11. However, when examining weight loss as an undesired toxic side effect of CPT-11, all of the botanicals except for B, contributed in protecting against body weight loss. Thus, the biological activity of PHY906 observed require all four botanicals.

Studies of the effects of botanicals on cytochrome P450 isozymes (CYP1A2, 2C9, 2C19, 2D6 and 3A4) in vitro have also been conducted to examine potential action of botanicals on isolated enzyme targets. One of these enzymes, CYP3A4, is known to be the major metabolizing enzyme for CPT-11. While studies in the BDF-1 mice bearing Colon 38 tumor model indicate that PHY906 has no effect on the pharmacokinetics or pharmacodynamics of CPT-11, it was observed that PHY906 was found to act as inhibitor of individual cytochrome P450 isozymes with different potency. Individual P450 inhibition studies of both the single botanicals as well as the four separate formulations of three botanicals, indicate that there are interactions between specific botanicals that modulate the individual enzyme inhibitory effects. These studies indicate the complex, compensatory and multifactorial nature of botanical drug actions in both in vivo and in vitro studies in keeping with the philosophy of original traditional Chinese medicine. PHY906 was in Phase I//IIa clinical trials as a modulator of CPT-11/5-FU/LV in colorectal cancer patients.

In summary, the present invention is based in part on the following findings:

1. In different mouse models, PHY906 increased the therapeutic index of various types of chemotherapeutic agents in human pancreatic cancer, hepatocellular carcinoma, and colorectal cancer. Specifically, PHY906 increased the therapeutic index of a broad spectrum of chemotherapeutic agents by enhancing the antitumor activity, decreasing the mortality, and protecting against the body weight loss.

2. PHY906 did not alter the pharmacokinetics of these chemotherapeutic agents in mouse models.

3. The mechanisms of drug action of PHY906 in the potentiation of studied cancer chemotherapeutic agents can be attributed but not limited to the inhibition on NF-κB, MMPs, or to the destruction of the integrity of hepatoma sinusoids.

4. All four herbs (A=*Scutellaria*, B=*Paeonia*, C=*Ziziphus* and D=*Glycyrrhiz*) were required in PHY906 formula for the full range of observed efficacy:
 Herb A contributed to both body weight loss protection and antitumor potentiatiation ($p<0.05$) in the PHY906 formula.
 Herb B contributed to the enhancement of antitumor activity of PHY906 ($p<0.05$), but not to the protection of cancer chemotherapy drug-induced body weight loss.
 Herbs C and D protected against the body weight loss induced by cancer chemothreapy agents.

5. Different batches of PHY906 showed consistency in both human CYP450 inhibition and cell growth inhibition:
 Herb A was a potent inhibitor for human CYP450 as well as for cell growth.
 Herb D showed very low cytotoxicity in the cell lines examined and is a very weak inhibitor for human CYP450.

6. PHY906 showed strong inhibitory activity against human CYP450 in vitro. However, animal data revealed that PHY906 did not affect the CPT-11 metabolism or impair the anticancer activity of chemotherapeutic agent.

Cancer chemotherapeutic agents often induce severe adverse side effects that can affect patients' quality of life, as well as interfere with the therapeutic regimen. The present invention is based in part on the discovery that Chinese herbal medicines in combination with standard anticancer agents are useful for reducing the adverse side effects of cancer chemotherapeutic agents and for improving the quality of life of patients undergoing chemotherapy. PHY906, a botanical formulation composed of four distinct herbs, has been used for centuries for the treatment of various gastrointestinal ailments and other illnesses in China. The present invention is based on the results of experiments performed in animal models evaluating the potential efficacy of PHY906 in relieving side effects induced by cancer chemotherapy agents in colorectal cancer patients. Specifically, the present invention is based in part on the finding that PHY906 reduces various host toxicities induced by CPT-11, FU, FU/LV, CPT-11/FU/LV, L-OddC, VP-16, thalidomide, doxorubicin, capecitabine, gemcitabine, oxaliplatin, gemcitabine/oxliplatin or oxaliplatin/FU/LV treatment, as well as maintaining and even potentiating the antitumor activity of chemotherapeutic agents. More specifically, PHY906 enhances the therapeutic index of CPT-11, 5-FU, capecitabine, oxaliplatin, doxorubicin, thalidomide, VP-16, L-OddC, and the triple combinations of CPT-11/FU/LV and oxaliplatin/FU/LV by both potentiating antitumor effects of the therapeutic agents and reducing various host toxicities. These findings are not limited to one specific anticancer agent or one specific tumor model.

The present invention is also based in part on the discovery of a regimen that can be used in conjunction with various anticancer agents to lower the dose limiting toxicity and increase efficacy of the agents. This discovery is an extremely important addition to the armamentarium of treatment approaches for human cancers.

II. Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, "cancer chemotherapeutic" or "cancer chemotherapeutic agent" refers to chemotherapeutic agent for the treatment of neoplastic disease or cancer.

As used herein, "chemotherapy" refers to treatment of disease by means of chemical substances or drugs.

As used herein, the term "chemotherapeutic formulation" refers to a composition comprising a chemotherapeutic agent.

As used herein, the term "extract" refers to a concentrated preparation of a vegetable or animal drug obtained by removing the active constituents therefrom with a suitable menstruum (solvent), evaporating all or nearly all the solvent and adjusting the residual mass or powder to a prescribed standard. Extracts are prepared in three forms, semiliquid or of syrupy consistency, pilular or solid, and as dry powder (see http://www.graylab.ac.uk/cgi-bin/omd?query=extract).

In one embodiment, extracts are concentrated forms of crude drugs used in a variety of solid and semisolid dosage forms (in Remington's Pharmaceutical Sciences 17th ed. (*Gennaro*, ed), Chapter 84, pp. 1516-1517, Mack Publishing Co, Easton, Pa. (1985)). For example, pilular (i.e., plastic masses) extracts are of a consistency where they are suitable for pill masses and are made into pills (e.g., pure *Glycyrrhiza* extract USP). Further, pilular masses are well suited for use in ointments and suppositories. Powdered extracts are better suited for powdered formulations such as capsules, powders and tablets. Further, semiliquid or extracts of syrupy consistency can be used in the manufacture of pharmaceutical preparations (Remington's Pharmaceutical Sciences, 1985).

In a related aspect, extracts can be considered solutions of active ingredients obtained by soaking or steeping preparations of vegetable or animal crude drugs in liquids (maceration) or by passing such crude drugs through porous substances (percolation) for use as a medicinal agent. Further, medicinal agents of this type may be in the form of tinctures or fluidextracts [sic] (Remington's Pharmaceutical Sciences, 1985).

In one embodiment, the extract is in tincture form. For example, tinctures may include, but are not limited to, alcoholic or hydroalcoholic solutions prepared from vegetable matter or from chemical substances. Tinctures may be made by either percolation or maceration and are traditionally assigned potency by the amount of activity of a specified weight of the drug (in grams) per 100 ml of tincture (Remington's Pharmaceutical Sciences, 1985). For example, Sweet Orange Peel Tincture contains 50 g of sweet orange peel per 100 ml of tincture.

In another embodiment, the extract is in fluid extract [sic] form. For example, fluid extracts include, but are not limited to, liquid preparations of vegetable drugs comprising alcohol as the solvent or as a preservative, or both, where traditionally each ml contains the therapeutic constituents of 1 gram of the drug that it represents. Fluidextracts can be made by percolation as a general method (Remington's Pharmaceutical Sciences, 1985).

As used herein, the term "hematological activity" refers to activity associated with blood and blood forming organs.

Technically speaking, the term "herb" refers to a small, non-woody (i.e., fleshy stemmed), annual or perennial seed-bearing plant in which all the aerial parts die back at the end of each growing season. Herbs are valued for their medicinal, savory or aromatic qualities. As the word is more generally used and as the word is used herein, an "herb" refers to any plant or plant part which has a food supplement, medicinal, drug, therapeutic, or life-enhancing use. Thus, as used herein, an herb is not limited to the botanical definition of an herb but rather to any botanical, plant or plant part used for such purposes, including any plant or plant part of any plant species or subspecies of the Metaphyta kingdom, including herbs, shrubs, subshrubs, and trees. Plant parts used in herbal compositions include, but are not limited to, seeds, leaves, stems, twigs, branches, buds, flowers, bulbs, corns, tubers, rhizomes, runners, roots, fruits, cones, berries, cambium and bark.

As used herein, an "herbal composition or formulation" refers to any composition or formulation which includes herbs, herbal plants, herbal plant parts and/or herbal extracts. Thus, as used herein, an herbal composition or formulation includes herbal preparation comprising herbal food supplements, herbal medicines, herbal drugs, and medical foods. Examples of herbal compositions include, but are not limited to, the following components: a whole plant or a plant part of a single plant species; whole plants or plant parts of multiple plant species; multiple components derived from a single plant species; multiple components derived from multiple plant species; herbal extracts; or any combination of these various components. Also contemplated are herbal compositions comprising one or more chemicals derived from a single or multiple plant species.

For a thorough review of various herbal compositions, see, for example, Kee Chang Huang, The Pharmacology of Chinese Herbs, CRC Press (1993), herein incorporated in its entirety.

As used herein, the term "immunological activity" refers to activity associated with the immune system, immunity, induced sensitivity, and allergy.

As used herein, the term "mortality rate" refers to the proportion of deaths in a population or to a specific number of the population, where mortality is defined as the death rate or ratio of the total number of deaths to the total population. For example, the 30 day mortality rate after ischemic stroke symptom onset can vary from about 13.3% (e.g., after treatment with tissue type plasminogen activator, see Albers et al., *JAMA* (2000) 283(9):1145-1150) to greater than about 65% (e.g., hemorrhage stroke, see Mahaffey et al., *Am Heart J* (1999) 138(3 Pt 1):493-499).

As used herein, the term "Quality of life (QOL)" refers to the general well-being of an animal, especially a mammal, even more specifically a human. The QOL of an individual can be evaluated based on any one parameter, a group of two or more parameters or on a general overall evaluation or score. Examples of useful indices for evaluating QOL include, but are not limited to, those associated with sleeping patterns; eating patterns; drinking patterns; agility; mobility; skin tone; vision; hair retention/loss/growth; muscle tone; muscle mass; strength; weight; sinus health; presence, absence or degree of inflammation; feelings of discomfort; ability to accomplish specific tasks; anxiety levels; response times; ability to concentrate; memory retention; verbal ability; sound perception; presence, absence or degree of headaches; muscle spasms; nerve damage; taste; touch; smell; presence or absence of opportunistic diseases; and presence or absence of parasites.

As used herein, the term "regimen" refers to a program of treatment.

As used herein, the term "therapeutic index" refers to how selective a drug is in producing the desired effects. Therapeutic index is the ratio of $LD_{50}$ to $ED_{50}$. $ED_{50}$, the median effective dose, is the dose of a drug required to produce a specified effect in 50% of the population. $LD_{50}$ is the median lethal dose as determined in experimental animals.

III. Specific Embodiments

A. Chemotherapy

In general, chemotherapy refers to the treatment of disease, especially neoplasms, parasitic infections and microbial diseases, with chemical agents that in some manner act on the infective organisms or tumors.

1. Cancer Chemotherapy

Introduction: Chemotherapy continues to be one of the most effective modalities for treating cancer in patients. Although quite effective, chemotherapeutic agents are also well known to adversely disrupt the quality of life of patients. Some commonly observed side effects include myelosuppression and immunosuppression, diarrhea, peripheral neuropathy, nausea and vomiting, fever, liver dysfunction and cardiac toxicity, etc. ("Physicians Desk Reference" (1999) Medical Economics Company). In many instances, these adverse side effects prevent patients from receiving escalating doses or additional courses of therapy, thereby comprising the efficacy of these agents. Alleviation of some or all of these side effects, without compromising the anticancer activity of chemotherapeutic agents, would not only improve the quality of life (QOL) of cancer patients, but also allow for a more aggressive treatment protocol, resulting in possibly improved clinical success. Currently, most supportive therapies use single agents, such as anti-emetics, anti-mucositis agents, and colony growth factors, that target individual side effects, but do not address the broad spectrum of side effects associated with cancer chemotherapy (Bleiberg H and Cvitkovic E., Eur J Cancer 32A(Suppl 3):S18-S23 (1996); Wierda D. and Matamoros M., Toxicol & Applied Pharmacol 75:25-34(1984); Goldber R. M. and Erlichman C., Oncology 12: 59-63 (1988)).

Drugs for treating cancer include the more conventional natural products such as paclitaxel (TAXOL), the semisynthetics such as etoposide, and many newer, diverse agents such as interleukin-2 and all-trans-retinoic acid. For a comprehensive list of chemotherapeutic agents useful in treating neoplastic diseases, see, for example, Table X-1 at pages 1227-1229 of Calabresi and Chabner (1996).

The major adverse effects associated with commonly administered cancer chemotherapies are provided in Table 2.

TABLE 2

Major Adverse Effects of Cancer Chemotherapy.

| Major Adverse Health Effects | Antineoplastic Agent |
| --- | --- |
| Pancreatitis | VP-16, ara C |
| Alopecia | VP-16, Doxorubicin, Taxol, FU, araC |
| Cardiotoxicity | Taxol, Doxorubicin |
| Cutaneous | Doxorubicin |
| Diarrhea | CPT-11 |
| Dyspnea | ara C |
| Flush | Tamoxifen |
| Fever/Chills | VP-16, Doxorubicin |

TABLE 2-continued

Major Adverse Effects of Cancer Chemotherapy.

| Major Adverse Health Effects | Antineoplastic Agent |
|---|---|
| Hepatotoxicity | VP, Taxol, ara C, Methotrexate |
| Nephrotoxicity | Cisplatin |
| Ototoxicity | Cisplatin |
| Bone Marrow Hypolasia | Almost all anticancer drugs |

5-Fluorouracil: The fluoropyrimidine analog, 5-fluorouracil (5-FU or FU), exhibits a broad spectrum of clinical activity. It remains one of the most active agents in the treatment of colorectal cancer both in the adjuvant and advanced disease setting, and in other GI malignancies as well (Pinedo and Peters, 1988). In addition, this agent is active against cancers of the breast, and head and neck.

Recent advances in the therapy of colorectal cancer have used biochemical modulation to selectively activate specific pyrimidine metabolic pathways. The reduced folate, leucovorin (LV), is an effective biochemical modulator and has been used in clinical treatments in combination with FU (Peters and Van Groeningen, 1991; Joulia, et al., 1999). It has been shown that the addition of exogenous folate in the form of LV enhances responses to FU in clinical trials (Calabresi and Chabner, Page 1250, 1996). The purported mechanism of interaction of LV is enhanced thymidylate synthase inhibition.

The response rate to FU in patients with advanced disease is improved from 10%-12% (FU treatment alone) to 20%-30% (FU/LV treatment).

Capecitabine: Capecitabine (Xeloda®) is an oral medication used for the treatment of cancer. Capecitabine was approved by the FDA in 1998 for the treatment of metastatic breast cancers that are resistant to other medicines such as paclitaxel (Taxol®), doxorubicin, and adriamycin®. In 2001, it was approved by the FDA for the treatment of metastatic colorectal cancer, which is frequently treated with 5-FU. It generally is administered for 14 days, followed by a 7-day rest period during each 21-day cycle.

Capecitabine is a fluoropyrimidine carbamate with antineoplastic activity. The chemical name for capecitabine is 5'-deoxy-5-fluoro-N-[(pentyloxy)carbonyl]-cytidine. Capecitabine is described in U.S. Pat. No. 5,472,949, which is herein incorporated by reference in its entirety.

Capecitabine belongs to a group of chemotherapeutic agents known as antimetabolites. It is a prodrug of 5'-deoxy-5-fluorouridine (5'-DFUR) with an unique mechanism of activation. Capecitabine is converted to 5'-DFUR by either carboxyestelase or cytidine deaminase, which are localized in liver. 5'DFUR is converted to the active form of 5-FU by thymidine phosphorylase (dThdPase) in tumors. Capecitabine exploits the high concentrations of dThdPase in tumor tissue as compared to healthy tissue, leading to tumor-selective generation of 5-FU. 5-FU is further metabolized to two active metabolites, 5-fluoro-2-deoxyuridine monophosphate (FdUMP) and 5-fluorouridine triphosphate (FUTP), within normal and tumor cells. FdUMP inhibits DNA synthesis by reducing normal thymidine production, while FUTP inhibits RNA and protein synthesis by competing with uridine triphosphate. The active moiety of capecitabine, 5-FU, is cell cycle phase-specific (S-phase).

Studies have shown that capecitabine exhibits superior response as compared to 5-FU/LV which is administered intravenously (i.v.). In one study, patients treated with capecitabine achieved a significantly ($P=0.0014$) superior response rate of 21% compared with 11% with 5-FU/LV. The median times to disease progression with capecitabine and 5-FU/LV were 128 and 131 days, respectively (nonsignificant (NS)), and the median survival times were 380 and 407 days, respectively (NS) (Hoff et al. J Clin Oncol. 19:2282-2292, 2001). In another study, patients treated with capecitabine also achieved a significantly ($P=0.027$) superior response rate of 21% compared with 14% with 5-FU/LV. The median times to disease progression were 137 and 131 days, respectively (NS), and the median survival times were 404 and 369 days, respectively (NS) (Van Cutsem et al. J Clin Oncol. 19:4097-4106, 2001). Capecitabine also demonstrated an improved safety profile compared with i.v. 5-FU/LV.

Combination therapy using capecitabine and 5-FU/LV has shown survival benefit as compared to 5-FU/LV alone for the treatment of colorectal cancer. Other potential combination therapies with capecitabine for the treatment of colorectal cancer include but are not limited to capecitabine/oxaliplatin, capecitabine/irinotecan, capecitabine/oxliplatin/gefitimib, capecitabine/oxaliplatin/5-FU/LV, and capecitabine/radiation therapy. For breast cancer treatment, combination therapies include but are not limited to capecitabine/irinotecan, capecitabine/docetaxel (Taxotere®), capecitabine/paclitaxel, and capecitabine/5'-DFUR.

Like other chemotherapeutics, there are side effects associated with taking capecitabine. The most common side effects with capecitabine include diarrhea, nausea, vomiting, painful swelling of the mouth, fatigue, painful rash and swelling of the hands or feet, low white blood cell count (which can lead to infections), low blood platelet counts (which can lead to bleeding), and anemia. About one of every three patients who receives capecitabine has serious side effects, but these side effects usually are reversible when the drug is stopped or when the dose is lowered.

For a detailed description of the therapeutic uses of the fluoropyrimidine analogs, including 5-FU and capecitabine see, for example, Chabner et al., 1996.

CPT-11: Irinotecan (CPT-11) is a semi-synthetic camptothecin analogue that inhibits topoisomerase I in the replicating cell. It exhibits anti-tumor activity in cancer patients who fail first-line treatment with FU/LV (Bleiberg, 1999; Stucky-Marshall, 1999).

While CPT-11 is FDA-approved as a second-line therapy for patients with advanced colorectal cancer, the observed response rates are on the order of only 10%-15%.

The main side effects associated with this agent include leukopenia, anemia, nausea/vomiting, anorexia, and diarrhea. It is, therefore, desirable to develop a modulator agent that can either enhance the efficacy of the anti-tumor activity of CPT-11 and/or alleviate some of the toxic side effects associated with CPT-11 treatment so that the overall quality of life and performance status of the cancer patient is improved.

CPT-11/FU and CPT-11/FU/LV Combination: Colorectal cancer has been reported to be the second-leading cause of death from cancer in North America. The two drugs that are currently approved by the FDA for the treatment of colorectal cancer are irinotecan (CPT-11, Camptosar®) and 5-fluorouracil (FU). FU is an antimetabolite drug, which inhibits thymidylate synthase, an enzyme required for the synthesis of DNA. FU is commonly administered with LV, a reduced folate that increases the affinity of FU for thymidylate synthase, This therapy is currently used as first-line treatment for metastatic colon cancer (Murakami K, Sakukawa, R, Sano, M, et al., Clin Cancer Res. 5:2304-2310 (1999); van der Wilt C. L, van Groeningen, C. J, Pinedo H. M, et al., J. Cancer Res. Clin. Oncol. 123:595-601 (1997)). CPT-11 is a potent inhibitor of topoisomerase I, a nuclear enzyme involved in the unwinding of DNA during replication. CPT-11 has demonstrated antitumor activity against metastatic colorectal cancer as second-line treatment after the failure of FU (Kase, Y, Hayakawa, T, Togashi, Y, et al., Jpn J Pharmacol, 75:399-405 (1997); Araki E, Ishikawa M, Iigo M, et al., Jpn J Cancer Res 84:697-702 (1993); Bissery M C, Vrignaud P, Lavelle F, et al., Anti-Cancer Drugs 7:437-460 (1996); Saltz L. B, Cox J. V, Blanke C, et al., New. Eng. J. Med. 343:905-914 (2000)). Recently, FDA approved the triple combination use of CPT-11/FU/LV as the firstline treatment for advanced colorectal cancer. Unfortunately, severe diarrhea has been identified as one of the dose-limiting toxicities among patients treated with this combination therapy (Saltz L. B, Cox J. V, Blanke C, et al., New. Eng. J. Med. 343:905-914 (2000); Murakami K, Sakukawa, R, Sano, M, et al., Clin Cancer Res. 5:2304-2310 (1999); van der Wilt C. L, van Groeningen, C. J, Pinedo H. M, et al., J. Cancer Res. Clin. Oncol., 123:595-601 (1997).

VP-16 (etoposide): VP-16, also known as etoposide, shows significant clinical activity against small-cell lung cancer, testicular cancer, lymphoma and leukemia (O'Dwyer, P., et al., Etoposide (VP-16-213), Current Status of an Active Anticancer Drug, New Engl. J. Med. 312:692-700 (1985)) and include neoplasms seen in Hodgkin's disease, Papillomavirus and diffuse histiocytic lymphoma.

It is believed that etoposide blocks the catalytic activity of DNA topoisomerase II by stabilizing an enzyme-DNA complex in which the DNA is cleaved and covalently linked to the enzyme. See Chen, G. L., Yang, L., Rowe T. C., Halligan, B. D., Tewey, K., and Liu, L., *J. Biol. Chem.*, 259:13560 (1984); Ross, W., Rowe, T., Glisson, B., Yalowich, J., and Liu, L., *Cancer Res.*, 44:5857 (1984); Rowe, T., Kuppfer, G., and Ross, W., Biochem. Pharmacol., 34:2483 (1985), which are all herein specifically incorporated by reference.

By way of background, topoisomerases are enzymes which control the topological state of DNA. Type II topoisomerases catalyze DNA strand passage through transient double strand breaks in the DNA. The resulting change in the linking number of DNA allows these enzymes to mediate DNA interconversions, such as supercoiling and relaxation of supercoiling, catenation and decatenation, knotting, and unknotting. See Wang, J. C., Annu. Rev. Biochem., 54:665 (1985) and Maxwell, A., and Gellert, M., Adv. Protein Chem., 38:69 (1986), which are herein specifically incorporated by reference.

Type II DNA topoisomerase enzymes have been shown to be involved in a number of vital cellular processes, including DNA replication and transcription, and chromosomal segregation. These enzymes, therefore, are a critical target for the action of a wide variety of anticancer drugs, including etoposide and teniposide. The key step leading to cell death may be the capability of these drugs to block the catalytic activity of DNA topoisomerase II, as noted above.

Beta-L-Dioxolane-Cytidine (L-OddC): Beta-L-dioxolane-cytidine [L-OddC] is the first nucleoside analogue with the unnatural L configuration shown to have anticancer activity (Grove et al., Cancer Res (1996) 56(18):4187-4191). This compound has been shown to have a potent antitumor activity in human prostate and hepatocellular xenograft tumor models (Grove et al., Cancer Res (1995) 55:3008-3011). Further, L-OddC has been shown to be effective against hyperproliferative activity in human keratinocytes in vitro (Schwartz et al., Skin Pharmacol Appl Skin Physiol (1998) 11(4-5):207-213).

This compound works by rapid translocation into cells by both equilibrative-sensitive and -insensitive nucleoside transport systems where it is incorporated into DNA of cells. DNA incorporation leads to degradation of DNA into large fragments without generation of internucleosomal laddering.

Gemcitabine: Gemcitabine (Gemzar®) was approved by the FDA in 1996 for the treatment of locally advanced or metastatic pancreatic cancer, either as initial therapy or following treatment with the chemotherapy agent fluorouracil. It also has been approved for the treatment of locally advanced or metastatic non-small cell lung cancer, in combination with the chemotherapy agent cisplatin (Platinol®). Gemcitabine is administered intravenously (i.v.) and the dose depends on several factors, including the condition being treated, the size of the patient, the particular treatment regimen being used, and the overall health of the patient.

Gemcitabine is the generic name assigned to 2'-deoxy-2', 2'-difluoro-cytidine. It is also known chemically as 1-(4-amino-2-oxo-1H-pyrimidin-1-yl)-2-desoxy-2,2-difluororibose. Gemcitabine is disclosed in U.S. Pat. Nos. 4,808,614 and 5,464,826, which are incorporated herein by reference for their teaching of how to synthesize, formulate, and use gemcitabine for treating susceptible neoplasms. Gemcitabine is commercially available as the monohydrochloride salt, and as the β-isomer.

Gemcitabine belongs to a group of drugs called antimetabolites. Generally, antimetabolites produce their anti-cancer effects by inhibiting the ability of a cell to produce or repair DNA, thereby making the cell unable to replicate or repair itself and ultimately causing cellular death. Gemcitabine exhibits cell phase specificity, primarily killing cells undergoing DNA synthesis (S-phase) and also blocking the progression of cells through the G1/S-phase boundary. Gemcitabine is metabolized intracellularly by nucleoside kinases to the active diphosphate (dFdCDP) and triphosphate (dFdCTP) nucleosides. The cytotoxic effect of gemcitabine is attributed to a combination of two actions of the diphosphate and the triphosphate nucleosides, which leads to inhibition of DNA synthesis. First, gemcitabine diphosphate inhibits ribonucleotide reductase, which is responsible for catalyzing the reactions that generate the deoxynucleoside triphosphates for DNA synthesis. Inhibition of this enzyme by the diphosphate nucleoside causes a reduction in the concentrations of deoxynucleotides, including dCTP. Second, gemcitabine triphosphate competes with dCTP for incorporation into the DNA. The reduction in the intracellular concentration of dCTP (by the action of the diphosphate) enhances the incorporation of gemcitabine triphosphate into the DNA (self-potentiation). After the gemcitabine nucleotide is incorporated into the DNA, only one additional nucleotide is incorporated into the DNA. After this addition, there is inhibition of further DNA synthesis.

Like other chemotherapeutic agents, gemcitabine causes unwanted side effects. The more common side effects of using gemcitabine include but not limited to decreased white blood cell count with increased risk of infection, decreased platelet count with increased risk of bleeding, nausea, vomiting, increased liver function blood tests, and fatigue. The less common side effects are diarrhea; sores in mouth or on lips; flu-like symptoms; skin rash; swelling of hands, ankles, and face; hair thinning; and itching.

Oxaliplatin: Oxaliplatin (Eloxatin®) was approved in August 2002 by the FDA for second-line treatment of patients with metastatic carcinoma of the colon and rectum. In February 2005, it was approved for first-line treatment of advanced colorectal cancer. This recent approval recommends use of oxaliplatin in combination with 5-fluorouracil and leucovorin (5-FU/LV). Oxaliplatin is administered intravenously, and the dose depends on several factors, including the condition being treated, the size of the patient, the particular regimen being used and the overall health of the patient.

Oxaliplatin is a diaminocyclohexane compound that is known to cause DNA damage of the same sites of adduct formation as does cisplatin. It is also known as L-OHP and is a third generation platinum complex. The chemical name of oxaliplatin as cis-oxalato(trans-1-1,2-cyclohexane-diamine) platinum (II). Oxaliplatin is described in U.S. Pat. No. 4,169,846 and in related patents U.S. Pat. No. 5,290,961; U.S. Pat. No. 5,298,642; U.S. Pat. No. 5,338,874; U.S. Pat. No. 5,420,319 and PCT/IB/00614, which are herein incorporated by reference in their entirety.

The term "oxaliplatin" as used herein, includes cis-oxalato (trans-1-1,2-diaminocyclohexane)platinum(II), its optic enatiomer cis-oxalato(trans-d-1,2-diaminocyclohexane)platinum(II) and any racemic mixture thereof. The term "oxaliplatin" also includes cis-oxalato (trans-1-1,2-diaminocyclohexane) platinum (II) having high optical purity, namely an optical purity equal to or higher than about 99.5%, for example a cis-oxalato (trans-1-1,2-diaminocyclohexane) platinum(II), wherein the melting point is between about 198° C. and about 292° C., obtained following the procedure described in U.S. Pat. No. 5,338,874 (which is incorporated by reference in its entirety) and, especially, a cis-oxalato (trans-1-1,2-cyclohexanediamine)platinum(II), which possesses optical purity of about 99.94% or more and a melting point between about 198.3° C. and about 199.7° C., obtained following the procedure disclosed in U.S. Pat. No. 5,420,319, which is incorporated by reference in its entirety. Derivatives of oxaliplatin include, but are not limited to, carboplatin and cisplatin.

Oxaliplatin belongs to a new class of platinum agent. It contains a platinum atom complexed with oxalate and diaminocyclohexane (DACH). The bulky DACH is thought to contribute greater cytotoxicity than cisplatin and carboplatin (Wiseman et al., Drugs Aging 1999;14(6):459-75). The exact mechanism of action of oxaliplatin is not known. Oxaliplatin forms reactive platinum complexes which are believed to inhibit DNA synthesis by forming interstrand and intrastrand cross-linking of DNA molecules. Oxaliplatin is not generally cross-resistant to cisplatin or carboplatin, possibly due to the DACH group and resistance to DNA mismatch repair (Wiseman et al., Drugs Aging 1999, 14(6):459-75; Misset et al., Critical Reviews in Oncology-Hematology 2000, 35(2):75-93). Preclinical studies have shown oxaliplatin to be synergistic with fluorouracil and SN-38, the active metabolite of irinotecan (Cvitkovic et al., Semin Oncol 1999, 26(6):647-62). Oxaliplatin is a radiation-sensitizing agent (Freyer et al., Proc Am Soc Clin Oncol 2000, 19:260a; Carraro et al., Proc Am Soc Clin Oncol 2000,19:291a). It is cell-cycle-phase nonspecific (Sanofi-Synthelabo. Eloxatin: Summary of product characteristics (Europe): France; 1 Oct. 1999).

Like other chemotherapeutic agents, there are side effects with the use of oxaliplatin. The more common side effects include nausea, vomiting, numbness and tingling in hands and/or feet due to nerve irritation, numbness of lips, diarrhea, abdominal pain, mouth sores, difficulty breathing, and fatigue. The less common side effects include difficulty walking, decreased white blood cell count with increased risk of infection, decreased platelet count with increased risk of bleeding, difficulty swallowing or breathing, poor tolerance to cold temperatures, and allergic reaction with rash, itching, swelling lips or tongue, or sudden cough.

Thalidomide: Thalidomide, a derivative of glutamic acid, was first prescribed as an antiemetic drug in 1950s. Unfortunately, it was found that thalidomide had teratogenic effects in developing fetuses. Consequently, thalidomide was hauled from the market. In recent years, thalidomide has been investigated in other areas of medicine. It was found that thalidomide significantly decreased the formation of new vessels and inhibited vascular endothelial growth factor (VEGF)-induced angiogenesis, an important progression of haematological malignancies. Several clinical trials implied that thalidomide might also possess antineoplastic properties.

Thalidomide exists in two isomeric forms which are designated as right-handed and left-handed. These two isomers spontaneously interchange forming a racemic mixture. Thalidomide derived analogs include the Immunomodulatory Drugs (IMiDs) and SelCIDs (Selective Cytokine Inhibitory Drugs). Examples of IMiDs include but are not limited to CC-4047 and CC-5013. Examples of SelCIDs include but are not limited to CC-7034 and CC-9088. Other derivatives of thalidomide include but are not limited to lenalidomide, α-EM12, β-EM12, and phthalimidophthalimide.

In recent years, thalidomide has been found to have some effect in the treatment of various diseases such as but not limited to AIDS, leprosy, rheumatoid arthritis, and cancer. Specifically, in HIV patients, thalidomide has been helpful in reducing the effects of cashexia (progressive loss of body and muscle mass) and in treating aphothous ulcers (growth of sores in mouth and throat). Thalidomide is also effective in stopping HIV replication. Thalidomide has also been shown to have anti-inflammatory and immunosuppressant qualities which makes it potentially effective in the treatment of Behcet's disease, sarcoidosis, scleroderma, and Crohn's disease.

Moreover, thalidomide has been established as an effective therapy for the treatment of radvanced relapsed and refractory multiple myeloma (MM) (Singhal et al. 1999 N. Engl. J. Med. 341:1565-1571). Studies have demonstrated that both thalidomide and IMiDs not only act to inhibit angiogenesis, but also act directly to induce both apoptosis and growth arrest in resistant myeloma cells. They also block both the adhesion of myeloma cells to bone marrow stromal cells and the related protection against apoptosis, and block the increased secretion of myeloma cell growth, survival, and migratory factors such as interleukin-6, tumor necrosis factor alpha (TNF-α), and vascular endothelial growth factor, triggered by the binding of myeloma cells to bone marrow stromal cells. In addition, they expand natural killer cell and T-cell numbers, and improve function against human myeloma cells and enhance their susceptibility to antibody-dependent cell-mediated cytotoxicity in vivo. (See for example, Anderson et al. 2001 Semin Hematol 38:6-10; Hideshima et al. 2000 Blood 96:2943-2950; Gupta et al 2001 Leukemia 15:1950-1961; Davies et al. 2001 Blood 98:210-216; Treon et al. 2001 J Immunother 24:236-271; Lentzsch et al. 2003 Leukemia 17:41-44). However, the efficacy of thalidomide, however, has been significantly limited by adverse effects, which include sedation, neuropathy, constipation, and deep vein thrombosis).

Doxorubicin: Doxorubicin (Adriamycin, DOX, ADM) is an anthracycline antibiotic produced by the fungus *streptomyces peucetius* and has been approved for the therapy of various cancers. Doxorubicin is the inhibitor of DNA topoisomerase II; it damages DNA by the intercalation of the anthracycline portion, metal ion chelation or by the generation of free radicals. Although there is no FDA-approved chemotherapeutic agent available for the treatment of hepatocellular carcinoma, doxorubicin has been used a current "standard" chemotherapy. A response rate of 16% (range 0-35%) was reported in eight trials that included 475 evaluable patients (Engstrom P F et al., (1993) in Cancer Medicine Holland J F, Frei E (eds) pp. 1430-1441. London:Lea and Febiger).

Quality of Life (QOL): Standard evaluation measures for the success of cancer treatments include, but are not limited to, changes in tumor mass and type as well as the rate and amount of tumor spreading (both locally to and distant to the tumor(s) being evaluated). One skilled in the art of chemotherapy evaluations can also determine whether a particular treatment appears to enhance a patient's life expectancy and quality of life (even for those patients not responding to the usual treatments). For example, effective treatment of gastrointestinal diseases may be determined by several criteria, including, but not limited to, an enteritis score (based upon a composite score of clinical symptoms such as abdominal pain, cramping, stool guaiac and diarrhea), as well as related endpoints such as percent chemotherapy dose delivered, days of hospitalization, transfusions, intravenous fluid therapy, antimotility agents, and ability to eat.

With respect to a treatment effect, the subjective symptoms of the patient do not always coincide with the result of the test conducted by the doctor. For example, even in the case where an unfavorable test result is obtained, when the occurrence of urinary incontinence and voiding are reduced, the patient believes the treatment has worked, with the result that the quality of life (QOL) is improved. During chemotherapy the negative side effects in the life of the patients, such as hair loss, reduction in weight, loss of appetite, fatigue, diarrhea, nausea, vomiting, etc. can be persistent and result in chronic torment, night and day, that can be unbearable to the patients, both physically and mentally. Thus, therapeutic effectiveness of methods of the present invention is meant to refer not only to partial or entire relief from the pain or reduction in tumor growth or cancer regression, but relief as a consequence of reduced or eliminated side-effects traditionally associated with treatment, with the overall result being an enhanced quality of life.

Baseline evaluations can be entered as part of the treatment protocol whereby various criteria are measured and correlated with QOL. Further, patients can report on a patient diary events such as feeling "fair" or experiencing "moderate" pain. These measures are then used during and after treatment to evaluate whether the patient feels that the quality of life has improved.

2. Chemotherapy of Parasitic Infections

Parasitic protozoa are responsible for a wide variety of infections in man and animals, and many diseases caused by parasitic protozoa are life threatening to the host. For example, malaria remains a significant health threat to humans despite massive international attempts to eradicate the disease; trypanosomiasis such as Chagas disease caused by *Trypanosoma cruzi* and African sleeping sickness caused by *T. brucei* are not uncommon in Africa and South America; and opportunistic infections in immunocompromised hosts caused by *Pneumocystis carinii*, *Toxoplasma gondii*, *Cryptosporidium* spp. are becoming increasingly significant in the developed countries.

In some protozoal diseases, such as Chagas disease, there is no satisfactory treatment; in others, drug-resistant strains of the protozoa may develop. Accordingly, there exists a continued need to identify new and effective anti-protozoal drugs. However, antiparasitic drug discovery has been, for the most part, a random and laborious process through biological screening of natural products and synthetic compounds against a panel of parasites.

Despite encouraging progress in vaccine development, chemotherapy remains the single most effective, efficient, and inexpensive means to control most parasitic infections (Tracy and Webster, Chemotherapy of Parasitic Infections, in Goodman & Gilman's The Pharmacological Basis of Therapeutics, Ninth Edition, pages 955-985, 1996). Drugs available now are especially effective in treating human infections caused by flukes and intestinal parasites. But new or better pharmaceuticals are urgently required, both to combat such systemic infections as cysticercosis, filariasis, leishmaniasis, trichinosis, and trypanosomiasis and to counteract development of drug resistance manifested especially by malaria and other protozoan parasites. Protozoan parasites develop resistance to drugs far more readily than do helminths, consistent with their more rapid proliferation in the host.

It is essential that antiparasitic drugs be safe and effective in patients. The therapeutic efficacy of antiparasitic drugs are complex and are dependent upon the host, the parasite, and the environmental factors. Thus, the best drugs and optimal dose regimens are often determined by trial and error rather than from careful pharmacokinetics and pharmacodynamic studies of patients with endemic infections. For proper evaluation, population-based chemotherapy should be instituted only after appropriate epidemiological studies divulge patterns of transmission and the relationship of age-specific prevalence and intensity of infection to disease. For optimal results, chemotherapy should be combined with other public health measures appropriate for the particular infection, environment and host population. The ideal agent for mass chemotherapy would have a broad spectrum of activity against all developmental stages of infecting parasites. It also would be safe at high therapeutic doses taken orally for one day only; be chemically stable under conditions of use; be effective as an inducer of drug resistance; and be inexpensive. At present, few available antiparasitic drugs meet these criteria.

Chemotherapeutic agents that are effective against asexual erythrocytic malarial parasites include chloroquine, quinine, quinidine, mefloquine, and halofantrine. Other drugs such as pyrimethamine, sulfonamides, sulfones, and tetracyclines, are slower acting and less effective than the above agents, and therefore are usually used in combination with other chemotherapeutic agents. Agents such as atovaquone, chloroquine, diloxanide furoate, eflornithine, emetine and dehydroemetine, 8-hydroxyquinolines, melarsoprol, metronidazole, nifurtimox, pentamidine, quinacrine, sodium stibogluconate, and suramin are effective in treating parasitic infections including trypanosomiasis, leishmaniasis, amebiasis, giardiasis, and trichomoniasis. Lastly, infections with parasitic worms, helminthiasis, are usually treated with anthelmintic drugs such as benzimidazole, diethylcarbamazine, ivermectin, metrifonate, niclosamide, oxanmiquine, piperazine, praziquantel, and pyrantel pamoate. For a review of drugs for chemotherapy of parasitic infections, see Tracy and Webster, Id.

3. Chemotherapy of Microbial Diseases

In 1936, favorable clinical results using sulfanilamide in puerperal sepsis and meningococcal infections reported by Colebrook and Kenny and Buttle and coworkers awakened the medical profession to the new field of antibacterial chemotherapy. In 1941, penicillin was mass produced and first made available for limited clinical trial. At present, at least 30% of all hospitalized patients receive one or more courses of therapy with antibiotics, and millions of potentially fatal infections have been cured.

Antibiotics are substances produced by various species of microorganisms (bacteria, fungi, actinomycetes) that suppress the growth of other microorganisms and eventually may destroy them. However, common usage extends the term to include synthetic bacterial agents, such as sulfonamides and quinolones, which are not products of microbes. Antibiotics differ in physical, chemical, and pharmacological properties; antibacterial spectra; and mechanisms of action.

The most common classification of antimicrobial agents which is based on chemical structure and proposed mechanism of action is the following: (1) agents that inhibit synthesis of bacterial cell walls; for example, the penicillins and cephalospoins, which are structurally similar, and dissimilar agents such as cycloserine, vancomycin, bacitracin, and the imidazole antifungal agents such as miconazole, ketoconazole, and clotrimazole; (2) agents that act directly on the cell membrane of the microorganism, affecting permeability and leading to leakage of intracellular compounds; these include the detergents, polymyxin and colistimethate, and the polyene antifungal agents, that bind to cell-wall sterols; (3) agents that affect the function of 30S or 50S ribosomal subunits to cause a reversible inhibition of protein synthesis; these bacteriostatic drugs include chloramphenicol, the tetracyclines, erythromycin, and clindamycin; (4) agents that bind to the 30 S ribosomal subunit and alter protein synthesis, which eventually leads to cell death; these include the aminoglycosides; (5) agents that affect nucleic acid metabolism, such as the rifamycins (e.g., rifampin), which inhibit DNA-dependent RNA polymerase, and the quinolones, which inhibit gyrase; (6) the antimetabolites, including trimethoprim and the sulfonamides, which block specific metabolic steps that are essential to microorganisms; (7) nucleic acid analogs, such as zidovudine, ganciclovir, vidarabine, and acyclovir, which inhibit viral enzymes that are essential for DNA synthesis, thus halting viral replication. (See, Chambers and Sande, Section IX Chemotherapy of Microbial Diseases: Antimicrobial Agents, in Goodman & Gilman's The Pharmacological Basis of Therapeutics, Ninth Edition, page 1029, 1996.)

Whether an antibiotic is effective in treating an infection depends on several factors. In order for an antibiotic to be effective, a sufficient concentration of the antibiotic must be achieved at the site of infection to inhibit bacterial growth. However, the concentration of the drug must remain below those that are toxic to human cells. If the concentration of antibiotic required to inhibit or kill the microorganism is greater than the concentration that can be safely achieved, the microorganism is considered to be resistant to the antibiotic. Bacteria can be resistant to an antimicrobial agent because the agent fails to reach its target, the agent is inactivated, or the target is altered. Some bacteria produce enzymes that reside at or within the cell surface and inactivate the drug. Others possess impermeable cell membranes that prevent the influx of the drug. Some bacteria are deficient in aqueous channels made up of porins that hydrophilic agents use to traverse the outer membrane of bacteria, while others lack the transport system that is required for entrance of the drug into the bacterial cell. The emergence of antibiotic resistant pathogens has led to an ever-increasing need for new drugs and new methods of treating antimicrobial diseases.

B. Antiviral Therapy

1. Viruses and Viral Diseases

A virus is a microorganism that cannot reproduce by itself. However, upon infection of a host cell, the virus utilizes the metabolic machinery of the host cell to produce more viral material. Viral infection and replication in host cells generally results in disease, whether the host is an animal or plant. Human diseases caused by viral infections include, for example, the acquired immunodeficiency syndrome (AIDS) and hepatitis. A general discussion of this field is presented in Fundamental Virology, Second Edition, (ed. B. N. Fields, D. M. Knipe, R. M. Chanock, M. S. Hirsh, J. L. Melnick, T. P. Monath, and B. Roizman, Raven Press, Ltd., New York, N.Y. 1991). Examples of a few viruses and the diseases that they cause are discussed below.

Retroviruses: Retroviruses comprise a large family of viruses that primarily infect vertebrates. Many diseases, including the induction of some tumors, are associated with retroviral infection (see Fundamental Virology, supra, pp. 645-708). Retroviruses contain an RNA genome that is replicated through a DNA intermediate. Early in the retroviral life cycle, the RNA genome is copied into DNA by the virally encoded reverse transcriptase (RT). This enzyme can use both RNA and DNA templates, thereby producing the first strand of DNA (the negative strand) from the infecting RNA genome and a complementary second strand (the positive strand) of DNA using the first DNA strand as a template. To synthesize these DNA strands, the RT utilizes cellular substrates called deoxynucleoside triphosphates (dNTP).

Human retroviruses can be grouped into the leukemia viruses (HTLV type viruses) and the immunodeficiency viruses (HIV type viruses). HTLV infection may lead to one form of leukemia. HIV infection causes acquired immunodeficiency syndrome (AIDS). There are two related human immunodeficiency viruses, HIV-1 and HIV-2. HIV-1 is more virulent than HIV-2. Both HTLV and HIV infect peripheral blood lymphocytes (PBL).

Other animal retroviruses include feline leukemia virus (FeLV) and lentiviruses. Virulent FeLV infection generally results in fatal aplastic anemia in cats. Lentiviruses cause a variety of neurological and immunological diseases such as visna in sheep and infectious anemia in horses.

Several other viruses that infect humans, animals, and plants also depend on reverse transcriptase for replication. These include retroviruses such as the leukemia viruses known to exist in several species, including HTLV-1 in humans, as well as reverse transcriptase dependent DNA viruses, such as the cauliflower mosaic virus (a plant virus).

Viral Hepatitis: Hepatitis is a disease of the human liver. It is manifested with inflammation of the liver and is usually caused by viral infections and sometimes from toxic agents. Hepatitis may progress to liver cirrhosis, liver cancer, and eventually death. Several viruses such as hepatitis A, B, C, D, E and G are known to cause various types of viral hepatitis. Among them, HBV and HCV are the most serious.

Hepatitis B is caused by a DNA virus. It has a long incubation period of 50-160 days. It is usually transmitted by injection of infected blood or blood derivatives or by use of contaminated needles, lancets, or other instruments. Hepatitis B virus infection leads to a wide spectum of liver injury. Moreover, chronic hepatitis B infection has been linked to the subsequent development of hepatocellular carcinoma, a major cause of death.

Hepatitis C is caused by an RNA virus. The incubation period of 6-8 weeks with about 75% of infections subclinical and giving rise to chronic persistent infection. A high percentage develop chronic liver disease leading to cirrhosis and possible heptocellular carcinoma. Hepatitis C is difficult to treat and it is estimated that there are 500 million people infected with it worldwide (about 15 time those infected with HIV).

Herpesviruses: Herpesviruses isolated from humans include, but are not limited to, herpes simplex virus 1 ("HSV-1"), herpes simplex virus 2 ("HSV-2"), human cytomegalovirus ("HCMV"), varicella-zoster virus ("VZV"), Epstein-Barr virus ("EBV"), human herpesvirus 6 ("HHV6"), herpes simplex virus 7 ("HSV-7"), herpes simplex virus 8 ("HSV-8"). Herpesviruses have also been isolated from horses, cattle, pigs (pseudorabies virus ("PSV") and porcine cytomegalovirus), chickens (infectious larygotracheitis), chimpanzees, birds (Marck's disease herpesvirus 1 and 2), turkeys and fish (see "Herpesviridae: A Brief Introduction", Virology, Second Edition, edited by B. N. Fields, Chapter 64, 1787 (1990)).

Herpes simplex viral ("HSV") infection is generally a recurrent viral infection characterized by the appearance on the skin or mucous membranes of single or multiple clusters of small vesicles, filled with clear fluid, on slightly raised inflammatory bases.

The herpes simplex virus is a relatively large-sized virus. HSV-2 commonly causes herpes labialis. HSV-2 is usually, though not always, recoverable from genital lesions. Ordinarily, HSV-2 is transmitted venereally.

Diseases caused by varicella-zoster virus (human herpesvirus 3) include varicella (chickenpox) and zoster (shingles). Cytomegalovirus (human herpesvirus 5) is responsible for cytomegalic inclusion disease in infants. Epstein-Barr virus (human herpesvirus 4) is the causative agent of infectious mononucleosis and has been associated with Burkitt's lymphoma and nasopharyngeal carcinoma. Animal herpesviruses which may pose a problem for humans include B virus (herpesvirus of Old World Monkeys) and Marmoset herpesvirus (herpesvirus of New World Monkeys).

2. Antiviral Agents

Antiviral Agents include drugs such as acyclovir (ACV) which treats genital herpes to drugs that treat AIDS, for example, zidovudine (AZT) and dideoxyinosine (DDI). Examples of a few antiviral agents are discussed below.

Over the years, anti-retroviral drugs have been developed for the treatment of AIDS. Anti-retroviral drugs include, for example, Abacavir (ABC), Adefovir (ADV), Amprenavir (APV), Zidovudine (AZT), Didanosine (ddI), Zalcitabine (ddC), Stavudine (d4T), Efavirenz (EFV), Lamivudine (3TC), Saquinavir (SQV), Indinavir (IDV), Ritonavir (RTV), Delavirdine (DLV), Nelfinavir (NFV), Nevirapine (NVP). However, attempts to treat AIDS with anti-viral drugs have not been met with a desirable degree of success. Despite the high efficacy of some of the antiviral drugs, the initial in vitro/in vivo testing has been characterized by the rapid onset of variants of HIV-1 resistant to these drugs. Additionally, there is a potential for toxicity with the use of anti-viral drugs. There is a need for an effective and safe means to treat AIDS.

No local or systemic chemotherapeutic agent has been demonstrated to be effective for treating herpes simplex virus with the possible exception of topical idoxuridine (IDU) in superficial herpetic keratitis. Reports on this compound in cutaneous herpes are conflicting. Other drugs which have been employed to treat HSV include trifluorothymidine, vidarabine (adenine arabinoside, ara-A), acyclovir, and other inhibitors of viral DNA synthesis may be effective in herpetic keratitis. These drugs inhibit herpes simplex virus replication and may suppress clinical manifestations. However, the herpes simplex virus remains latent in the sensory ganglia, and the rate of relapse is similar in drug-treated and untreated individuals. Moreover, some drug-resistant herpes virus strains have emerged. Accordingly, there is also a need to develop more effective means to treat diseases associated with herpes simplex virus.

Current prevention of hepatitis B virus (HBV) infection is a hepatitis B vaccination which is safe and effective. However vaccination is not effective in treating those already infected (i.e., carriers and patients). Many drugs have been used in treating chronic hepatitis B and none have been proven to be effective, except interferon No effective immunization is currently available for hepatitis C, and hepatitis C can only be controlled by other preventive measures such as improvement in hygiene and sanitary conditions and interrupting the route of transmission. At present, the only acceptable treatment for chronic hepatitis C is interferon which requires at least six (6) months of treatment and or ribavarin which can inhibit viral replication in infected cells and also improve liver function in some people. Treatment with interferon with or without Ribavarin however has limited long term efficacy with a response rate about 25%.

C. PHY906

Introduction: PHY906 is a traditional Chinese botanical formulation composed of four herbs each of which is selected from one of four herb groups. The four herb groups are commonly known as *Scutellaria*, sometimes known as Scute, Licorice, Peony Alba and Ziziphi Fruit (Table 3). Thus, one plant species is chosen from each one of the four plant groups provided in Table 3 in order to produce the desired herbal compositions of the present invention. While particular combinations of the listed plant species are provided as examples of preferred PHY906 formulations, the compositions and methods of this invention encompass any combination of four plant species wherein a plant species is selected from each one of the four groups in Table 3. This invention encompasses any such combination of such herbs which have at least one of the biological activities or desired effects ascribed to PHY906 as described herein.

TABLE 3

Examples of Particular Species of Four Genera Which Can be Used to Make PHY906.
Common English Name of TCM Herbal Group

| Scutellaria | Licorice | Peony Alba | Ziziphi Fruit |
|---|---|---|---|
| *Anemone rivularis* Buch.-Ham. ex DC. | *Abrus mollis* Hance | *Paeonia delavayi* Franch. var. lutea (Delavay ex Franch.) Finet et Gagnep. | *Ziziphus jujuba* Mill. |
| *Thalictrum omelense* W. T. Wang et S. H. Wang | *Glycyrrhiza aspera* Pall. | *Paeonia lactiflora* Pall. | *Ziziphus jujuba* Mill. var. inermis |
| *Mahonia bealei* (Fort.) Carr. | *Glycyrrhiza eurycarpa* P. C. Li | *Paeonia mairei* Levi. | |
| *Nandina domestica* Thunb. | *Glycyrrhiza glabra* L. | *Paeonia obovata* Maxim. var. willmottiae (Stapi) Stern | |
| *Scutellaria amoena* C. H. Wright | *Glycyrrhiza inflata* Bat. | *Daphne papyracea* Wall. ex Steud. | |

TABLE 3-continued

Examples of Particular Species of Four Genera Which Can be Used to Make PHY906.
Common English Name of TCM Herbal Group

| Scutellaria | Licorice | Peony Alba | Ziziphi Fruit |
|---|---|---|---|
| Scutellaria amoena C. H. Wright var. cinerea Hand.-Mazz. | Glycyrrhiza squamulosa Franch. | Cynanchum otophyllum Schneid. | |
| Scutellaria baicalensis Georgi | Glycyrrhiza uralensis Fisch. | Codonopsis lanceolara Sieb. et Zucc. Trautv. | |
| Scutellaria baicalensis Georgi var. albiflora K. Onuma | Phlomis betonicoides Diels | | |
| Scutellaria chungtienensis C. Y. Wu | | | |
| Scutellaria hypericifolia Levl | | | |
| Scutellaria likiangensia Diels | | | |
| Scutellaria obtusifolia Hemsl. var. trinervata (Vant.) C. Y. Wu et H. W. Li | | | |
| Scutellaria regeliana Nakai | | | |
| Scutellaria regeliana Nakai var. ikonnikovii (Juz.) C. Y. Wu et H. W. Li | | | |
| Scutellaria rehderiana Diels | | | |
| Scutellaria tenax W. W. Smith var. patentipilosa (Hand. -Marz.) C. Y. Wu | | | |
| Scutellaria viscidula Bunge | | | |

This herbal formula has been long used in Asia to treat a variety of ailments such as cardiac distention, abdominal spasms, fever, headache, vomiting, retching, thirst and mucous-like stool (Hani Oka and Taki No, 1998). A preferred formulation of PHY906 is provided in Table 4.

TABLE 4

Herbal Ingredients of TCM Formula PHY906

| Scientific Name | Percentage | Common Name | Traditional Use |
|---|---|---|---|
| Scutellaria baicalensis | 33.3 | Scute Baical Skullcap Root | Used to reduce capillary permeability; to reduce inflammation: to treat enteritis and dysentery; increase the secretion of bile to treat jaundice; to relieve muscle spasms to treat coughing; to expel parasites. |
| Glycyrrhiza uralensis | 22.2 | Licorice Root | Used to moisten the lungs and stop coughs; to relax spasm and stop pain; to moderate the action of herbs: to reduce fire and release toxins. |
| Ziziphus jujuba | 22.2 | Date | Has diuretic and strengthening effects |
| Paeonia lactiflora | 22.2 | White Peony Root | Used to suppress and soothe pain: to soothe ligaments and purify the blood |

An alternative formulation of PHY906 has the herbs *Scutellaria, Glycyrrhiza, Ziziphus,* and *Paeonia* in the following relative proportions: 4/14:3/14:4/14:3/14, respectively.

While specific ratios of the herbs of PHY906 are provided as examples, the compositions and methods of this invention encompass any ratios of the four herbal components which have the desired biological activity as described herein.

Currently, both gelatin capsules and granule pouches of PHY906 are produced by Sun Ten Laboratories, Inc., in Irvine, Calif. (a sister company of Sun Ten Pharmaceutical Co. Ltd. in Taiwan) using the formulation provided in Table 4. This formulation of PHY906 has been distributed and sold as a dietary supplement since 1983 by Brion Herbs Corporation (12020 B Centralia Road, Hawaiian Garden, Calif., 90716).

Production: A brief review of a process which can be used for producing PHY906 is provided. First, the proper ratios of the ingredients of the herbal raw materials are placed in a jacketed reactor and extracted with water at an elevated constant temperature with mixing. The ratios are set forth in the Manufacturing Instruction reproduced from Master Formula Record. The solid materials are then separated from the liquid with a 120-mesh screen. The filtrate is collected and then concentrated by evaporating the water under reduced pressure. The concentrated liquor is spray dried at an elevated temperature to yield dry powder which is then processed to yield granulated powder. This bulk substance is then formulated into the desired dosage form.

Process controls are utilized to ensure the uniformity and integrity of the product. Such process controls include, but are not limited to, checking the volume of the process liquor, HPLC determinations to establish Chemical Fingerprintings to verify identity of the raw materials, and inspections and tests of intermediate and final products. Accepted Quality Level (AQL) Limits are established for each conducted analysis and for each step of the manufacturing and control of production.

All of the components used in the production process are assigned a specific lot number in the Production Instruction Record. Quality control records are reviewed before a batch is released.

Purified marker substances are used for identification and quality control of the raw materials as well as the herbal substances. Table 5 lists the marker substances of each raw material used in the preparation of PHY906 herbal substance.

TABLE 5

Marker Substances for Herbal Ingredients of PHY906

| Herb | Origin of Herb Producing Place | Marker Substance |
|---|---|---|
| *Scutellaria baicalensis* Georgi. | Shang Xi Province, China | Baicalin |
| *Glycyrrhiza uralensis* Fisch. | Inner Mongolia, China | Glycyrrhizin |
| *Ziziphus jujuba* Mill. | Hebei/Shangtong Province, China | Chelidonic Acid |
| *Paeonia lactiflora* Pall. | An Hwei Province, China | Paeoniflorin |

D. Pharmaceutical Formulations of PHY906

The compositions of the present invention can be administered via parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, the type of concurrent treatment, if any, the frequency of treatment, and the nature of the effect desired.

The pharmaceutical formulation for systemic administration according to the invention may be formulated for enteral, parenteral, or topical administration. Indeed, all three types of formulations may be used simultaneously to achieve systemic administration of the active ingredient.

The present invention further provides compositions containing one or more agents which treat various types of cancer and/or modulate hematopoietic activity, such as the immunodulation of tuberculosis (T.B.), natural killer cells (NK), monocytes, and dendritic cells.

While individual needs vary, determination of optimal ranges of effective amounts of each component is within the skill of the art.

In addition to the pharmacologically active agent, the compositions of the present invention may contain suitable pharmaceutically acceptable carriers comprising excipients and auxiliaries which facilitate processing of the active compounds into preparations which can be used pharmaceutically for delivery to the site of action.

PHY906 can be used in the form of a medicinal preparation, for example, in solid, semi-solid or liquid form which contains PHY906, as an active ingredient, in admixture with an organic or inorganic carrier or excipient suitable for external, enteral, or parenteral applications. The active ingredient may be compounded, for example, with the usual non-toxic pharmaceutically acceptable carriers for tablets, pellets, capsules, suppositories, solutions, emulsions, suspensions, and any other form suitable for use. Formulations of the present invention encompass those which include talc, water, glucose, lactose, gum acacia, gelatin, mannitol, starch paste, magnesium trisilicate, corn starch, keratin, colloidal silica, potato starch, urea, and other carriers suitable for use in manufacturing preparations, in solid, semisolid or liquid form and in addition auxiliary, stabilizing, thickening and coloring agents, and perfumes may be used.

For preparing solid compositions such as tablets or capsules, PHY906 is mixed with a pharmaceutical carrier (e.g., conventional tableting ingredients such as corn starch, lactose, sucrose, sorbitol, talc, stearic acid, magnesium stearate, dicalcium phosphate or gums) and other pharmaceutical diluents (e.g., water) to form a solid preformulation composition containing a substantially homogeneous mixture of PHY906, or a non-toxic pharmaceutically acceptable salt thereof. When referring to the preformulation compositions as substantially homogenous, it is meant that the active ingredients are dispersed evenly throughout the composition so that the composition may be readily subdivided into equally effective unit dosage forms such as tablets, pills and capsules. This solid preformulation composition is then subdivided into unit dosage forms of the type described above containing an effective amount of the composition of the present invention, preferably in capsules.

The tablets or pills containing PHY906 can be coated or otherwise compounded to provide a dosage form affording the advantage of prolonged action. For example, the tablet or pill can comprise an inner dosage an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings such materials including a number of polymeric acids and mixtures of polymeric acids with such materials as shellac, cetyl alcohol, and cellulose acetate.

The liquid forms, in which PHY906 may be incorporated for administration orally or by injection, include aqueous solution, suitably flavored syrups, aqueous or oil suspensions, and flavored emulsions with edible oils such as cottonseed oil, sesame oil, coconut oil, or peanut oil as well as elixirs and similar pharmaceutical vehicles. Suitable dispersing or suspending agents for aqueous suspensions include synthetic natural gums, such as tragacanth, acacia, alginate, dextran, sodium carboxymethyl cellulose, methylcellulose, polyvinylpyrrolidone or gelatin.

Liquid preparations for oral administration may take the form of, for example, solutions, syrups or suspensions, or they may be presented as a dry product for reconstitution with water or other suitable vehicles before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners.

For buccal administration, the compositions of the present invention may take the form of tablets or lozenges formulated in conventional manners.

PHY906 may also be formulated for parenteral administration by injection, which includes using conventional catheterization techniques or infusion. Formulations for injection may be presented in unit dosage form, e.g., in ampules, or in multi-dose containers, with an added preservative. The compositions may take such forms as suspensions, solutions or emulsions in oily or aqueous vehicles, and may contain formulating agents such as suspending, stabilizing, and/or dispersing agents. Alternatively, the active ingredients may be in powder form for reconstitution with a suitable vehicle, e.g., sterile pyrogen-free water, before use.

Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. Liposomes can also be used to encapsulate the agent for delivery into the cell.

In practicing the methods of this invention, PHY906 may be used alone or in combination, or in combination with other therapeutic or diagnostic agents. In certain preferred embodiments, the compounds of this invention may be coadministered along with other compounds typically prescribed for cancer chemotherapy according to generally accepted medical practice. The compounds of this invention can be utilized in vivo, ordinarily in mammals, such as humans, sheep, horses, cattle, pigs, dogs, cats, rats and mice, or in vitro.

Actual methods for preparing administrable compositions and adjustments necessary for administration to subjects will be known or apparent to those skilled in the art and are described in more detail in, for example, Remington's Pharmaceutical Science, 17th Ed., Mack Publishing Company, Easton, Pa. (1985), which is incorporated herein by reference.

"Therapeutic index" is used to designate a qualitative statement of the selectivity of a drug when a therapeutic and an untoward effect are being compared. For example, if the untoward effect is designated as T (for toxic) and the therapeutic effect as E, the therapeutic index may be defined as TD50/ED50 or a similar ratio at some other arbitrary levels of response.

E. Methods of Using PHY906

The present invention provides methods of using PHY906 in combination with therapeutics for the treatment of various diseases, conditions, or disorders.

Specifically, the present invention provides methods of using PHY906 in combination with chemotherapeutic agents for the treatment of diseases, conditions, or disorders. Preferably, the present invention provides a method of treating cancer comprising administering one or more cancer chemotherapeutic agents in combination with PHY906 to a patient. The chemotherapeutic agents include but are not limited to CPT-11, 5-FU/LV, VP-16, L-OddC, capecitabine, gemcitabine, oxaliplatin, thalidomide, doxorubicin, and combinations thereof. More preferably, the present invention provides a method of treating colorectal cancer, pancreatic cancer, hepatocellular carcinoma comprising administering CPT-11/FU/LV, oxaliplatin/FU/LV, or oxaliplatin/gemcitabine in combination with PHY906.

The present invention contemplates methods of using PHY906 in combination with antiviral agents for the treatment of diseases, conditions, or disorders. Preferably, the present invention provides a method of treating a disease associated with a viral infection comprising administering one or more antiviral agents in combination with PHY906 to a patient. More preferably, the present invention provides a method of treating AIDS comprising administering one or more anti-retroviral drugs in combination with PHY906. Even more preferably, the anti-retroviral drug is selected from the group consisting of AZT, D4T, DDC, 3TC, and DDI. Most preferably, a combination comprising three antiviral drugs and PHY906 is administered to the patient. The preferred combination of three antiviral drugs include, but are not limited to, 1) D4T, 3TC, and protease inhibitor; 2) AZT, 3TC, and protease inhibitor; and 3) AZT, DDI, and protease inhibitor. The preferred protease inhibitor for treating HIV include, but not limited to, nelfinavir, indinavir, saquinavir, and ritonavir.

In one aspect of the invention, PHY906 is administered to cell lines, for example cancer or carcinoma cell lines and HIV cell lines, to evaluate the toxicity of PHY906 on different cell lines. Preferably, the cancer or carcinoma cell lines include, but are not limited to Jurkat, KB, HepG2, Hep G1.6, T-cell lymphoma (CEM), Colon 26, Colon 38, HCT116, PANC 01, PANC 02, HPAC, and the HIV cell lines include, but are not limited to, H9 cells and MT-2 cells.

In another aspect of the invention, PHY906 in combination with one or more chemotherapeutic or antiviral agent is administered to an animal to determine whether PHY906 is effective in increasing the therapeutic index of the agent and the quality of life of the animal undergoing chemotherapeutic or antiviral therapy. Preferably, the animal is a mammal. More preferably, the mammal is a human.

The animal could be an animal model for a specific cancer or viral disease. Also, the animal could have a deficient immune system. Such animal models are well-known in the art. Naturally-occurring immunodeficient mice have been used to study the immune system, cancer, and infectious diseases, including acquired immune deficiency syndrome or AIDS. For example, the nude (NU) mouse is athymic, so T cell differentiation and maturation cannot occur. Nude mice have served for many years as host for xenografts, especially human tumors and the testing of anti-cancer drugs. The severe combined immunodeficiency syndrome (SCID) mouse appears to defectively rearrange both TCR (T cell receptor) and immunoglobulin genes and displays a severe immunodeficiency. The beige (BG) mouse carries a defect in functional natural killer cells, whereas the X-linked immunodeficient (XID) mouse has a defect in the production of B cells. In addition, crosses have been made among various strains to generate lines with more comprehensive immunodeficient pheno-types (e.g., BG/NU and BG/NU/XID).

Other laboratory animals which possess little or no immune system of their own, or which have been treated with drugs or radiation, or produced through traditional genetic development or genetic engineering to have either a suppressed immune system, a weakened immune system or a modified immune system, or no immune system at all, such as, e.g. SCID horses and other SCID animals and potentially even AIDS infected animals in which AIDS has been arrested after destruction or inactivation of the animals' immune system may be considered as laboratory animal candidates for use in the present invention (Perryman L. E., McGuire, T. C., Torbeck, R. L., and Magnuson, N. S., Clin. Immunol. Immunopath., 23(1):1-9, 1982).

Murine models to study transplacental or perinatal antiretroviral therapy are known (Sharpe et al. (1987) Science 236: 1671-1674; Sharpe et al. (1988) Proc. Natl. Acad. Sci. (USA) 85: 9792-9796; Sharpe et al. (1989) J. Virol. 63: 1049-1053). In addition, mammalian models utilizing rhesus monkeys have been established to study the course of non-retroviral fetal infection by simian cytomegalovirus, Venezuelan and Western equine encephalitis virus, and mumps virus (London et al. (1986) Teratology 33: 323-331; London et al. (1977) Teratology 16: 285-296; London et al. (1982) Teratology 25: 71-79; London et al. (1979) J. Inf. Diseases 139: 324-328). Infection of rhesus monkeys (Macaca mulatta) with simian immunodeficiency virus (SIV) closely mimics HIV-1 infection in humans. Both HIV-1 and SIV are lentiviruses with similar molecular architecture (Chakrabarti et al. (1987) Nature 328: 543-547), and both cause immunodeficiency resulting in opportunistic infections as well as central nervous system damage (Letvin et al. (1985) Science 230: 71-73).

An animal model generated to study AIDS and bone marrow cell differentiation has been reported in which human lymphocytes are transiently proliferated upon coengrafting human fetal liver, thymus, and lymph nodes into SCID mice to form a SCID/nu mouse (McCune et al. (1988) Science 241: 1632-1686). Human immune tissues in these mice are susceptible to human immunodeficiency virus (HIV) infection (Namikawa et al. (1988) Science 242: 1684-1686) and the model has recently been used to test the effectiveness of AZT in delaying the replication of the AIDS virus.

U.S. Pat. No. 6,184,436 discloses a transgenic mouse to serve as a small animal model of AIDS. The mouse comprises a transgene comprising a DNA sequence encoding HIV-1 in operable linkage with the human CD4 promoter flanked by the enhancer of the mouse CD4 gene. The mouse develops a severe AIDS disease and leads to an early death.

In a preferred embodiment, the animals treated with one or more chemotherapeutic or antiviral agents in combination with PHY906 are evaluated for weight loss and survival rate and compared to control animals which are only administered the one or more chemotherapeutic or antiviral agents. The effect of PHY906 on the antitumor or antiviral activity could also be evaluated to determine the efficacy of PHY906.

Specifically, PHY906 can be evaluated as a modulator of antiviral therapy, such as AIDS. Any of the animal models for AIDS described above can be used. The first step involves determining the maximum tolerable dose of antiviral agent or combination of antiviral agents to administer to healthy animals by evaluating the weight loss of the animals. The second step involves administering the antiviral agent or agents in combination with PHY906 to the animals diagnosed with AIDS. The weights of the animals are evaluated and compared to control animals that did not receive PHY906 over the course of the treatment. Also, the hematological toxicity of the combination of PHY906 and antiviral agent or agents are evaluated by determining the red blood cell count or platelet count. The white blood cell counts of the animals are evaluated to determine the effectiveness of the combination of PHY906 and antiviral agent or agents in treating the animal of AIDS. The results of each assay are compared to those of control animals that are not given PHY906.

F. Formulations for Combination Therapy

The present invention provides combination therapy comprising a composition containing one or more compounds and PHY906 for the treatment of cancer, specifically colorectal cancer, pancreatic cancer, and hepatocellular carcinoma. Preferably, the compounds are chemotherapeutic agents such as CPT-11, 5-FU, LV, VP-16, L-OddC, capecitabine, gemcitabine, thalidomide, doxorubicin, and oxaliplatin. The compounds could also be antiviral agents such as AZT, DDI, 3TC, and D4T. The combination therapy may administer the compounds together with PHY906 as a composition or administer the compounds separately from the administration of PHY906. Therapy may be performed with the composition of the present invention alone or in conjunction with another therapy (e.g., surgery, radiation, biologic therapy).

The administration dosage and frequency of each component of the composition can be controlled independently. For example, one component may be administered orally three times per day, while the second component may be administered intramuscularly once per day. The compounds and PHY906 may also be formulated together such that one administration delivers both components. Formulations and dosages are described below.

Formulation of Pharmaceutical Compositions: The administration of each chemotherapeutic agent and PHY906 of the composition may be by any suitable means that results in a concentration of the compound that, combined with the other component, is specifically anti-neoplastic upon reaching the target region. The chemotherapeutic agent may be contained in any appropriate amount in any suitable carrier substance, and is generally present in an amount of 1-95% by weight of the total weight of the composition. The composition may be provided in a dosage form that is suitable for the oral, parenteral (e.g., intravenously, intramuscularly), rectal, cutaneous, nasal, vaginal, inhalent, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, delivery devices, suppositories, enemas, injectables, implants, sprays, or aerosols. The pharmaceutical compositions may be formulated according to conventional pharmaceutical practice (see, e.g., Remington: The Science and Practice of Pharmacy, (19th ed.) ed. A. R. Gennaro, 1995, Mack Publishing Company, Easton, Pa. and Encyclopedia of Pharmaceutical Technology, eds. J. Swarbrick and J. C. Boylan, 1988-1999, Marcel Dekker, New York.

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain drug action during a predetermined time period by maintaining a relatively, constant, effective drug level in the body with concomitant minimization of undesirable side effects associated with fluctuations in the plasma level of the active drug substance (sawtooth kinetic pattern); (iv) formulations that localize drug action by, e.g., spatial placement of a controlled release composition adjacent to or in the diseased tissue or organ; and (v) formulations that target drug action by using carriers or chemical derivatives to deliver the drug to a particular target cell type.

Administration of compounds in the form of a controlled release formulation is especially preferred in cases in which the compound, either alone or in combination with PHY906, has (i) a narrow therapeutic index (i.e., the difference between the plasma concentration leading to harmful side effects or toxic reactions and the plasma concentration leading to a therapeutic effect is small; in general, the therapeutic index, TI, is defined as the ratio of median lethal dose (LD.sub.50) to median effective dose (ED.sub.50)); (ii) a narrow absorption window in the gastro-intestinal tract; or (iii) a very short biological half-life so that frequent dosing during a day is required in order to sustain the plasma level at a therapeutic level.

Any of a number of strategies can be applied in order to obtain a controlled release formulation in which the rate of release outweighs the rate of metabolism of the compound in question. In one example, controlled release is obtained by appropriate selection of various formulation parameters and ingredients, including, e.g., various types of controlled release compositions and coatings. Thus, the drug substance is formulated with appropriate excipients into a pharmaceutical composition that, upon administration to the organism, releases the active substance in a controlled manner. Examples include single or multiple unit tablet or capsule compositions, oil solutions, suspensions, emulsions, microcapsules, microspheres, nanoparticles, patches, and liposomes.

Solid Dosage Forms for Oral Use: Formulations of the composition comprising PHY906 and one or more compounds for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like. Alternatively, the compounds may be formulated for oral use separately from PHY906.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in Encyclopedia of Pharmaceutical Technology, supra.

The compounds and PHY906 may be mixed together in the tablet, or may be partitioned. In one example, the first drug is contained on the inside of the tablet, and the second drug is on the outside, such that a substantial portion of the second drug is released prior to the release of the first drug.

Formulations for oral use may also be presented as chewing tablets, or as hard gelatin capsules wherein the active ingredient is mixed with an inert solid diluent (e.g., potato starch, lactose, microcrystalline cellulose, calcium carbonate, calcium phosphate or kaolin, or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment.

Controlled Release Oral Dosage Forms: Controlled release compositions containing the compounds alone or in combination with PHY906 for oral use may, e.g., be constructed to release the active drug substance by controlling the dissolution and/or the diffusion of the active drug substance.

Dissolution or diffusion controlled release can be achieved by appropriate coating of a tablet, capsule, pellet, or granulate formulation of compounds, or by incorporating the compound in question into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3butylene glycol, ethylene glycol methacrylate, and/or polyethylene glycols. In a controlled release matrix formulation, the matrix material may also include, e.g., hydrated metylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the compounds of the claimed combinations may also be in the form of a buoyant tablet or capsule (i.e., a tablet or capsule that, upon oral administration, floats on top of the gastric content for a certain period of time. A buoyant tablet formulation of the compound(s) can be prepared by granulating a mixture of the drug(s) with excipients and 20-75% w/w of hydrocolloids, such as hydroxyethrlcellulose, hydroxypropylcellulose and hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Liquids for Oral Administration: The compounds alone or in combination with PHY906 may be formulated as liquids for oral administration. Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable dispersing or wetting agents are, for example, naturally-occurring phosphatides (e.g., lecithin or condensation products of ethylene oxide with a fatty acid, a long chain aliphatic alcohol, or a partial ester derived from fatty acids) and a hexitol or a hexitol anhydride (e.g., polyoxyethylene stearate, polyoxyethylene sorbitol monooleate, polyoxyethylene sorbitan monooleate, and the like). Suitable suspending agents are, for example, sodium carboxymethylcellulose, methylcellulose, sodium alginate, and the like.

Parenteral Compositions: The pharmaceutical composition of the present application comprising the compounds alone or in combination with PHY906 may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions is well-known to those skilled in the art of pharmaceutical formulation. Specific formulations can be found in Remington: The Science and Practice of Pharmacy, supra.

Compositions for parenteral use may be presented in unit dosage forms (e.g., in single-dose ampoules), or in vials containing several doses and in which a suitable preservative may be added (see below). The composition may be in form of a solution, a suspension, an emulsion, an infusion device, or a delivery device for implantation, or it may be presented as a dry powder to be reconstituted with water or another suitable vehicle before use. Apart from the active drug(s), the composition may include suitable parenterally acceptable carriers and/or excipients. The compounds may be incorporated into microspheres, microcapsules, nanoparticles, liposomes, or the like for controlled release. Furthermore, the composition may include suspending, solubilizing, stabilizing, pH-adjusting agents, and/or dispersing agents.

As indicated above, the pharmaceutical compositions according to the invention may be in the form suitable for sterile injection. To prepare such a composition, the suitable compounds are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Controlled Release Parenteral Compositions: Controlled release parenteral compositions may be in form of aqueous suspensions, microspheres, microcapsules, magnetic microspheres, oil solutions, oil suspensions, or emulsions. Alternatively, the compounds may be incorporated in biocompatible carriers, liposomes, nanoparticles, implants, or infusion devices.

Materials for use in the preparation of microspheres and/or microcapsules are, e.g., biodegradable/bioerodible polymers such as polyglactin, poly-(isobutyl cyanoacrylate), poly(2-hydroxyethyl-L-glutamine) and, poly(lactic acid). Biocompatible carriers that may be used when formulating a controlled release parenteral formulation are carbohydrates (e.g., dextrans), proteins (e.g., albumin), lipoproteins, or antibodies.

Materials for use in implants can be non-biodegradable (e.g., polydimethyl siloxane) or biodegradable (e.g., poly (caprolactone), poly(lactic acid), poly(glycolic acid) or poly (ortho esters)).

Rectal Compositions: The compounds alone or in combination with PHY906 may be formulated for rectal admnistration. For rectal application, suitable dosage forms for a composition include suppositories (emulsion or suspension type), and rectal gelatin capsules (solutions or suspensions). In a typical suppository formulation, the active drug(s) are combined with an appropriate pharmaceutically acceptable suppository base such as cocoa butter, esterified fatty acids, glycerinated gelatin, and various water-soluble or dispersible bases like polyethylene glycols and polyoxyethylene sorbitan fatty acid esters. Various additives, enhancers, or surfactants may be incorporated.

Compositions for Inhalation: The compounds alone or in combination with PHY906 may be formulated for inhalation. For administration by inhalation, typical dosage forms include nasal sprays and aerosols. In a typically nasal formulation, the active ingredient(s) are dissolved or dispersed in a suitable vehicle. The pharmaceutically acceptable vehicles and excipients (as well as other pharmaceutically acceptable materials present in the composition such as diluents, enhancers, flavoring agents, and preservatives) are selected in accordance with conventional pharmaceutical practice in a manner understood by the persons skilled in the art of formulating pharmaceuticals.

Percutaneous and Topical Compositions: The compounds alone or in combination with PHY906 may be formulated for percutaneous and topical administration. The pharmaceutical compositions may also be administered topically on the skin for percutaneous absorption in dosage forms or formulations containing conventionally non-toxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gelforming agents, ointment bases, perfumes, and skin protective agents.

Examples of emulsifying agents are naturally occurring gums (e.g., gum acacia or gum tragacanth) and naturally occurring phosphatides (e.g., soybean lecithin and sorbitan monooleate derivatives). Examples of antioxidants are butylated hydroxy anisole (BHA), ascorbic acid and derivatives thereof, tocopherol and derivatives thereof, butylated hydroxy anisole, and cysteine. Examples of preservatives are parabens, such as methyl or propyl p-hydroxybenzoate, and benzalkonium chloride. Examples of humectants are glycerin, propylene glycol, sorbitol, and urea. Examples of penetration enhancers are propylene glycol, DMSO, triethanolamine, N,N-dimethylacetamide, N,N-dimethylformamide, 2-pyrrolidone and derivatives thereof, tetrahydrofurfuryl alcohol, and Azone.TM. Examples of chelating agents are sodium EDTA, citric acid, and phosphoric acid. Examples of gel forming agents are Carbopol.TM., cellulose derivatives, bentonite, alginates, gelatin and polyvinylpyrrolidone. Examples of ointment bases are beeswax, paraffin, cetyl palmitate, vegetable oils, sorbitan esters of fatty acids (Span), polyethylene glycols, and condensation products between sorbitan esters of fatty acids and ethylene oxide (e.g., polyoxyethylene sorbitan monooleate (Tween)).

The pharmaceutical compositions described above for topical administration on the skin may also be used in connection with topical administration onto or close to the part of the body that is to be treated. The compositions may be adapted for direct application or for introduction into relevant orifice(s) of the body (e.g., rectal, urethral, vaginal or oral orifices). The composition may be applied by means of special drug delivery devices such as dressings or alternatively plasters, pads, sponges, strips, or other forms of suitable flexible material.

Controlled Release Percutaneous and Topical Compositions: The compounds alone or in combination with PHY906 may be formulated for controlled release percutaneous and topical administration. There are several approaches for providing rate control over the release and transdermal permeation of a drug, including: membrane-moderated systems, adhesive diffusion-controlled systems, matrix dispersion-type systems, and microreservoir systems. A controlled release percutaneous and/or topical composition may be obtained by using a suitable mixture of the above-mentioned approaches.

In a membrane-moderated system, the active drug is present in a reservoir which is totally encapsulated in a shallow compartment molded from a drug-impermeable laminate, such as a metallic plastic laminate, and a rate-controlling polymeric membrane such as a microporous or a nonporous polymeric membrane (e.g., ethylene-vinyl acetate copolymer). The active compound is only permitted to be released through the rate-controlling polymeric membrane. In the drug reservoir, the active drug substance may either be dispersed in a solid polymer matrix or suspended in a viscous liquid medium such as silicone fluid. On the external surface of the polymeric membrane, a thin layer of an adhesive polymer is applied to achieve an intimate contact of the transdermal system with the skin surface. The adhesive polymer is preferably a hypoallergenic polymer that is compatible with the active drug.

In an adhesive diffusion-controlled system, a reservoir of the active drug is formed by directly dispersing the active drug in an adhesive polymer and then spreading the adhesive containing the active drug onto a flat sheet of substantially drug-impermeable metallic plastic backing to form a thin drug reservoir layer. A matrix dispersion-type system is characterized in that a reservoir of the active drug substance is formed by substantially homogeneously dispersing the active drug substance in a hydrophilic or lipophilic polymer matrix and then molding the drug-containing polymer into a disc with a substantially well-defined surface area and thickness. The adhesive polymer is spread along the circumference to form a strip of adhesive around the disc.

In a microreservoir system, the reservoir of the active substance is formed by first suspending the drug solids in an aqueous solution of water-soluble polymer, and then dispersing the drug suspension in a lipophilic polymer to form a plurality of microscopic spheres of drug reservoirs.

Dosages: The dosage of each compound depends on several factors, including: the administration method, the disease to be treated, the severity of the disease, whether the disease is to be treated or prevented, and the age, weight, and health of the person to be treated.

The compounds are preferably administered in an amount of about 0.1-30 mg/kg body weight per day, and more preferably in an amount of about 0.5-15 mg/kg body weight per day. As described above, the compound in question may be administered orally in the form of tablets, capsules, elixirs or syrups, or rectally in the form of suppositories. Parenteral administration of a compound is suitably performed in the form of saline solutions or with the compound incorporated into liposomes. In cases where the compound in itself is not sufficiently soluble to be dissolved, a solubilizer such as ethanol can be applied.

In light of the foregoing general discussion, the specific examples presented below are illustrative only and are not intended to limit the scope of the invention. Other generic and specific configurations will be apparent to those persons skilled in the art.

EXAMPLES

Materials and Methods

CPT-11 (irinotecan, Camptosar®) was purchased from Pharmacia & Upjohn Co (Kalamazoo, Mich.). 5-Fluorouracil (5-FU or FU), folinic acid (leucovorin, LV), loperamide, *E. coli* beta-glucuronidase, methylene blue, and phenolphthalein glucuronidate were purchased from Sigma, Co. (St. Louis, Mo.). MEME medium was prepared at the Yale University Cancer Center, according to the standard procedures. RPMI 1640 medium was purchased from JRH Co. Kanamycin, pancreatin, and trypan blue were purchased from Gibco Co. (Grand Island, N.Y.). PHY906, PHY-915, PHY-14ST, and PHY-15ST botanical preparations were provided by Sun Ten Pharmaceutical Inc. (Taipei, Taiwan). PHY-14ST, previously called TJ-14ST, consists of seven herbs: *Pinelliae ternata Breit., Scuellaria baicalensis Georgi, Coptis chinensis Franch, Glycyrrhiza uralensis Fisch, Fructus ziziphi, Panax ginseng C. A. Mey.*, and *Zingiber officinale Rosc.* PHY-15ST, previously called TJ-15ST, consists of *pueraria lobata Ohwi, Coptis chinensis Franch, Scuellaria baicalensis Georgi*, and *Glycyrrhiza uralensis Fisch.* PHY-915 consists of five herbs: *Panax ginseng C.A. Mey., Zingiber officinale Rosc., Atractylodes macrocephala Koidz, Saposhnikovia divaricata Schischk.*, and *Citrus reticulata Blanco.*

Preparation of herbal extract from dry powder: One gram of (A) PHY906 dry powder, containing either 50% (research batch) or 10% (clinical batch) starch excipient; or (B) PHY-915, PHY-14ST, or PHY-15ST herbal formulations, containing unknown amounts of excipient, was added to 10 ml of 80° C. $H_2O$ and incubated at 80° C. for 30 minutes. The supernatant was separated from the debris by centrifugation (2060 g, 15 min) and used immediately. The concentration of PHY906 supernatant is calculated as either 50 mg/ml (from research batch) or 90 mg/ml (from clinical batch), based on the dry weight of aqueous extract of raw herbs. The concentrations of other herbal formulations were considered as 100 mg/ml, based on dry weight of the powder. The supernatant was sterilized using a 0.45 μm sterile Acrodisc filter (Gelman Sciences) for growth inhibition studies in tissue culture.

Mice: Female BDF-1 mice (4-6 weeks old) were purchased from Charles River Laboratories (Wilmington, Mass.). Male athymic NCr nude mice (4 weeks old) were purchased from Taconic Farms (Garmantown, N.Y.). Both kinds of mice weighing between 16 g and 20 g were used for this study.

Anti-Tumor Studies: Murine Colon 38 ($1-2\times10^6$ cells in 0.1 ml PBS) or human HepG2 cells ($1-2\times10^6$ cells in 0.1 ml PBS) were transplanted subcutaneously into BDF1 or NCr athymic nude mice, respectively. The length and width of the tumors were measured daily with sliding calipers. The tumor weight was estimated according to the following formula (Pizzorno G, Wiegand R, Lentz S, et al., Cancer Res. 52:1660-1665 (1992)):

Tumor weight (mg)=length (mm)×width $(mm)^2/2$.

After 10 to 14 days, mice (five animals/group) with tumor weights ranging from 150-200 mg were selected for drug studies (Guo X, Lerner-Tung M, Chen H X, et al., Biochem Pharmacol 49:1111-1116 (1995)). Mice were sacrificed when the tumor size reached 10% of body weight. PHY906 was administered orally either alone or with anti-cancer chemotherapeutic agents. The effect of PHY906 on antitumor efficacy and the reduction of toxicity by the agents were evaluated. CPT-11 was given intraperitoneally (i.p.) 30 min after PHY906 administration with the selected dose. The regimen of FU/LV combination therapy was given as follows:

(A) treatment with FU/LV alone: first dose of LV (50 mg/kg, i.p.), one hour later the second dose of LV (50 mg/kg; i.p.), then immediately given FU (100 mg/kg, i.p.)

(B) treatment with FU/LV plus PHY906: first dose of LV (50 mg/kg, i.p.), followed 30 minutes later by PHY906 (500 mg/kg, orally), followed 30 min later by a second dose of LV (50 mg/kg, i.p.), then immediately by the FU dose (100 mg/kg, i.p.)

The CPT-11/FU/LV triple drug combination was giving as follows: Group (A) CPT-11/FU/LV only: mice were given the first dose of LV (50 mg/kg, i.p.) one hour before administration of CPT-11, then immediately followed by LV (50 mg/kg, i.p.) and FU (100 mg/kg, i.p.)

Group (B) CPT-11/FU/LV plus PHY906: mice were given the first dose of LV (50 mg/kg, i.p.) 30 min before PHY906 (500 mg/kg, orally). Then 30 minutes after PHY906 administration, mice were treated with CPT-11, immediately followed by LV (50 mg/kg, i.p.) and FU (100 mg/kg, i.p.) on day 0.

The first day of treatment was defined as day 0. PHY906 was given orally twice a day (10 am and 3 pm) for either 4 or 8 days beginning on day 0. For the control group, mice were administrated a vehicle, either PBS for i.p. or $H_2O$ for p.o. (oral administration). Animals were monitored for mortality, weight loss, and tumor size daily.

Blood Cell Counts: Blood (20 μl) was taken from mice on days 0, 3, 6, 9 and 12 with micro-capillary tubes. Blood was then be diluted to 200 μl with normal saline (0.85% Sodium Chloride). WBC, RBC and platelets were counted by a BAKER SYSTEM 9100™ HEMATOLOGY ANALYZER (Biochem ImmunoSystems Inc., Allentown, Pa. 18103-9562).

Cell Lines and Culture Conditions: The human HepG2 (hepatocellular carcinoma), HCT 116 (colon cancer), CEM (leukemia), and KB (oral epidermoid carcinoma) cell lines, and murine Colon 38 cell line were purchased from the American Type Culture Collection (Rockville, Md.). The HepG2 cell line was routinely grown in MEME media, supplemented with 10% fetal bovine serum (FBS) and 100 μg/ml kanamycin. Colon 38, HCT116, KB, and CEM cell lines were grown in RPMI 1640 media with 10% FBS and 100 μg/ml kanamycin. Cells were incubated at 37° C. in a humidified atmosphere of 5% $CO_2$: 95% air.

Cytotoxicity in human or mouse carcinoma cell lines: Cell growth inhibition was measured using the methylene blue uptake assay. Cancer cells ($1 \times 10^4$) were seeded into a 24-well plate in either 1 ml of MEME medium or RPM11640 with 10% FBS and 100 μg/ml kanamycin on day 0. The freshly prepared and sterilized PHY906 extract was added to cells on day 1, at various concentrations, and incubated at 37° C. for 3 days. The medium was then removed, and the cell layer was stained for 30 min with 0.3 ml of 0.5% (w/v) methylene blue solution (in 50% ethanol). The plates were washed 3 times with tap water, dried, and the cell layer was lysed with 1 ml of 1% Sarkosyl solution (in PBS). The lysate solution was read on an Elx800 kinetic microplate reader (Bio-Tek Instruments, Inc.) at 595 nm.

Example 1

Evaluation of Toxicity of PHY906 on Different Cell Lines

Briefly, one gram of each batch of PHY906 was added with 10 ml of water (1 mg/ml). See Table 6 for the batch properties.

TABLE 6

Batch Properties PHY906

| Property | Batch A | Batch B |
|---|---|---|
| Origin | Taiwan, Sun-Ten | Taiwan, Sun-Ten |
| Preparation method | Standard | Standard |

The supernatant was collected after centrifugation and filtered through a 0.22 μm filter. Four cell types were used to test for biological effects of each batch of PHY906: a) KB cells (ATCC cat. # CCL-17); b) HepG2 cells (ATCC cat # HB-8065); c) T-cell lymphoma cell line (CEM cells); d) Colon 38 and e) HCT116 (ATCC cat # CCL-247).

The carcinoma cells ($1 \times 10^4$) were seeded into a 24-well plate in either 1 ml of MEME medium or RPMI-1640 with 10% FBS and 100 μg Kanamycin on day 0. After 24 hours, the PHY906 extract was added to the cells at varying concentrations and incubated at 37° C. for 3 days. The medium was then removed and the cells stained with 0.3 ml of 0.5% (w/v) methylene blue solution (in 50% EtOH) for 30 min. The plates were washed 3 times with tap water, dried, and the cell layer was lysed with 1 ml of 1% Sarkosyl solution (in PBS). The lysate solution was read on a Elx800 kinetic microplate reader (Bio-Tec Instruments, Inc.) at 595 nm.

Cytotoxicity studies were performed with human T-cell lymphoma cell line (CEM). CEM cells ($5 \times 10^4$) were grown in 1 ml RPMI 1640 medium with 20% displayed fetal bovine serum. The PHY906 extract was added at day 0. The growth of cells was assessed 3 days post addition of PHY906. The number of cells were estimated using a hemacytometer.

The results of the assays using the two (2) batches are displayed in Table 7. Based on these data, PHY906 sources A and B have relatively little toxicity for KB, CEM and HCT116 cells, while having significantly greater cytotoxic effects against Colon 38 and HepG2 cells (see Table 7). Similar results are shown in Example 11, Table 10.

TABLE 7

Cytotoxicity of Traditional Herbal Formulations in Different Cell Lines

| Herbal Formulation[b] | $IC_{50}$ (mg/ml)[a] | | | | |
|---|---|---|---|---|---|
| | KB | HepG2 | CEM | Colon 38 | HCT116 |
| PHY906A | 1.35 ± 0.52 | 0.28 ± 0.17 | 1.45 ± 0.45 | 0.08 | 1.3 |
| PHY906B | 1.80 ± 0.99 | 0.17 ± 0.12 | 1.28 ± 0.02 | 0.08 | 1.2 |

[a]Based on the dry weight of herbal formulation.
[b]Different research batch of PHY906 containing 50% excipient.

Example 2

Determination of CPT-11 Dose on BDF-1 and Nude Mice

Animal weight loss was monitored as an indication of toxicity caused by anticancer chemotherapy agents. The effect of CPT-11 on weight loss in non-tumor bearing BDF-1 mice was studied using six different dosages: 100, 200, 300, 400, 600, or 800 mg/kg body weight to determine the maximum tolerable dose in mice. A single bolus dose of CPT-11 was administered intraperitoneally (i.p.) at the beginning of the study, and weight loss was monitored daily for 12 days.

One dose of CPT-11 was administered i.p. to each mouse at the beginning of the study, and the weight loss of the animal was then monitored daily for 12 days.

Dosages lower than 200 mg/kg had little effect on body weight (comparison made with control mice receiving no CPT-11 treatments). In contrast, drug doses greater than or equal to 600 mg/kg resulted in animal death on the second day after CPT-11 administration. In general, mice were able to tolerate doses up to 400 mg/kg.

Figure 1:
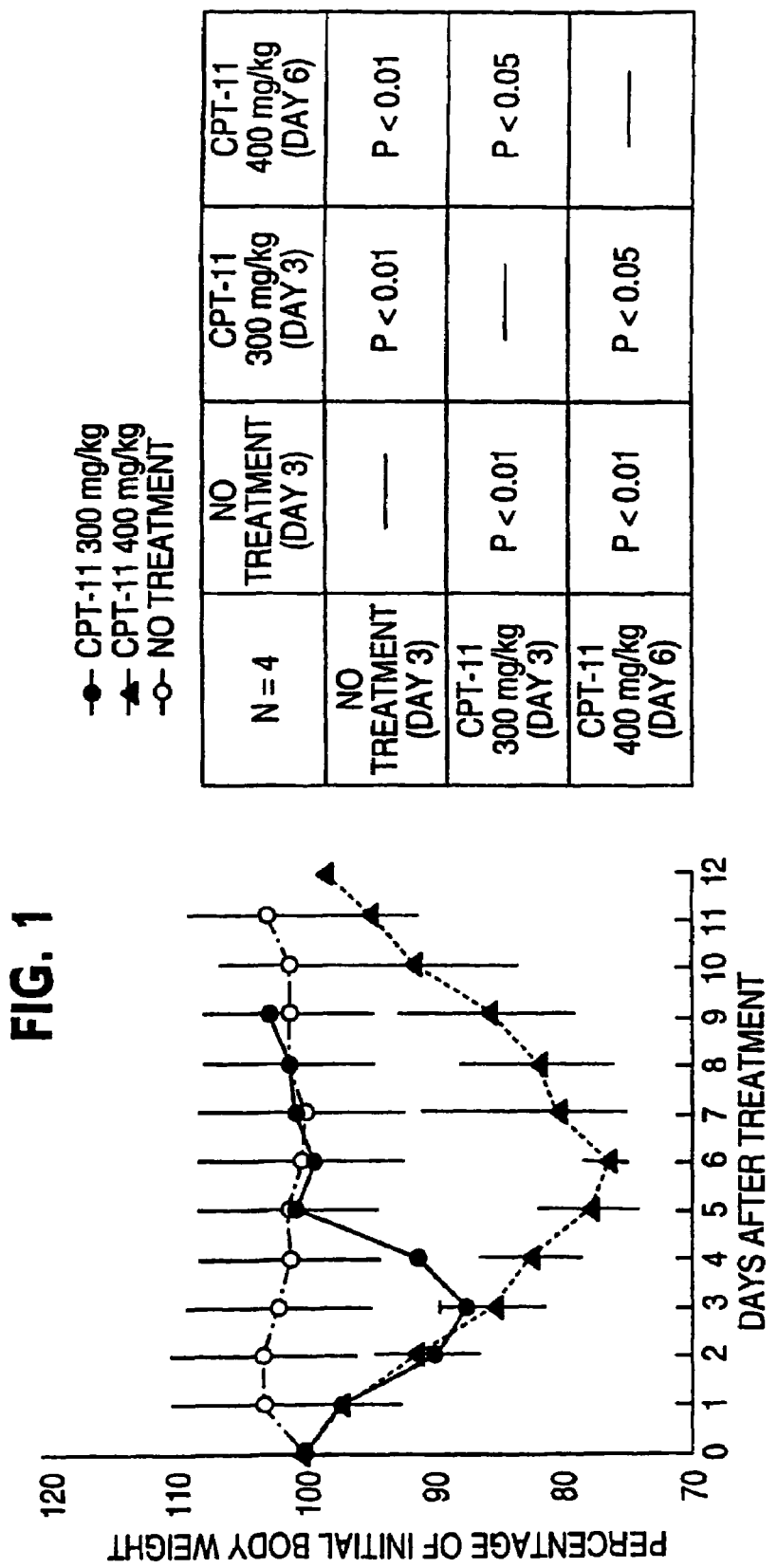
FIG. 1. Effect on Different Dosage of CPT-11 in Non-Tumor Bearing BDF-1 Mice. CPT-11 was given intraperitoneally (i.p.) on day 0 only (N=5 in each group).

The profiles of the weight loss of the surviving mice are shown in FIG. 1. The average body weights of the mice treated with 300 mg/kg CPT-11 were significantly less than those of the mice that received no treatment with CPT-11 until 5 days after treatment (FIG. 1). The average body weights of these two groups of mice were not significantly different from 5 days after treatment until the end of the trial. Both the duration and extent of the weight loss were sensitive to the dose of CPT-11 administered to the animal.

Weight loss was observed immediately after CPT-11 treatment and continued for six days in mice injected with 400 mg/kg of CPT-11. These animals gradually recovered their original body weight on day 12. Based on these results, either 400 mg/kg or 300 mg/kg CPT-11 was used in the BDF-1 mice model. However, nude mice inoculated with human tumor cells were significantly more sensitive to CPT-11 treatment than normal BDF-1 mice. The maximum tolerable dose of CPT-11 in nude mice bearing the human HepG2 xenografts was 200 mg/kg (data not shown).

Example 3

Effect of PHY906 on CPT-11 Induced Body Weight Loss in Tumor Bearing BDF-1 Mice

PHY906 was evaluated as a modulator of CPT-11 therapy for toxic side effects in mice inoculated with Colon 38 tumor cells. Based on the previous findings (Example 2), a single bolus dose of 400 mg/kg CPT-11 was selected to study the effect of PHY906 on weight-loss associated with toxicity of CPT-11. To evaluate whether PHY906 impairs the antitumor efficacy of CPT-11, mice were implanted subcutaneously with Colon 38 tumor cells. Ten to 14 days after inoculation, mice were treated with CPT-11 (400 mg/kg, i.p.) in the absence or presence of PHY906, which was given orally twice a day at varying doses (125 mg/kg, 250 mg/kg, and 500 mg/kg). PHY906 treatment was continued at the dose indicated for 8 consecutive days.

Figure 2:
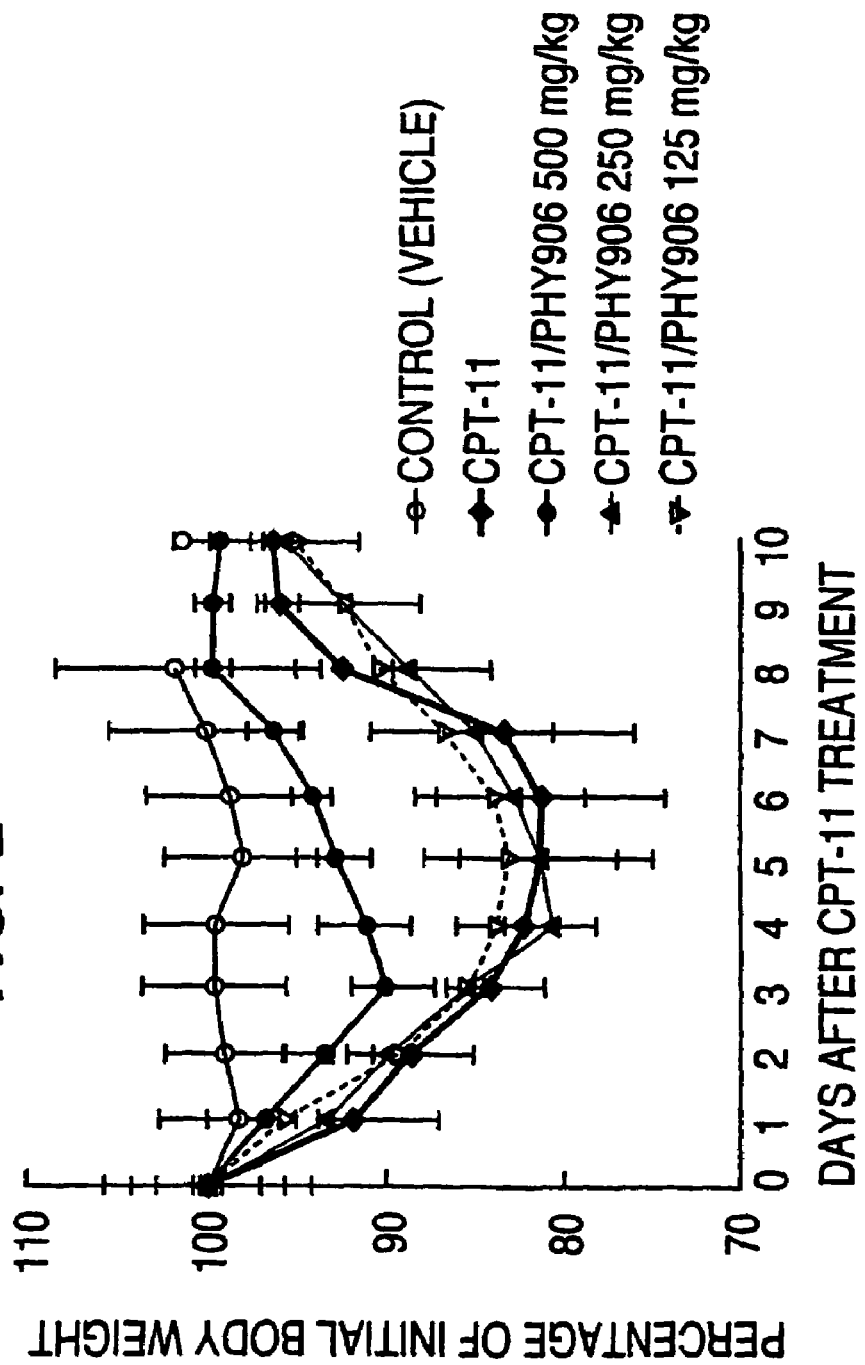
FIG. 2. Effect of PHY906 on Body Weight in CPT-11 Treated BDF-1 Mice Bearing Colon 38 Tumor. CPT-11 (400 mg/kg) was given intraperitoneally on day 0 only. PHY906 was given orally twice a day for 8 days beginning on day 0 at the dose indicated (N=5 in each group).

FIG. 2 shows that the effect of PHY906 on weight loss in CPT-11 treated mice is dose dependent. CPT-11 treated animals receiving supplemental treatment with 500 mg/kg/b.i.d. of PHY906 exhibited significant improvement in maintaining body weight and recovered their original body weight more rapidly ($p<0.01$). Table 8 summarizes the statistical results. However, mice receiving 250 mg/kg/b.i.d. of PHY906 showed no difference in body weight loss.

These preliminary results suggest that the herbal composition PHY906 can be used as a modulator for CPT-11 chemotherapy to significantly improve and alleviate the toxic side effects of CPT-11 without compromising the anti-tumor efficacy of the CPT-11.

Example 5

Figure 3:
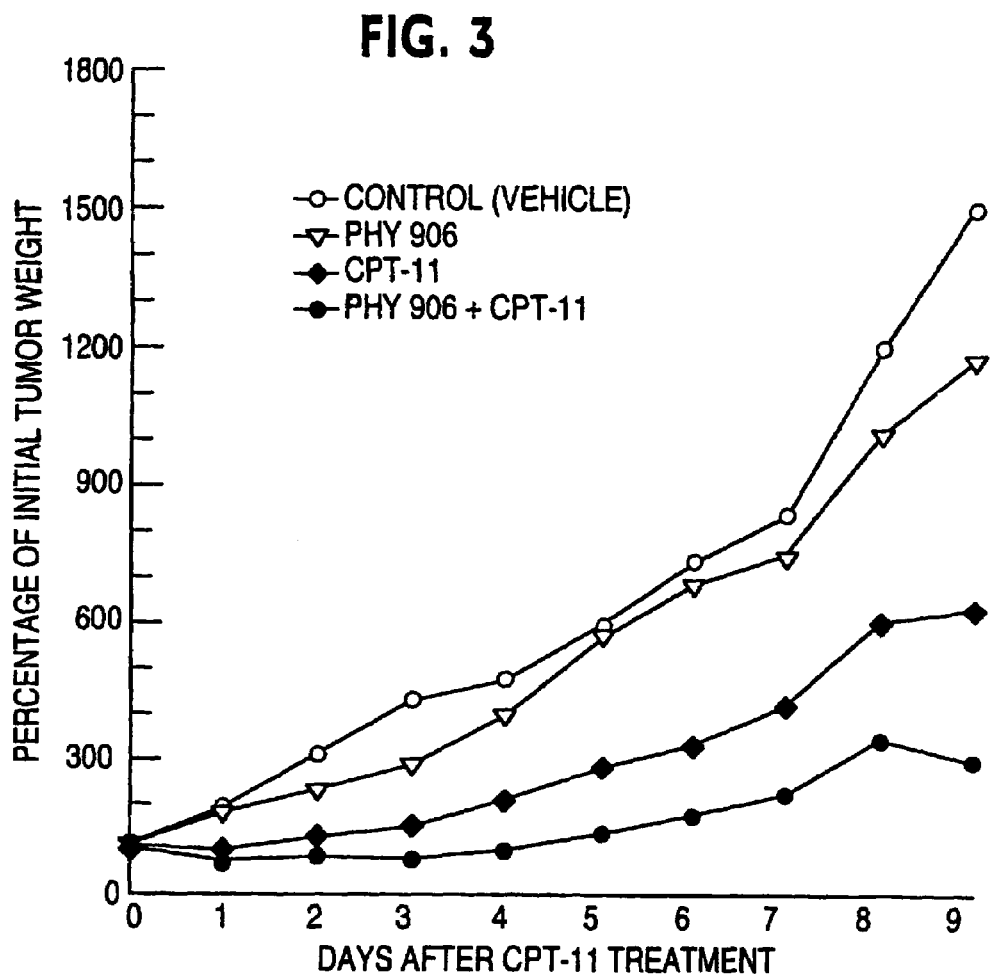
FIG. 3. Effect of PHY906 on Tumor Growth in CPT-11 Treated BDF-1 Mice Bearing Colon 38 Tumor. CPT-11 (400 mg/kg) was given intraperitoneally on day 0 only. PHY906 (500 mg/kg) was given orally twice a day for 8 days beginning on day 0. The p values were calculated using the Student's paired t-test. (N=5 in each group).

Effect of PHY906 on Antitumor Activity and Hematological Toxicity of CPT-11 in BDF-1 Mice Bearing Colon 38 Tumors Based on the results obtained in the above studies, 500 mg/kg/b.i.d. PHY906 offers the best protection for host toxicity induced by the maximum tolerable dose of 400 mg/kg CPT-11. This set of dosages was used for the next studies. Colon 38-bearing BDF-1 mice treated with one dose of CPT-11 (400 mg/kg, i.p.) were given 500 mg/kg/b.i.d. PHY906 orally for either 4 or 8 days. Five mice were used in each group, and the experiment was repeated eight times. FIG. 3 represents a typical result of all of experiments. The antitumor activity of CPT-11, as measured by tumor size, was not compromised by the concomitant PHY906 therapy in the animal model. In fact, a slight reduction in tumor size occurred, suggesting that PHY906 may potentiate the antitumor activity of CPT-11.

Figure 4:
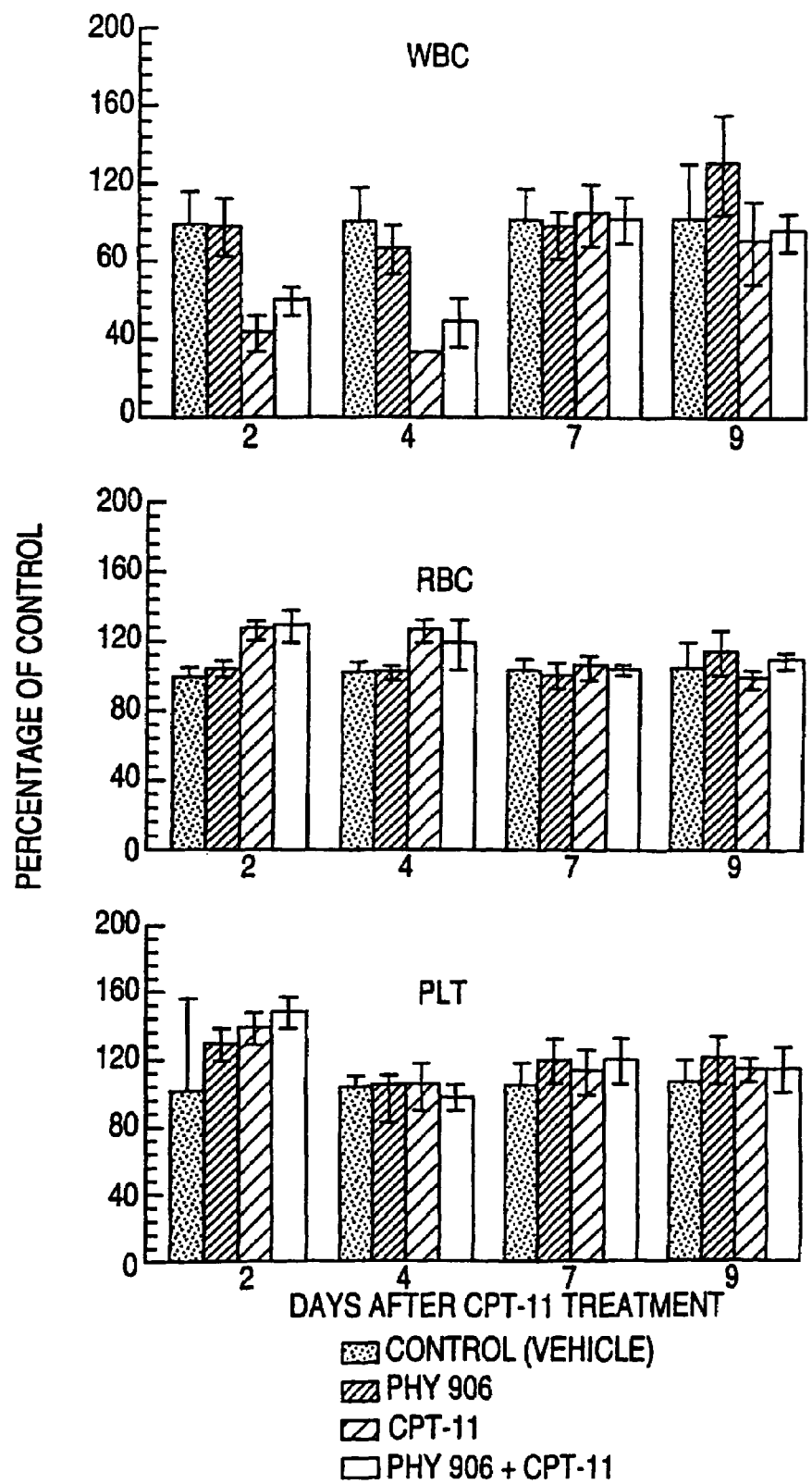
FIG. 4. Effect of PHY906 on Hematological Change in CPT-11 Treated BDF-1 Mice Bearing Colon 38 Tumor (N=5 in each group). CPT-11 (400 mg/kg) was given intraperitoneally on day 0 only. PHY906 (500 mg/kg) was given orally twice a day for 4 days beginning on day 0 (N=5 in each group).

Myelo-suppression is a common side effect among patients treated with CPT-11 (Bleiberg H and Cvitkovic E., Eur J Cancer 32A(Suppl 3):S18-S23 (1996)). To evaluate whether PHY906 beneficially reverses myelo-toxicity induced by CPT-11, hematological activity was examined in BDF-1 mice bearing Colon 38 tumors. As shown in FIG. 4, PHY906 was found to have no impact on red blood cell count or platelet count among all regimens, and demonstrated no protection on myelo-suppression induced by CPT-11. With

TABLE 8

Statistical Analysis of PHY906 on Weight Loss in Tumor Bearing Mice Treated With CPT-11

| N = 5 | No Treatment | CPT-11 | CPT-11/PHY906 500 mg/kg | CPT-11/PHY906 250 mg/kg | CPT-11/PHY906 125 mg/kg |
|---|---|---|---|---|---|
| No Treatment | — | $P < 0.01$ | $P < 0.05$ | $P < 0.01$ | $P < 0.01$ |
| CPT-11 | $P < 0.01$ | — | $P < 0.01$ | $P > 0.1$ | $P > 0.1$ |
| CPT-11/PHY906 500 mg/kg | $P < 0.05$ | $P < 0.01$ | — | $P < 0.01$ | $P < 0.01$ |
| CPT-11/PHY906 250 mg/kg | $P < 0.01$ | $P > 0.1$ | $P < 0.01$ | — | $P > 0.1$ |
| CPT-11/PHY906 125 mg/kg | $P < 0.01$ | $P > 0.1$ | $P < 0.01$ | $P > 0.1$ | — |

Example 4

Tumor Weight of Colon 38 Inoculated Mice Treated with CPT-11 and PHY906

Mice were treated as set forth in Example 3 and evaluated for tumor weights over a nine day period. The results demonstrate that treatment with PHY906 neither impedes nor impairs the antitumor efficacy of the CPT-11 (FIG. 3). In fact, the data suggest that this herbal medicine may actually enhance CPT-11 anti-tumor activity.

respect to the antitumor activity and hematological activity, there was no significant difference between a 4-day or 8-day co-treatment of PHY906 with CPT-11 (data not shown).

Example 6

Effect of PHY906 on Mortality of CPT-11 on BDF-1 Mice Bearing Colon 38 Tumors

Mice were divided into four groups with different treatment regimens: Group (A) treatment with vehicle; Group (B)

treatment with a single dose of 400 mg/kg CPT-11 by i.p. injection; Group (C) treatment with PHY906 (500 mg/kg/b.i.d.) alone; or Group (D) treatment with a single dose of 400 mg/kg CPT-11 plus 500 mg/kg/b.i.d. PHY906 for 4 or 8 days. The sequence of each treatment regimen appears in Materials and Methods. As depicted in Table 9, 35 of 35 tumor-bearing mice (100%) from Group A and 15 of 15 mice (100%) from Group C survived treatment with either vehicle or PHY906 alone for 4 or 8 days, indicating no or very low toxicity for PHY906. In contrast, treatment with CPT-11 alone (Group B) resulted in only 33 of 40 tumor-bearing mice (82.5%) surviving after 8 days. However, this survival rate dramatically improved to either 95% (19 of 20 mice) or 100% (24 of 24 mice) after receiving 4 or 8 days of PHY906 treatment in combination with CPT-11 (Group D). This suggests that PHY906 treatment can protect mice against mortality induced by a single dose of 400 mg/kg CPT-11.

TABLE 9

Effect of PHY906 on Survival of CPT-11 Treated BDF-1 Mice Bearing Colon 38 Tumor.

| Medica-tion Regimen | Treatment | | | | Total No. of Mice | | |
|---|---|---|---|---|---|---|---|
| | CPT-11 | | PHY906 | | | | |
| | Dose (mg/kg) | Days | Dose (mg/kg) | Days | Treated N | Survived N | Survival[a] % |
| A | 0 | 0 | 0 | 0 | 35 | 35 | 100 |
| B[b] | 400 | 1 | 0 | 0 | 40 | 33 | 82.5 |
| C | 0 | 0 | 500 | 4 | 35 | 35 | 100 |
| | 0 | 0 | 500 | 8 | 15 | 15 | 100 |
| D[c] | 400 | 1 | 500 | 4 | 20 | 19 | 95 |
| | 400 | 1 | 500 | 8 | 24 | 24 | 100 |

[a] All the animals were observed for 14 days.
[b] 7 of 40 mice with CPT-11 treatment died on day 5 (N = 1), 6 (N = 3), 7 (N = 1) and 8 (N = 2).
[c] With the combination treatment of CPT-11 and PHY906 (4 days) treatment, one mouse died on day 6.

Example 7

Effect of PHY906 on the Antitumor Activity of FU/LV in BDF-1 Mice Bearing Colon 38 Tumors FU/LV in combination shows potent antitumor activity and is used as the firstline treatment of colorectal cancer in patients (Goldber R. M. and Erlichman C., Oncology 12: 59-63 (1988); Saltz L. B, Cox J. V, Blanke C, et al., New. Eng. J. Med. 343:905-914 (2000)). Therefore, experiments similar to that described above for CPT-11 treatment were carried out with FU/LV in animals. Colon 38 tumor bearing mice were divided into four groups: Group (A) treatment with vehicle; Group (B): treatment with PHY906 alone; Group (C) treatment with FU/LV alone; and Group (D) treatment with FU/LV plus PHY906. The sequence of each regimen appears in Materials and Methods. In this set of experiments, FU/LV was given to mice only once on day 0, whereas PHY906 was administered twice daily for 4 consecutive days.

Figure 5:
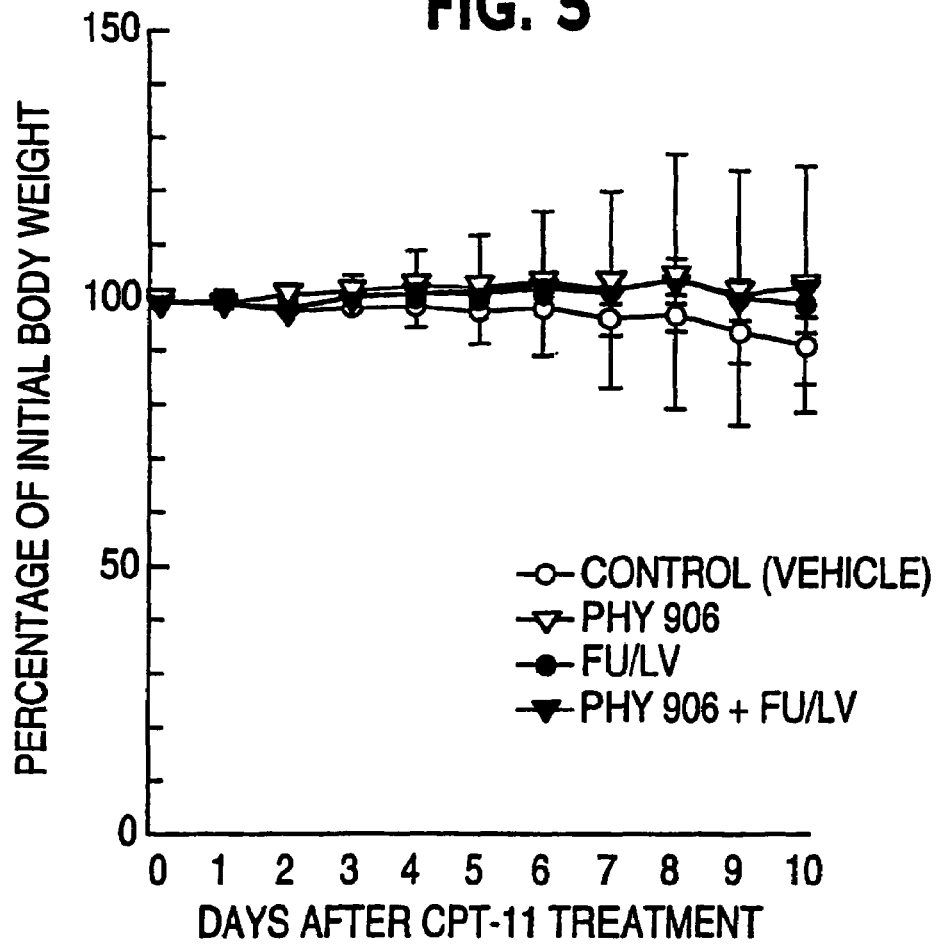
FIG. 5. Effect of PHY906 on Body Weight in FU/LV Treated BDF-1 Mice Bearing Colon 38 Tumor. Sequential administration of LV (100 mg/kg) and FU (100 mg/kg) was given intraperitoneally during 1 hr period on day 0 only, as described in Materials and Methods. PHY906 was given orally 30 min after initial dose of LV on day 0 and continued twice a day for 4 days at 500 mg/kg (N=5 in each group).
Figure 6:
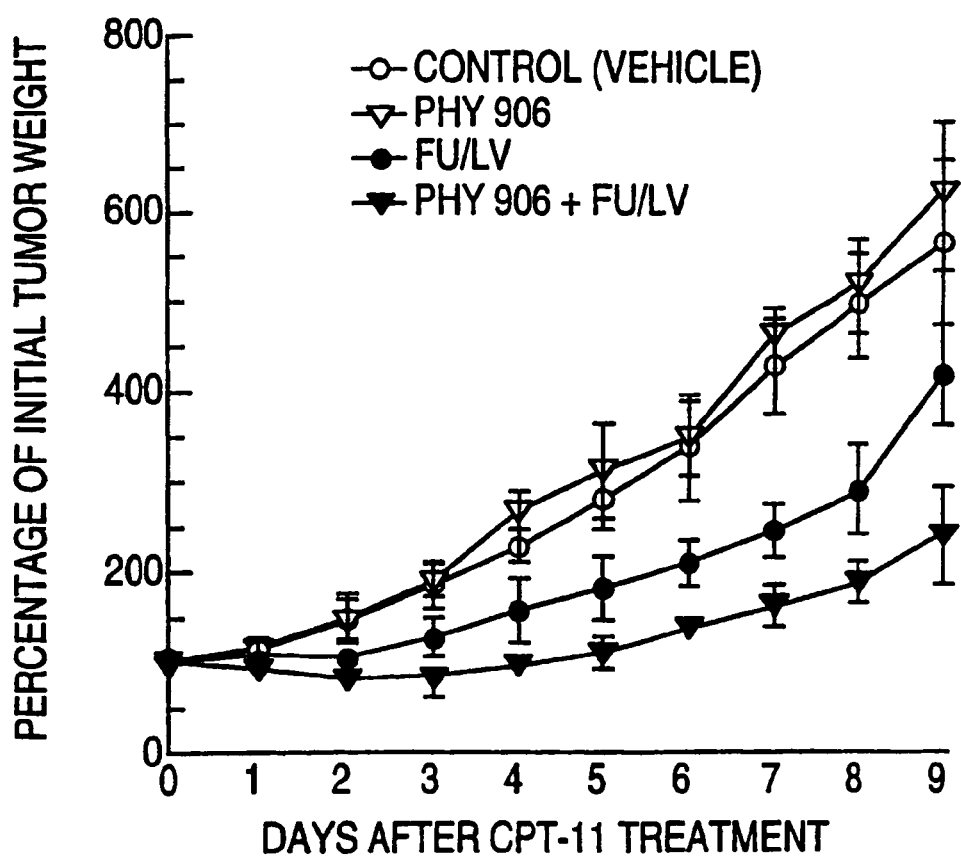
FIG. 6. Effect of PHY906 on Tumor Growth in FU/LV Treated BDF-1 Mice Bearing Colon 38 Tumor. Sequential administration of LV (100 mg/kg) and FU (100 mg/kg) was given intraperitoneally during 1 hr period on day 0 only, as described in Materials and Methods. PHY906 was given orally 30 min after initial dose of LV on day 0 and continued twice a day for 4 days at 500 mg/kg (N=5 in each group).
Figure 7:
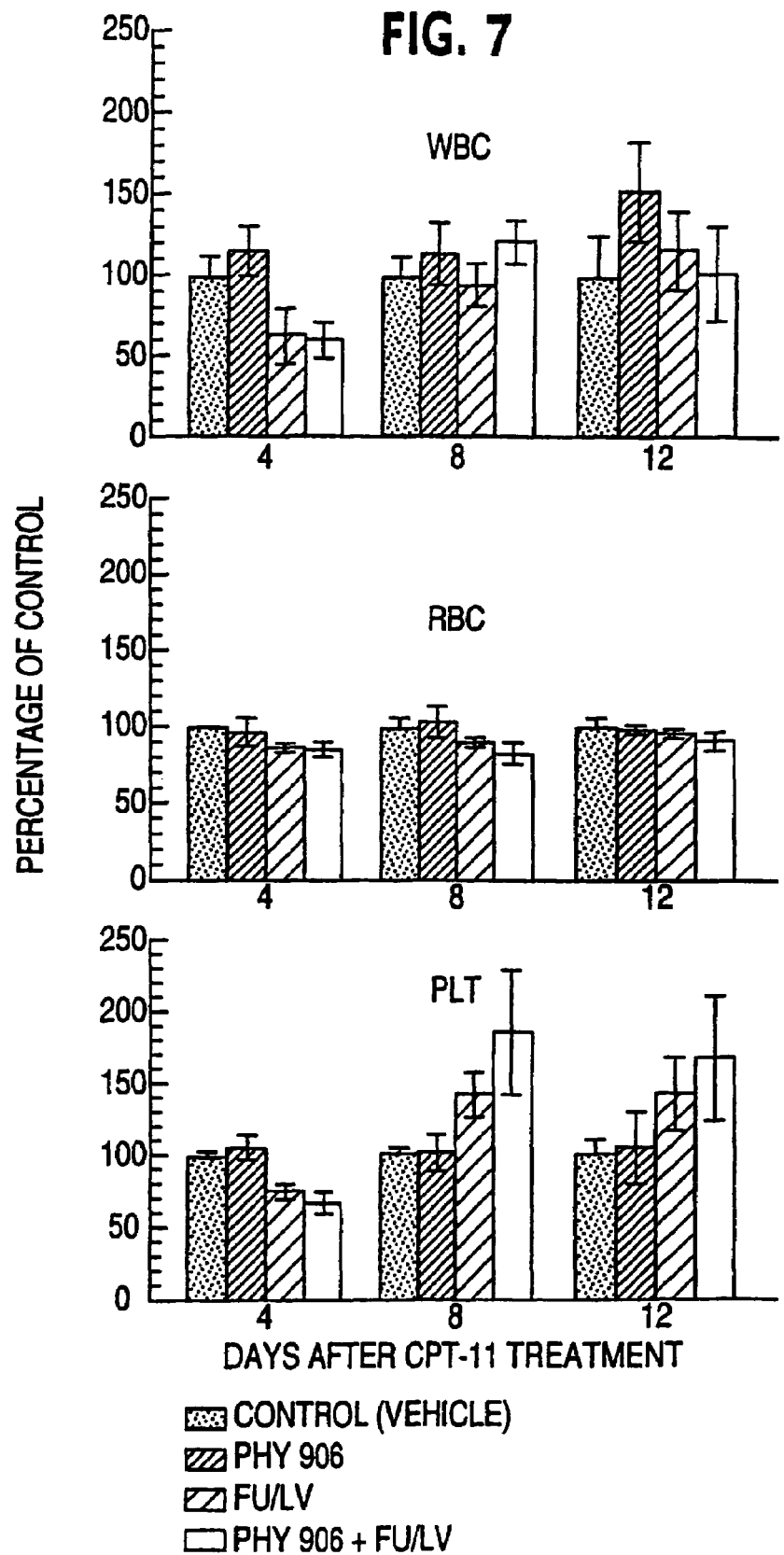
FIG. 7. Effect of PHY906 on Hematological Change in FU/LV Treated BDF-1 Mice Bearing Colon 38 Tumor. Sequential administration of LV (100 mg/kg) and FU (100 mg/kg) was given intraperitoneally during 1 hr period on day 0 only, as described in Materials and Methods. PHY906 was given orally 30 min after initial dose of LV on day 0 and continued twice a day for 4 days at 500 mg/kg (N=5 in each group).

Changes in body weight and tumor size were monitored daily, as shown in FIGS. 5 and 6, respectively. As depicted in FIG. 5, little change in body weight occurred in the four groups. This observation is in contrast to that obtained with CPT-11 treatment. Since dose-response studies of FU/LV on body weight loss were not performed, it is possible that the FU/LV dose administered in this experiment was not high enough to induce toxicity and associated body weight loss. Although body weight loss was insufficient to demonstrate a protective effect PHY906 on FU/LV, FIG. 6 indicates that concomitant treatment of PHY906 did not impair the antitumor activity of FU/LV in BDF-1 mice bearing Colon 38 tumors. The tumor growth profile of animals in Group D is slower than that in Group C, suggesting that PHY906 may enhance the antitumor activity of FU/LV in this animal model. In addition, the hematological toxicity of FU/LV in treated mice concomitantly administered PHY906 was monitored on days 4, 8, and 12. Leucopenia or thrombocytopenia, well known side effects induced by FU/LV (van der Wilt C. L, van Groeningen, C. J, Pinedo H. M, et al., J. Cancer Res. Clin. Oncol. 123:595-601 (1997)), was not reversed by PHY906 (FIG. 7).

Example 8

Effect of PHY906 on Antitumor Activity of CPT-11/FU/LV in BDF-1 Mice Bearing Colon 38 Tumors The FDA recently approved the new triple combination therapy of CPT-11 plus FU/LV as a firstline treatment for advanced colorectal cancer (Goldber R. M. and Erlichman C., Oncology 12: 59-63 (1988); Saltz L. B, Cox J. V, Blanke C, et al., New. Eng. J. Med. 343:905-914 (2000)). This regimen has been proven to slow the progress of tumor growth as well as the mortality rate. However, severe, late-onset diarrhea is often observed in patients receiving this triple treatment regimen. Previous experiments demonstrated that PHY906 could increase the therapeutic index of CPT-11 in BDF-1 mice bearing Colon 38 tumors. Therefore, PHY906 was evaluated using a similar protocol as in Example 7 for its efficacy on alleviating the dose-limiting toxicity of triple chemotherapy. BDF-1 mice bearing Colon 38 tumors were divided into two groups: Group (A) treated with CPT-11/FU/LV only; Group (B) treated with CPT-11/FU/LV plus PHY906. The doses of FU and LV used in both groups were 100 mg/kg each, because very low toxicity was observed in previous studies at these doses. A dose-dependent study of CPT-11 was not performed in this triple chemotherapy regimen, but either 200 mg/kg or 300 mg/kg CPT-11 was used. The sequence of each regimen appears in Materials and Methods. PHY906 was administered twice daily for 4 days post chemotherapy.

Figure 8:
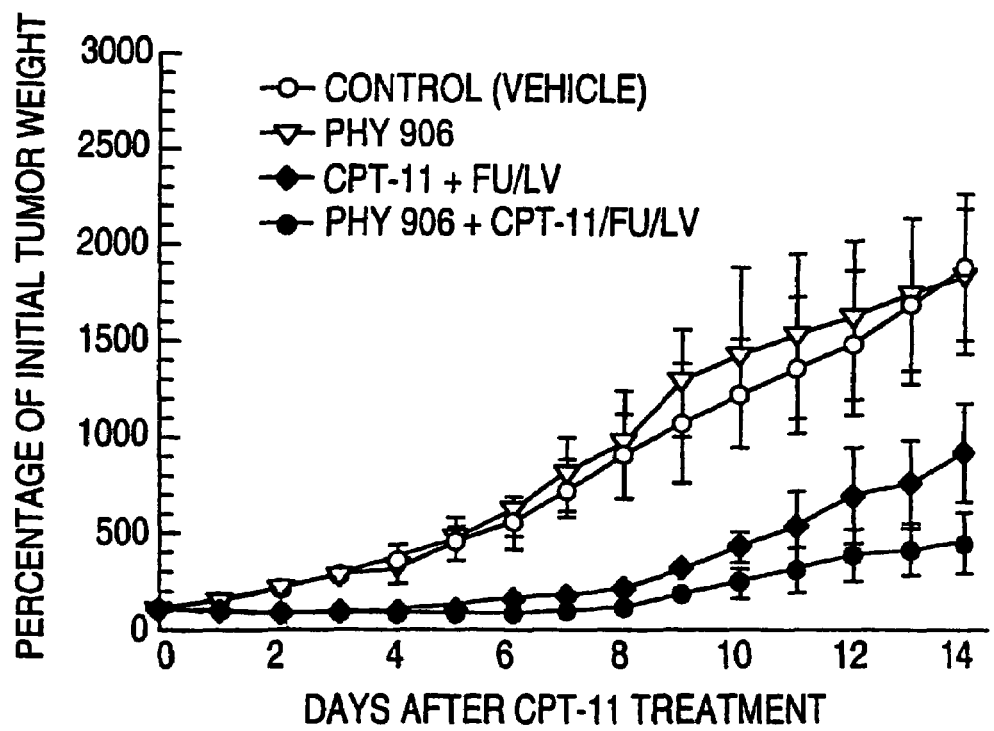
FIG. 8. Effect of PHY906 on Tumor Growth in CPT-11/FU/LV Treated BDF-1 Mice Bearing Colon 38 Tumor. Sequential administration of LV (100 mg/kg), CPT-11 (200 mg/kg) and FU (100 mg/kg) was given intraperitoneally during 1 hr period on day 0 only, as described in Materials and Methods. PHY906 was given orally 30 min after initial dose of LV on day 0 and continued twice a day for 4 days at 500 mg/kg (N=5 in each group).
Figure 9:
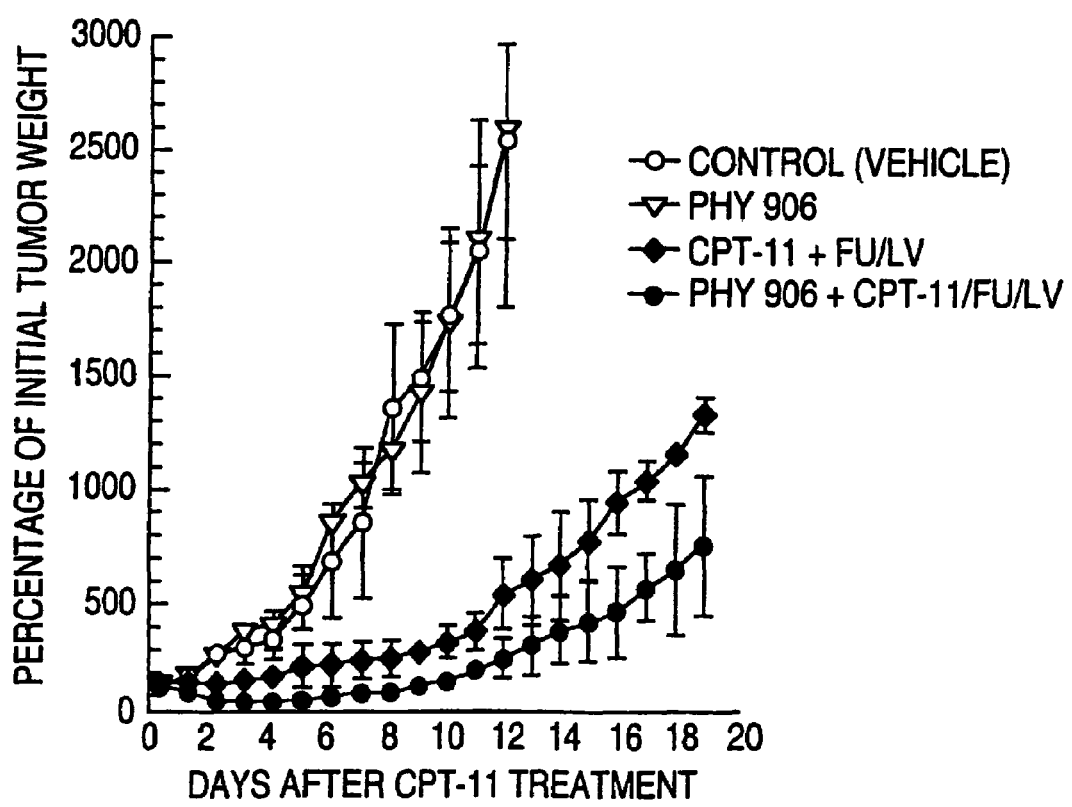
FIG. 9. Effect of PHY906 on Tumor Growth in CPT-11/FU/LV Treated BDF-1 Mice Bearing Colon 38 Tumor. Sequential administration of LV (100 mg/kg), CPT-11 (300 mg/kg) and FU (100 mg/kg) was given intraperitoneally during 1 hr period on day 0 only, as described in Materials and Methods. PHY906 was given orally 30 min after initial dose of LV on day 0 and continued twice a day for 4 days at 500 mg/kg (N=5 in each group).

The results indicate that PHY906 does not impair the antitumor efficacy of triple therapy at both 200 mg/kg and 300 mg/kg CPT-11, as shown in FIGS. 8 and 9, respectively. As depicted in FIG. 8, using 200 mg/kg CPT-11 in triple combination therapy, PHY906 slightly enhances tumor suppression at day 14 (p=0.045). At 300 mg/kg CPT-11, the enhancement of PHY906 in tumor suppression was not significant at day 14 (p=0.05), but was significant at day 21 (p=0.014), compared to groups receiving no PHY906 treatment. This result suggests that a longer time period may be needed to observe the enhancement of PHY906 on CPT-11/FU/LV tumor suppression. At the dose studied, PHY906 showed a similar beneficial effect on antitumor activity in triple combination therapy and CPT-11 treatment.

Figure 10:
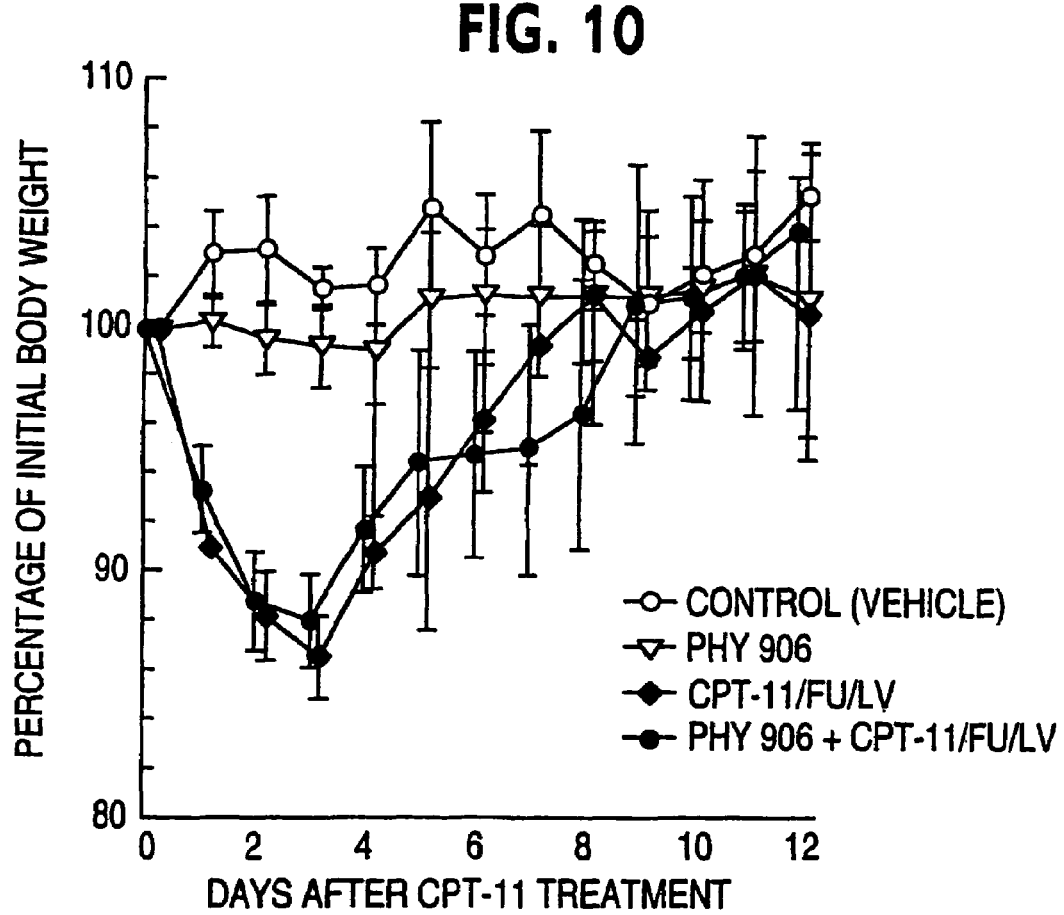
FIG. 10. Effect of PHY906 on Body Weight Change in CPT-11/FU/LV Treated BDF-1 Mice Bearing Colon 38 Tumor. Sequential administration of LV (100 mg/kg), CPT-11 (300 mg/kg) and FU (100 mg/kg) was given intraperitoneally during 1 hr period on day 0 only, as described in Materials and Methods. PHY906 was given orally 30 min after initial dose of LV on day 0 and continued twice a day for 4 days at 500 mg/kg (N=5 in each group).

At the doses used in the triple combination treatment, animals showed body weight loss. However, PHY906 did not slow weight loss during therapy, as shown in FIG. 10. In addition, PHY906 did not affect the recovery of body weight loss.

Example 9

Pharmacokinetics of CPT-11/FU/LV in BDF-1 Mice Bearing Colon 38 Tumor in the Presence and Absence of PHY906

Figure 18:
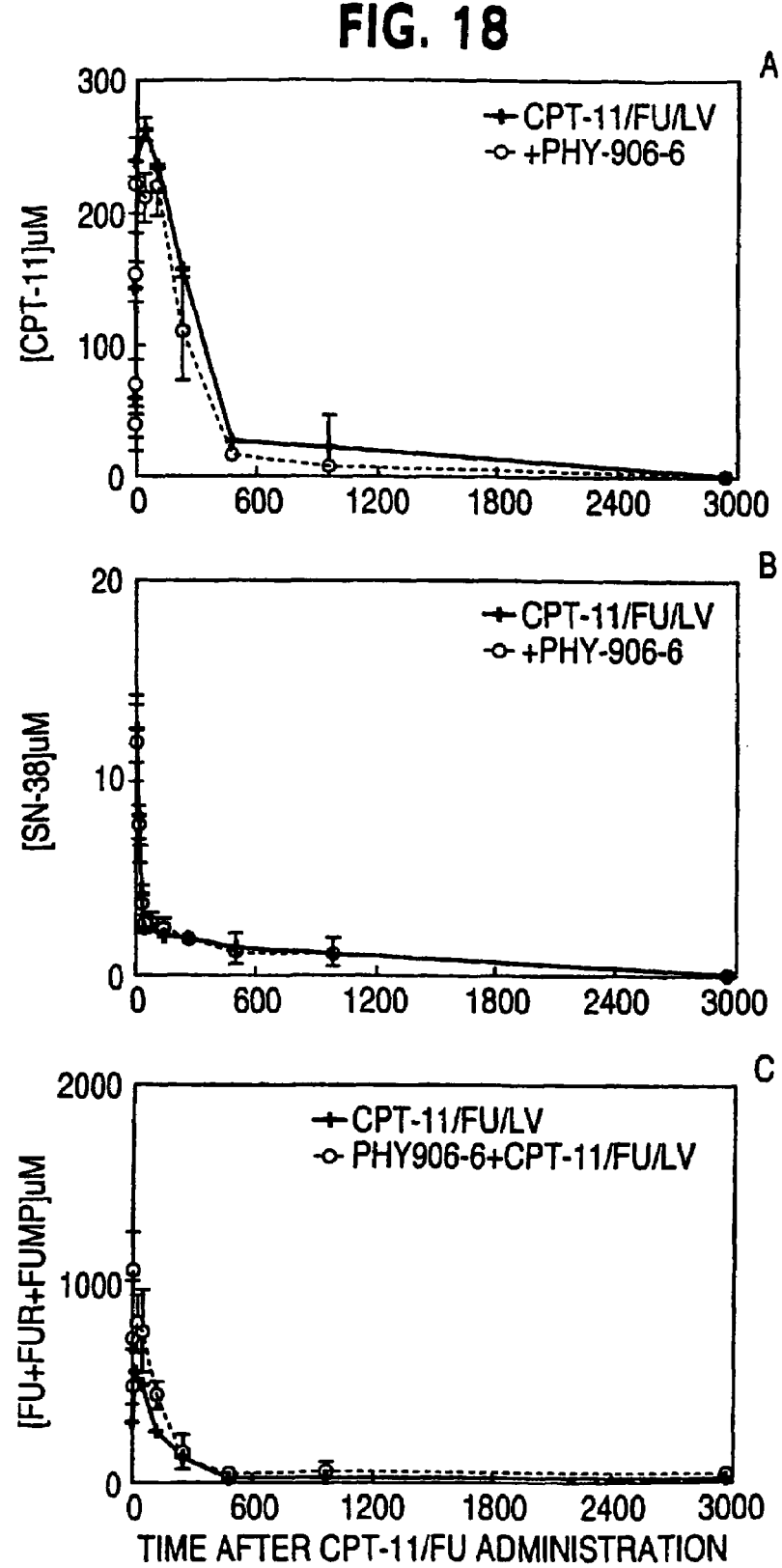
FIGS. 18A-C. Pharmacokinetics of CPT-11/FU/LV in Plasma. PHY906-6 is the Clinical Batch of PHY906. SN-38 is an active metabolite of CPT-11. FUR+FUMP are nucleoside and nucleotide metabolites of FU.
Figure 19:
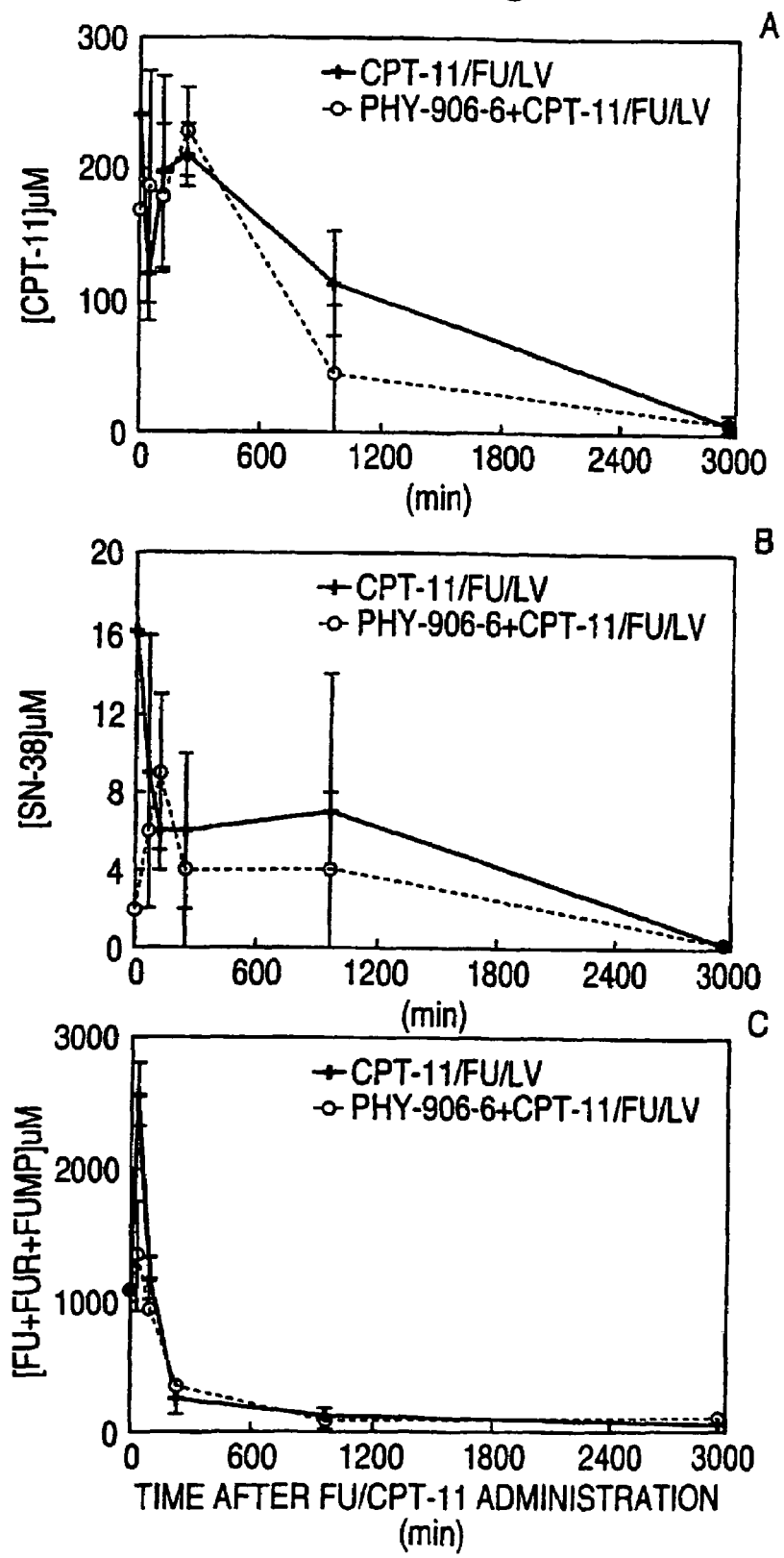
FIGS. 19A-C. Pharmacokinetics of CPT-11/FU/LV in Liver. PHY906-6 is the Clinical Batch of PHY906. SN-38 is an active metabolite of CPT-11. FUR+FUMP are nucleoside and nucleotide metabolites of FU.
Figure 20:
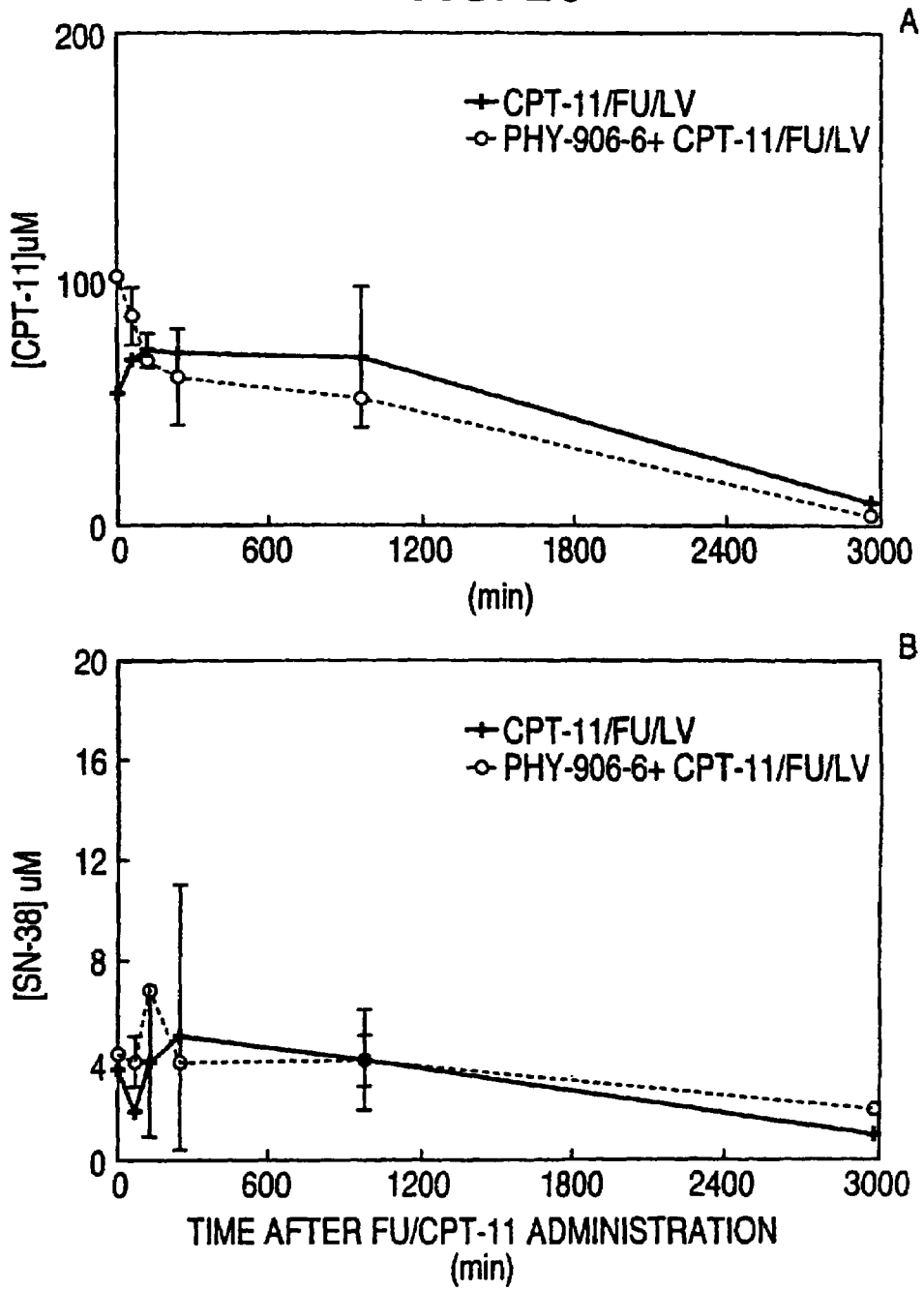
FIGS. 20A-B. Pharmacokinetics of CPT-11/FU/LV in Tumor. PHY906-6 is the Clinical Batch of PHY906. SN-38 is an active metabolite of CPT-11.

The pharmacokinetic data of CPT-11/FU/LV in BDF-1 mice bearing Colon 38 tumor in the presence and absence of PHY906 are shown in FIGS. 18-20. PHY906-6 is a clinical batch of PHY906, containing 10% excipient (starch).

The area under the curve (AUC) of CPT-11 in plasma increases after co-administration of PHY906 with the triple combination of CPT-11/FU/LV. There is no significant change of CPT-11 in either tumor or liver tissues after PHY906 co-administration.

SN-38, an active metabolite of CPT-11, remains unchanged in plasma, liver, or tumor.

The AUCs of FU and its nucleoside/nucleotide metabolites (FU+FUR+FUMP) in plasma or liver change after PHY906 co-administration with the triple combination of CPT-11/FU/LV.

Example 10

Effect of PHY906 on Antitumor Activity and Toxicity of CPT-11 in Human HepG2 Tumor-Bearing Nude Mice Results from the above Examples, specifically Examples 5, 7, and 8, indicate that PHY906 in combination with chemotherapeutic agents may potentiate the antitumor effects of chemotherapeutic agents and further retard tumor growth. Based upon the known pharmacological profiles of herbs contained in PHY906 (Table 1), it is speculated that the enhancing effects may act through immunological and/or hematological systems in normal mice. Therefore, experiments were designed to test the hypothesis in nude mice, which are deficient in immunological and hematological systems.

Figure 11:
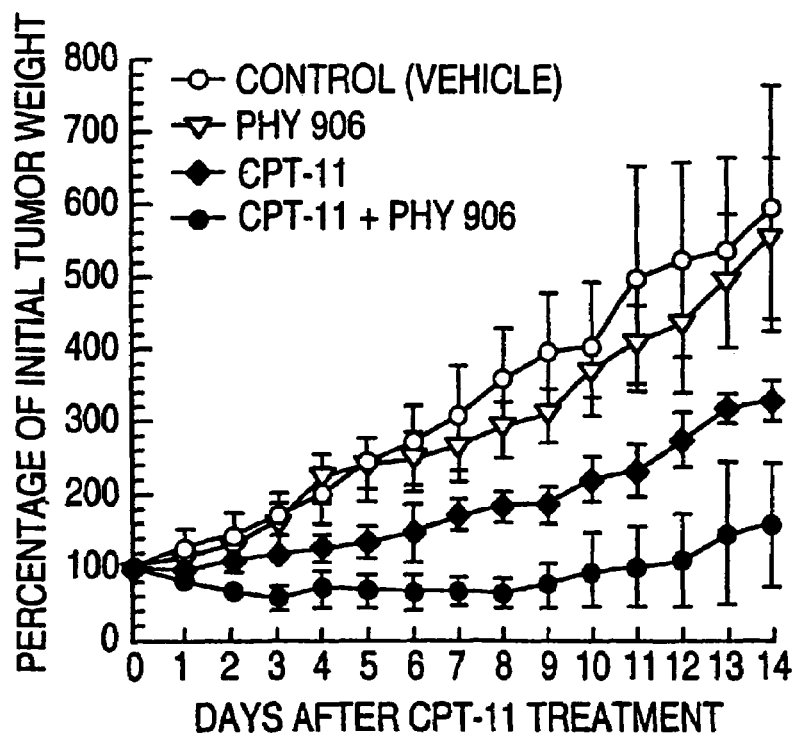
FIG. 11. Effect of PHY906 on the Tumor Growth in CPT-11 Treated NCr-Nude Mice Bearing Human HepG2 Tumor. CPT-11 (200 mg/kg) was given intraperitoneally on day 0 only. PHY906 was given orally 30 min before CPT-11 on day 0 and continued twice a day for 8 days at 500 mg/kg (N=5 in each group).
Figure 12:
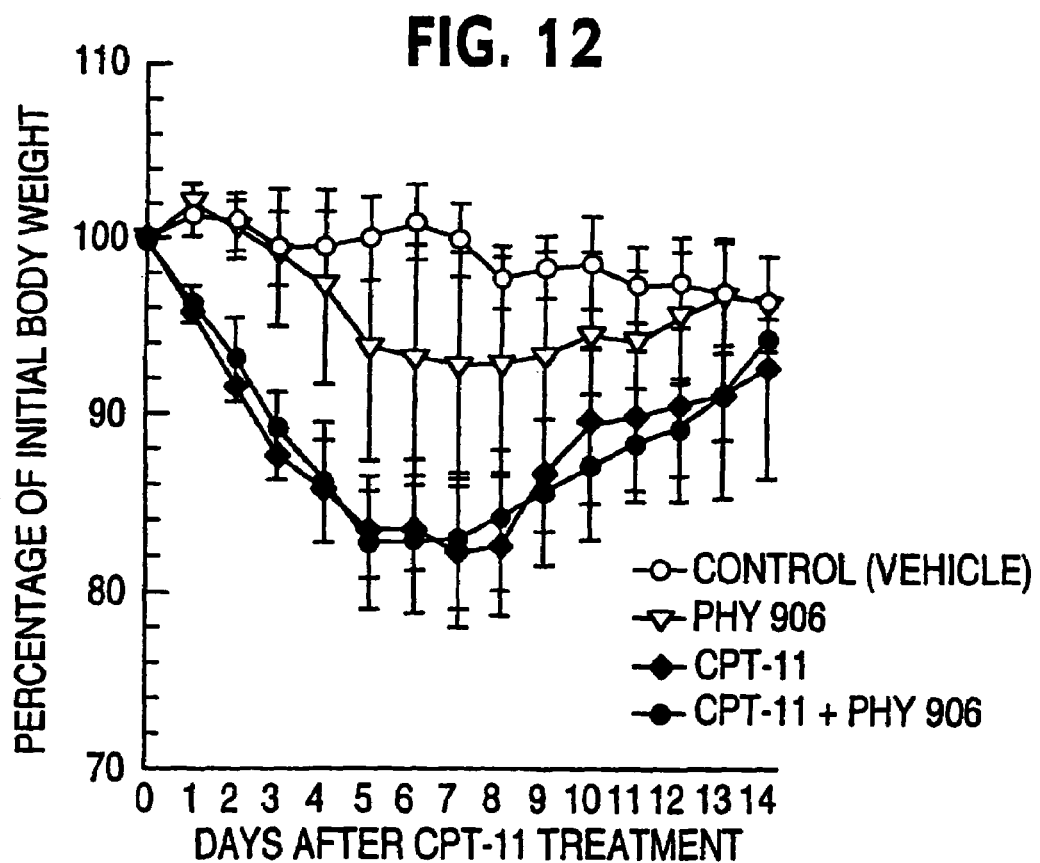
FIG. 12. Effect of PHY906 on the Body Weight in CPT-11 Treated NCr-Nude Mice Bearing Human HepG2 Tumor. CPT-11 (200 mg/kg) was given intraperitoneally on day 0 only. PHY906 was given orally 30 min before CPT-11 on day 0 and continued twice a day for 8 days at 500 mg/kg (N=5 in each group).

Human HepG2 tumor cells were implanted into NCr-nude mice to test the effect of PHY906 on the antitumor activity of CPT-11. Previous experiments showed that the maximum tolerable dose of CPT-11 in nude mice was 200 mg/kg, which was used in this study. CPT-11 (200 mg/kg, i.p.) was given on day 0. PHY906 was given twice daily at 500 mg/kg starting on day 0. As shown in FIG. 11, PHY906 did not compromise the antitumor effect of CPT-11 on human HepG2 xenografts in nude mice. However, unlike the observation in BDF-1 mice, PHY906 showed no beneficial effect on preventing body weight loss (FIG. 12) or animal death (data not shown) caused by CPT-11. The fact that PHY906 does not protect nude mice from weight loss as it does normal mice suggests that PHY906 exerts its effects through hematological and immunological systems, which nude mice lack.

Example 11

Effects of Different Chinese Herbal Formulations on Antitumor Effect of CPT-11, Body Weight Loss, and Survival in Mice Diarrhea is one of the dose-limiting toxicities among patients treated with cancer chemotherapeutic agents. In addition to PHY906, other anti-diarrhea medicines were examined. These included Chinese medicines, such as PHY-14ST, PHY-15ST, and PHY-915, as well as loperamide, currently recommended as the anti-diarrhea drug for CPT-11-induced late-onset diarrhea.

In addition to tumor growth inhibition and loss of body weight, we examined survival rates in mice receiving different herbal formulations in combination with a single bolus administration of CPT-11. Of the several formulations examined, PHY906 was the only one observed to enhance CPT-11 antitumor activity (Table 9), even though certain herbs contained in PHY906 are also present in the other herbal formulations. In the mortality study, PHY906 showed no statistical effect on animal death rates (P=0.044). Other anti-diarrhea medicines tested, such as PHY-14ST, PHY-15ST and loperamide, were observed to be completely ineffective in protecting against body weight loss or enhancing the antitumor effects of CPT-11. Surprisingly, PHY-915, was observed to decrease CPT-11 antitumor activity (Table 10).

TABLE 10

Effect of Different Herbal Formulations on CPT-11 Treated BDF-1 Mice Bearing Colon 38 Tumor.

| Herbal Formulation (1 g[c]/kg, bid, 8 days) | Protection from Body Weight Loss | P value[b,d] | Antitumor Effect | P value[b,e] | Animal Death[a] (Death/Total) |
|---|---|---|---|---|---|
| None | | | | | 7/40 |
| PHY906 | Significant | 0.0004 | Enhancement | 0.0027 | 0/24 |
| PHY14ST | No Change | 0.1072 | No Change | 0.2742 | 1[f]/10 |
| PHY15ST | No Change | 0.3259 | No Change | 0.6535 | 0/3 |
| PHY915 | Significant | 0.0306 | Decrease | 0.0885 | 0/5 |
| Loperamide | No Change | 0.9706 | No Change | 0.1595 | 3[g]/10 |

[a] All of the animals were observed for 14 days.
[b] The p values were calculated using the Student's paired t-test.
[c] based on the dry weight of formulations which contain excipient.
[d] Calculated on the day that CPT-11 - treated mice reached maximum body weight loss.
[e] Calculated on the tumor size at day 6 after initial drug treatment.
[f] One mouse died on day 6.
[g] Mice died on day 3 (N = 1), 4 (N = 1) and 5 (N = 1).

Example 12

Cytotoxicity of PHY906 in Different Cell Lines

To evaluate in vitro cell models as measures of quality assurance, the effects of two different preparations of PHY906 (PHY906A and PHY906B) on the growth inhibition of different human tumor cell lines and mouse Colon 38 tumor cell lines were studied. As shown in Table 11, PHY906A and PHY906B showed no significant difference in growth inhibitory activities among the cell lines. Of note, HepG2 cell lines were found to be more sensitive to PHY906 than other human cell lines.

TABLE 11

Cytotoxicity of PHY906 in Different Cell Lines.

| Herbal Formulation[b] | $IC_{50}$ (mg/ml)[a] | | | | |
|---|---|---|---|---|---|
| | KB | HepG2 | CEM | HCT116 | Colon 38 |
| PHY906A | 0.67 ± 0.26 | 0.14 ± 0.08 | 0.73 ± 0.17 | 0.65 | 0.08 ± 0.02 |
| PHY906B | 0.90 ± 0.5 | 0.09 ± 0.06 | 0.64 ± 0.01 | 0.6 | 0.07 ± 0.02 |

[a]Based on the dry weight of aqueous extract of raw herbs.
[b]Different research batch of PHY906.

The results of the above experiments suggest that PHY906 reduces some host toxicities induced by treatments of CPT-11, FU/LV, or the triple combination therapy with CPT-11/FU/LV. The botanical drug PHY906 not only maintains, but also potentiates, the antitumor activity of the chemotherapeutic agents tested. Indeed, PHY906 enhances the therapeutic index of CPT-11, FU/LV and CPT-11/FU/LV by increasing the overall antitumor activity in both Colon 38 tumor-bearing mice and human Hep G2 xenografts in nude mice. These observations were tested with several anticancer agents in two different tumor models (FIGS. 3, 6, 8, 9, and 11).

Example 13

Effect of PHY906 on Tumor Growth in Colon 38 Inoculated Mice Treated with L-OddC PHY906 was evaluated as a modulator of L-OddC (beta-L-Dioxolane-cytidine) therapy for tumor growth in mice inoculated with Colon 38 tumor cells. Mice were subjected to a subcutaneous injection of murine Colon 38 tumor cells. Seven days after inoculation of the cancer cells, mice were treated with L-OddC (25 mg/kg) intraperitoneally and oral administration of PHY906 (500 mg/kg, b.i.d.). The animals were then administered only with the same dose of PHY906 continuously for the rest of the experiment.

Figure 13:
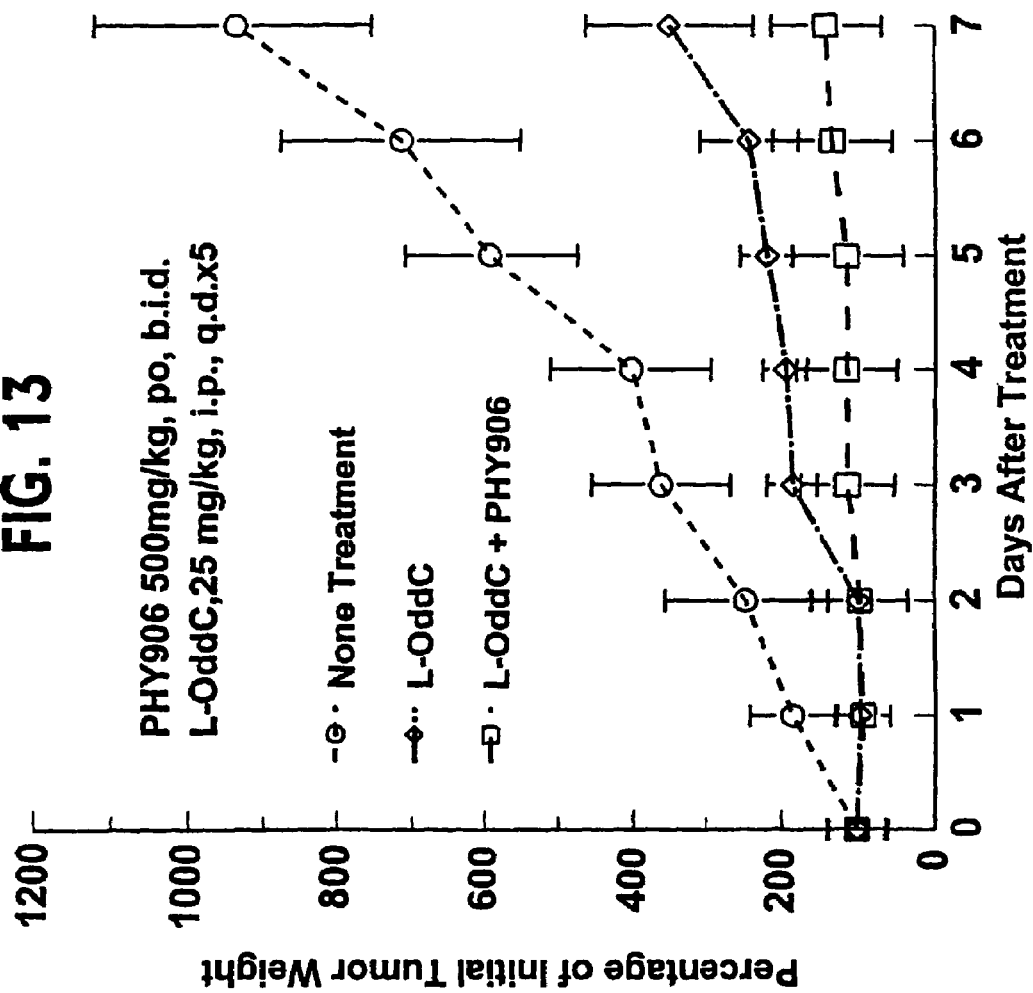
FIG. 13. Antitumor Effect of L-OddC with PHY906 on Colon 38 Bearing BDF-1 Mice. Female BDF-1 mice (8-10 weeks old, average weight about 20 g) were injected subcutaneously with Colon 38 tumor cells. L-OddC (beta-L-Dioxolane-cytidine 25 mg/kg, q.d.X5) was injected intraperitoneally starting on day zero for 5 consecutive days. PHY906 was administered orally (1 g/kg, b.i.d.) on day zero and on a daily basis until the completion of the experiment (q.d. is an abreviation for "quaque die" which means once a day, q.d. X5 means each one of five mice received the dose once a day for 5 consecutive days; b.i.d. is an abbreviation for "bis in die", which means twice a day). (N=5 in each group).

As shown in FIG. 13, treatment with L-OddC demonstrates that PHY906 neither impedes nor impairs the antitumor efficacy of the L-OddC. In fact, the data suggest that this herbal medicine may actually enhance L-OddC anti-tumor activity.

Thus, these results suggest that the herbal PHY906 can be used as a modulator for L-OddC chemotherapy to significantly improve and alleviate the toxic side effects without compromising the anti-tumor efficacy of the L-OddC.

Example 14

Effect of PHY906 on Tumor Growth in Colon 38 Inoculated Mice Treated with VP-16

PHY906 was evaluated as a modulator of VP-16 (etoposide, a topoisomerase II inhibitor) therapy for tumor growth in mice inoculated with Colon 38 tumor cells. Mice were subjected to a subcutaneous injection of murine Colon 38 tumor cells. Seven days after inoculation with the cancer cells, mice were treated with VP-16 (25 mg/kg) intraperitoneally and oral administration of PHY906 (500 mg/kg, b.i.d.). The animals were then administered only with the same dose of PHY906 continuously for the rest of the experiment.

Figure 14:
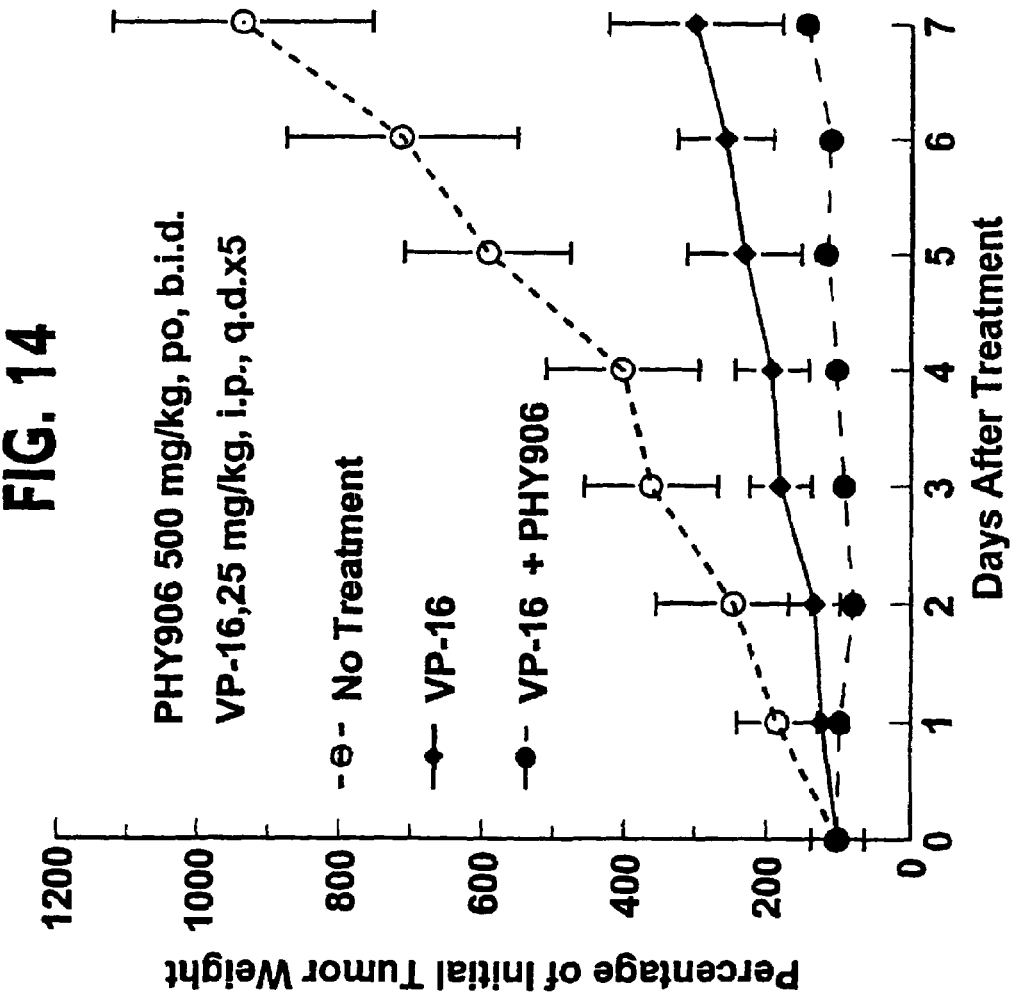
FIG. 14. Antitumor Effect of VP-16 with PHY906 on Colon 38 Bearing BDF-1 Mice. Female BDF-1 mice (8-10 weeks old, average weight about 20 g) were injected subcutaneously with Colon 38 tumor cells. VP-16 (etoposide 25 mg/kg, q.d.X5) was injected intraperitoneally once a day on day 0 and for 5 consecutive days. PHY906 was administered orally (1 g/kg, b.i.d.) on day 0 and on a daily basis until the completion of the experiment. (N=5 in each group).

As shown in FIG. 14, treatment with VP-16 demonstrates that PHY906 neither impedes nor impairs the antitumor efficacy of the VP-16. In fact, the data suggest that this herbal medicine may actually enhance VP-16 anti-tumor activity.

Thus, these results suggest that the herbal PHY906 can be used as a modulator for VP-16 chemotherapy to significantly improve and alleviate the toxic side effects without compromising the anti-tumor efficacy of the VP-16.

Example 15

Effect of PHY906 on Tumor Growth in Colon 38 Inoculated Mice Treated with 5-Fluorouracil PHY906 was evaluated as a modulator of 5-fluorouracil (FU) therapy for tumor growth in mice inoculated with Colon 38 tumor cells. Mice were subjected to a subcutaneous injection of murine Colon 38 tumor cells. Seven days after inoculation of the cancer cells, mice were treated with 5-fluorouracil at two doses (250 mg/kg, one dose on day 0, or 30 mg/kg daily dose given from day 0 to day 4) intraperitoneally, and with PHY906 (500 mg/kg, b.i.d.) by oral administration. The animals were then administered only with the same dose of PHY906 continuously for the rest of the experiment.

Figure 15:
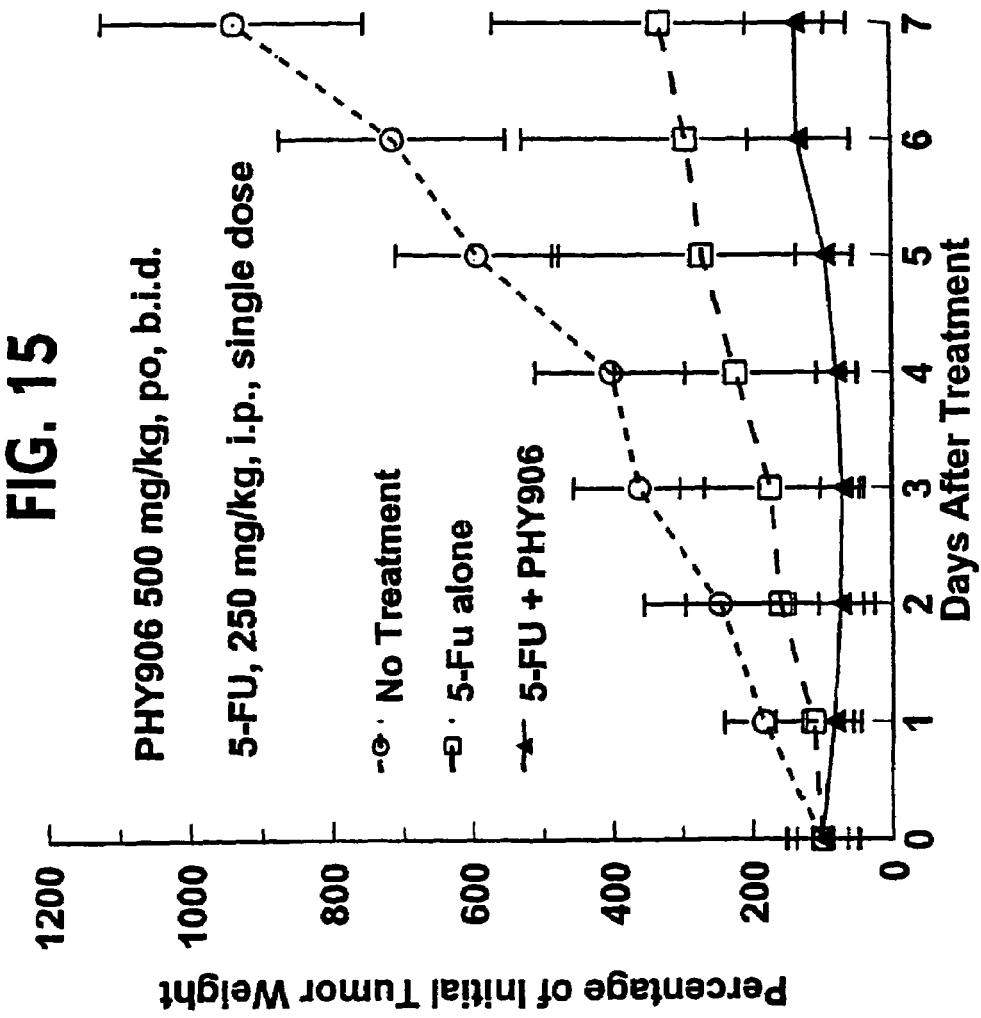
FIG. 15. Antitumor Effect of 5-Fluorouracil (FU) with PHY906. Five female BDF-1 mice (8-10 weeks old, average weight about 20 g) were injected subcutaneously with Colon 38 tumor cells. Only one dose of FU (250 mg/kg) was injected intraperitoneally on day zero. PHY906 was administered orally (1 g/kg, b.i.d.) on day zero and on a daily basis until the completion of the experiment. (N=5 in each group).
Figure 16:
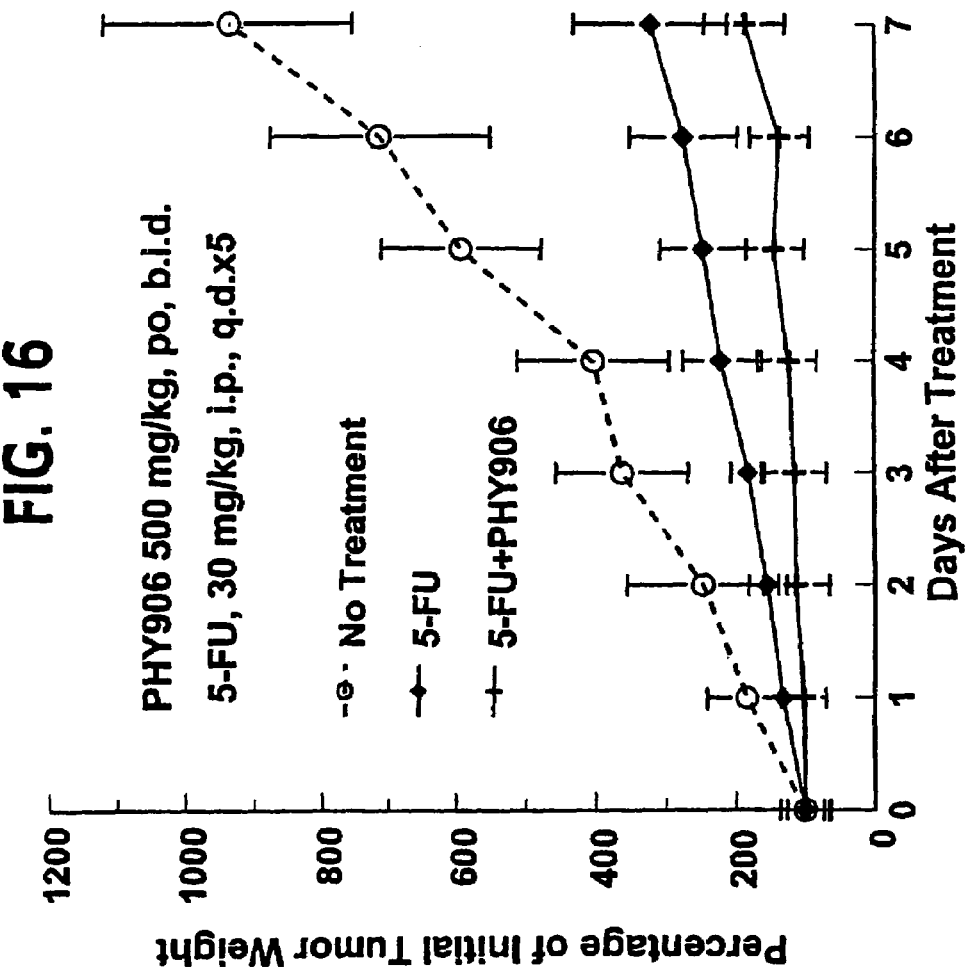
FIG. 16. Antitumor Effect of 5-Fluorouracil (FU) with PHY906. Female BDF-1 mice in each group (8-10 weeks old, average weight about 20 g) were injected subcutaneously with Colon 38 tumor cells. FU (30 mg/kg, q.d. ×5) was injected intraperitoneally daily for 5 consecutive days starting on day 0. PHY906 was administered orally (1 g/kg, b.i.d.) on day 0 and on a daily basis until the completion of the experiment. (N=5 in each group).

As shown in FIGS. 15 and 16, treatment with 5-fluorouracil demonstrates that PHY906 neither impedes nor impairs the antitumor efficacy of the 5-fluorouracil. In fact, the data suggest that this herbal medicine may actually enhance 5-fluorouracil anti-tumor activity.

Thus, these results suggest that the herbal PHY906 can be used as a modulator for 5-fluorouracil chemotherapy to significantly improve and alleviate the toxic side effects without compromising the anti-tumor efficacy of the 5-fluorouracil.

Example 16

Effect of PHY906 on Tumor Growth in Colon 38 Inoculated Mice Treated with CPT-11 and Loperamide PHY906 was evaluated as a modulator of CPT-11 therapy for tumor growth in mice inoculated with Colon 38 tumor cells in the presence of anti-diarrhea medication Loperamide. Mice were subjected to a subcutaneous injection of murine Colon 38 tumor cells. Seven days after inoculation of the cancer cells, mice were treated with CPT-11 (400 mg/kg, i.p.), alone, in the presence of orally administered of PHY906 (500 mg/kg, b.i.d.), or in the presence of Loperamide (2 mg/kg, p.o., b.i.d.).

Figure 17:
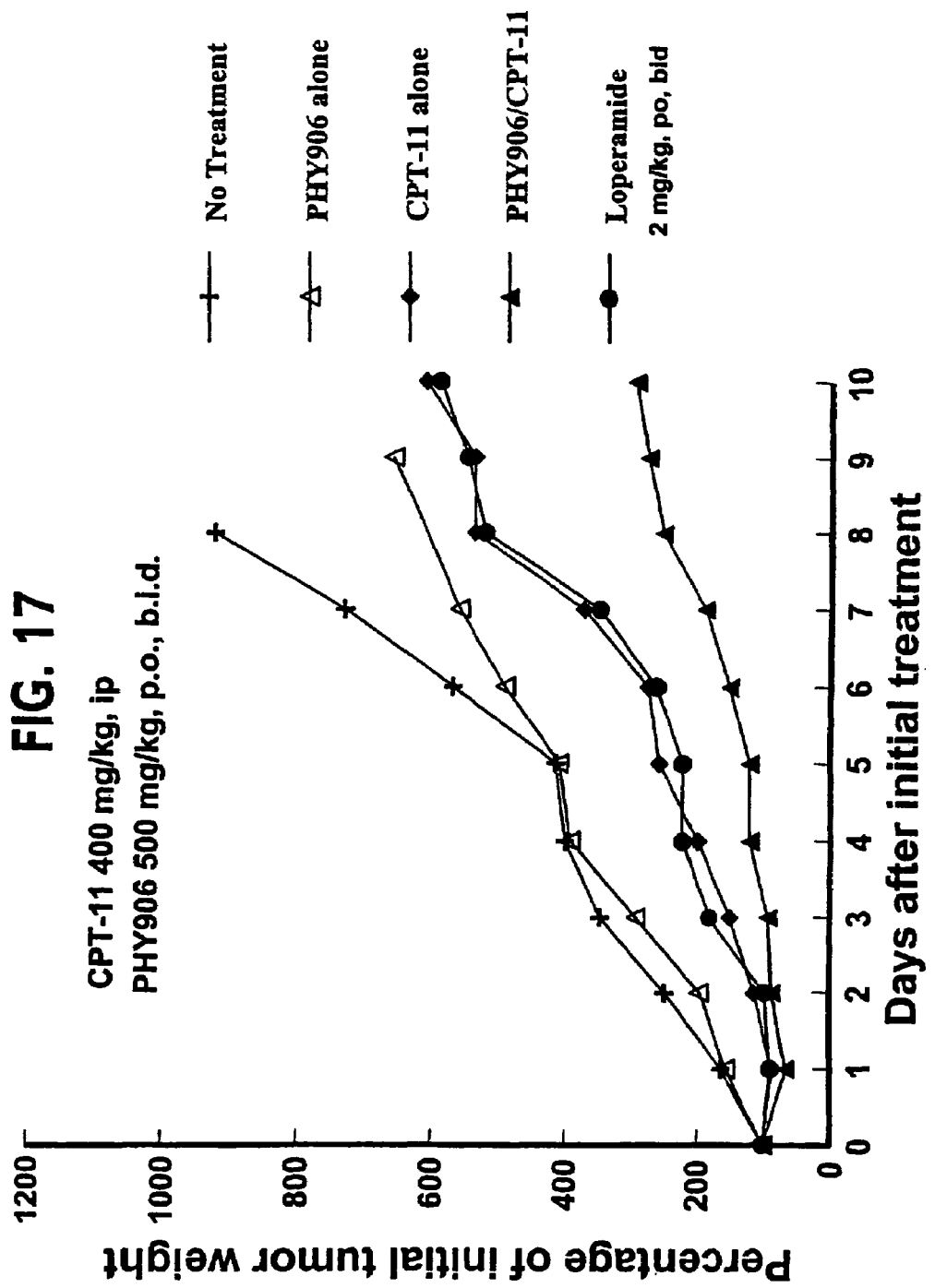
FIG. 17. Antitumor Effect of CPT-11 with PHY906 Versus Loperamide on Colon 38 Bearing BDF-1 Mice. Female BDF-1 mice (8-10 weeks old, average weight about 20 g) were injected subcutaneously with Colon 38 tumor cells. Mice either received no treatment, PHY906 alone, CPT-11 alone, CPT-11 and PHY906, or loperamide alone. The PHY906 and CPT-11 were administered as set forth in FIG. 3. Only one dose of loperamide was given orally (2 mg/kg, p.o. (oral administration), b.i.d.) on day zero. (N=5 in each group).

FIG. 17 compares the antitumor effect of PHY906 and Loperamide. As shown in FIG. 17, CPT-11 in the presence of PHY906 is more effective at reducing tumor growth (as determined as a percentage of initial tumor weight) than Loperamide.

These preliminary results suggest that the herbal PHY906 is more effective than standard administration of Loperamide for delayed CPT-11 induced diarrhea.

Example 17

To Determine the Minimal Effective Dose (MED) and the Optimal Duration of PHY906 Administration When Given in Combination with Irinotecan Introduction: Several studies indicate that Kampo medicine, which consists of seven herbs, is effective in preventing the occurrence of CPT-11-induced diarrhea in animals and in reducing the severity of CPT-11-induced diarrhea in vivo (Mori, 1998).

PHY906 has also been evaluated in an in vivo animal model and has been shown to reduce the severity of irinotecan-induced toxicity. Accordingly, based on a long historical experience (1500 years) demonstrating safety in humans, the promising preclinical activity of this compound in an animal model, and the potential activity noted for a related herbal compound in this setting, a study can be conducted to evaluate the effect of PHY906 on the severity of chemotherapy-induced toxicities, such as weight loss, diarrhea, overall performance status, and quality of life, and on the anti-tumor activity of irinotecan or other drugs in patients with refractory advanced colorectal cancer.

This study includes patients with histologically confirmed, FU-refractory, advanced colorectal cancer. Measurable or evaluable disease is not required. Patients with central nervous system (CNS) metastases are eligible provided the CNS disease has remained stable for at least 4 weeks following completion of surgery, chemotherapy, and/or radiation therapy.

Participants in the study will be ≧18 years of age and will have no significant underlying medical diseases. All patients will have a performance status of ECOG 0-2, a life expectancy of at least 3 months, and have given informed consent. (ECOG is an abbreviation for "Eastern Cooperative Oncology Group. ECOG 0=patient performing normal activity; ECOG 1=patient having minimal symptoms; ECOG 2=to patient spents <50% of time in bed; ECOG 3=patient spents>50% time spent in bed; ECOG 4=patient is bed bound.) Patients must have fully recovered from the effects of any prior surgery and have not received wide-field radiation or any chemotherapy within 4 weeks (6 weeks for nitrosoureas or mitomycin C) of entry onto this study. An ANC (absolute neutrophil count)≧1500 /µl, platelet count≧40 ml/min, and a total bilirubin≦2.0 mg/dl is required for entry onto study.

Pretreatment Evaluation: Prior to the start of treatment, all patients will have a complete history, physical examination, and a determination of their performance status. The laboratory studies will include a complete blood count (CBC) with differential, a serum albumin, electrolytes, glucose, blood urea nitrogen (BUN), creatinine, serum calcium and magnesium, liver function tests, prothrombin and partial thromboplastin time, and a urinalysis.

Treatment: Irinotecan will be reconstituted from a lyophilized powder into 2 ml of sterile water, diluted in 100 ml of D5W (5% Dextrose in water), and administered over 90 min at a dose of 125 mg/m$^2$. Irinotecan chemotherapy will be administered on a weekly schedule for 4 weeks with a 2 week rest period in the outpatient clinic at each of the participating hospitals.

PHY906 will be taken on an empty stomach 30 min prior to meals. On chemotherapy treatment days, the first dose will be taken before the administration of irinotecan.

PHY906 will be administered orally three times a day before each meal starting at an initial dose of 0.60 g. (total daily dose, 1.80 gm/day). The dose of PHY906 that is presently being used by patients in the Orient is 7.2 gm/day, and to date, no adverse events have been observed. Thus, the dose that is proposed to start out this trial is ¼th the usual dose of the herbal medicine. PHY906 will be given for an entire 4-week course of chemotherapy along with irinotecan with a 2-week rest. A minimum of three patients will be treated at this initial dose level of PHY906. Once the 3 patients have completed a full 6-week cycle, if 0 of 3 patients experience dose-limiting toxicity (DLT), then the next higher dose will be used for the subsequent group of 3 patients. In all patients, pharmacokinetic studies will be performed 24 hr after the start of the first cycle of chemotherapy.

If 1 of 3 patients experience DLT, then 3 more patients will be treated at the same dose level. If ≦1 of the next 3 experience DLT (1 or 2 of 6 total patients), the dose will be escalated to the next dose level except when those events occur during the doubling scheme, when the next escalation will be to level n+1 on the modified Fibonacci scheme (Table 12).

TABLE 12

Dose Escalation Schedule of PHY906.

| Dose Level | Escalation | Total Dose (gm/day) |
|---|---|---|
| 1 | Starting | 1.8 |
| 2 | 2 × level 1 | 3.6 |
| 3 | 2 × level 2 | 7.2 |

Once the 7.2 gm/day dose level is reached and no ≧ grade 2 toxicity is observed at this level "n" a modified Fibonacci escalation as shown below will be performed.

| N + 1 | 1.5 × level n |
| N + 2 | 1.33 × level n + 1 |
| N + 3 | 1.25 × level n + 2 |

All subsequent levels: 25% increments until the maximum tolerated dose is reached.

Dose Escalation Schedule of PHY906: If clinically indicated and considered necessary by the Principal Investigators, a lower dose level, rather than the level specified above, may be utilized.

The rate of subject entry and escalation to the next dose regimen will depend upon assessment of the safety profile of patients entered at each dose level. Toxicity will be evaluated and graded according to the NCI Clinical Trial Guidelines (CTG) Expanded Common Toxicity Criteria.

The antiemetic schedule for this protocol will consist of 1-2 mg of granisetron admixed in 50 ml normal saline and administered via ½ hr prior to chemotherapy on each treatment day. The antiemetics (administered intravenously or orally) will be repeated every 8 hr as needed to control nausea and/or vomiting. Treatment will be repeated every week for 4 consecutive weeks followed by a 2-week rest. This will constitute one cycle of therapy.

Diarrhea that occurs during or shortly after irinotecan infusion will be treated with atropine (0.5-1 mg) intravenously. For diarrhea occurring≧12 hr after irinotecan administration, patients will be treated with loperamide 4 mg orally at the first sign of diarrhea followed by 2 mg orally every 2 hr (4 mg orally every 4 hr at night) until there is complete resolution of the diarrhea for at least 12 hr. If the diarrhea is bloody, associated with fevers≧101.6° F., and continues unabated for ≧12 hr, the patient will be admitted to the hospital for further evaluation and treatment.

Dose Modification of Irinotecan: There will be no dose escalation of irinotecan in this study. Dose modification for toxicity will be made as recommended in the package insert provided by the manufacture (Table 13).

Table 13. Recommended Dose Modifications for the Weekly and Once-Every 3-Week Schedule. A new course of therapy should not begin until the granulocyte count has recovered to ≧1500/mm$^3$, and the platelet count has recovered to ≧100,000/mm$^3$, and treatment-related diarrhea is fully resolved. Treatment should be delayed 1 to 2 weeks to allow for recovery from treatment-related toxicities. If the patient has not recovered agter a 2 week delay, consideration Should be given to discontinuing Camptosar® (irinotecan, CPT-11).

Response and Toxicity Assessment: Toxicity will be assessed by weekly physical examination and blood counts and graded according to National Cancer Institute Common Toxicity Criteria. These evaluations and a complete chemistry profile will be repeated before each treatment.

Patients will also keep a daily record of their bowel habit and their use of anti-motility agents. This diary will include the time of ingestion of PHY906, a recording of the frequency and consistency of their bowel movements (formed, loose, or watery), and the anti-motility treatment which was used by the patient to manage this symptom.

A research nurse will contact each patient at least once a week between visits during the first cycle to reinforce instructions on the management of diarrhea and the completion of the diary. Overall quality of life including asthenia, nausea, vomiting, and loss of appetite will also be evaluated using established FAST methodology.

TABLE 13

Recommended Dose Modifications for the Weekly and Once-Every 3-Week Schedule. A new course of therapy should not begin until the granulocyte count has recovered to ≧1500/mm$^3$, and the platelet count has recovered to ≧100,000/mm$^3$, and treatment-related diarrhea is fully resolved. Treatment should be delayed 1 to 2 weeks to allow for recovery from treatment-related toxicities. If the patient has not recovered after a 2 week delay, consideration should be given to discontinuing Camptosar® (irinotecan,CPT-11).

| Weekly Toxicity | | At the Start of the Next Courses of Therapy (After Adequate Recovery), Compared with the Starting Dose in the Previous Course[a] | |
|---|---|---|---|
| NCI Grade[b] Value | During a Course of Therapy Weekly | Weekly | Once every 3 weeks |
| No toxicity | Maintain dose level | ↑ 25 mg/m$^2$ up to a maximum dose of 150 mg/m$^2$ | 1 Maintain dose level |
| Neutropenia | | | |
| 1 (1500 to 1999/mm$^3$) | Maintain dose level ↓ 25 mg/m$^2$ | Maintain dose level Maintain dose level | Maintain dose level |
| 2 (1000 to 1499/mm$^3$) | Omit dose, then ↓ 25 mg/m$^2$ when resolved to ≦ grade 2 | ↓25 mg/m$^2$ | Maintain dose level |
| 3 (550 to 999/mm$^3$) | Omit dose, then ↓ 50 mg/m$^2$ when resolved to ≦ grade 2 | ↓50 mg/m$^2$ | ↓25 mg/$^2$ |
| 4 (<500/mm$^3$ | | | ↓50 mg/m$^2$ |
| Neutropenic fever (grade 4 neutropenia &≧ grade 2 fever) | Omit dose, then ↓ 50 mg/m$^2$ when resolved | ↓ 50 mg/m$^2$ | ↓ 50 mg/m$^2$ |
| Other hematologic Toxicities | Dose modifications for leukopenia, thrombocytopenia, and also based on NCI toxicity criteria and are the same at the start of subsequent courses of therapy are recommended for neuropenia above. | | |
| Diarrhea | | | |
| 1 (2-3 stools/day > pretx[c]) | Maintain dose level | Maintain dose level | Maintain dose level |
| 2 (4-6 stools/day > pretx[c]) | ↓ 25 mg/m$^2$ | Maintain dose level | Maintain dose level |
| 3 (7-9 stools/day > pretx[c]) | Omit dose, then ↓ 25 mg/m$^2$ when resolved to ≦ grade 2 | ↓ 25 mg/m$^2$ | Maintain dose level |
| 4 (= 10 stools/day > pretx[c]) | Omit dose, then ↓ 50 mg/m$^2$ when resolved to ≦ grade 2 | ↓ 50 mg/m$^2$ | ↓ 50 mg/m$^2$ |
| | | | ↓ 50 mg/m$^2$ |
| Other nonhemalogic Toxicities | | | |
| 1 | | Maintain dose level | Maintain dose level |
| 2 | | Maintain dose level | Maintain dose level |
| 3 | | ↓25 mg/m$^2$ | Maintain dose level |
| 4 | | ↓50 mg/m$^2$ | ↓25 mg/m$^2$ |

[a]All dose modifications should be based on the worst preceding toxicity
[b]National Cancer Institute Common Toxicity Criteria
[c]Pretreatment A pill count will be made by a pharmacist to each clinical visit for treatment to assess compliance with PHY906. An evaluation of disease response will be made after every two treatment cycles. Response will be defined according to ECOG criteria and will be assessed in all patients with measurable or evaluable disease but will not constitute an endpoint in this study.

Pharmacokinetics of Irinotecan: In selected patients, pharmacokinetic studies will be performed to assess whether PHY906 affects the metabolism and elimination of irinotecan. In these patients, the first dose of irinotecan will be given alone (cycle 1/day 1) and the PHY906 will begin on day 2.

Blood samples will be collected in heparinized tubes immediately before irinotecan administration, 30, 60, 90 min during the infusion of irinotecan and 0.5, 1.5, 3.5 and 6 h after the end of the infusion on cycle 1, day 1, and on cycle 1 day 8. Samples will be immediately processed with 2.50 µl of plasma added to 500 µl of internal standard solution in polystyrene tubes. The internal standard solution will consist of camptothecin 50 µg/ml in acetonitrile acidified with glacial acetic acid, 4.0 ml in 100 ml. The samples will be vortexed for 30 sec, placed into a 40° C. water bath for 15 min, cooled at room temperature and then mixed with 900 µl of a 25 mM triethylamine buffer (pH 4.2). The supernatant will be transferred to 1.5 ml Eppendorf tubes, centrifuged for 4 min at 13,000×g in a microcentrifuge, and an aliquot of the clear supernatant is analyzed by high performance liquid chromatography (HPLC).

Chromatographic analysis will be conducted on a Microsorh C18 (4.5×250 mm, 5 µm particle size) reverse phase HPLC column eluted with 72:28 (v/v) 25 mM TEA/acetonitrile buffer at 1 ml/min utilizing a fluorescence detector with $\lambda EX$ 372 nm and $\lambda Em$ 535 nm (Pharmacia & Upjohn SOP #UPJ-120-5). Maximum plasma concentration, terminal half-life, and AUC (area under the curve) will be determined by non-compartmental analysis of the data utilizing PC-NONLIN software (Scientific Consulting Lexington, Ky.) and standard pharmacokinetic equations. The Pharmacokinetic studies will be performed on, cycle 1/day 1 and cycle 1/day 8, to determine whether prolonged exposure to PHY906 produces a cumulative effect on the plasma clearance of irinotecan.

Example 18

Effect of PHY906 on Pacreatic Cancer, Hepatocellular Carcinoma, and Colorectal Cancer A. Materials and Methods Drugs: Gemcitabine HCl (Gemzar®) was purchased from Eli Lilly and company (Indianapolis, Ind.). $^3$H-Gemcitabine (14 Ci/mmol, 1 mCi/ml in 50% EtOH) was purchased from Moravek Biochemicals, Inc. (Brea, Calif.). Tetrahydrouridine (THU) was purchased from Calbiochem (San Diego, Calif.). 3'-Azido-3'-deoxythymidine (AZT) and 5-flurouracil (5-FU) were purchased from Sigma Chemical Co. (St. Louis, Mo.). Capecitabine (Xeloda®, CAP) was purchased from Roche Laboratories Inc. (Nutley, N.J.). The clinical batch of PHY906 (PHY906-6, FDA 165542) with 10% excipient was prepared by Sun Ten Pharmaceutical, Inc. (Taipei, Taiwan). The PHY906 formula is composed of four herbs: *Scutellariae baicalensis Georgi, Paeonia lactiflora Pall., Ziziphus jujuba Mill* and *Glycyrrhiza uralensis Fisch.*, with a relative weight ratio of 3:2:2:2. The non-clinical batch 906MT with unkown amounts of excipient was purchased from Min Tong Pharmaceutical Co., Ltd. (Taichung, Taiwan).

Mice: Female BDF-1 and C57BL/6 mice with body weights between 16 and 20 g (4-6 weeks old) were purchased from Charles River Laboratories (Wilmington, Mass.). Male NCr athymic nude mice with body weight between 16 and 20 g (4-6 weeks old) were purchased from Taconic Farms (Garmantown, N.Y.). The mouse pancreas tumor PAN02 was purchased from the NCI-Frederick Cancer Research Facility (Frederick, Md.).

Preparation of Gemcitabine solution: Reconstituted 200 mg of Gemcitabine HCl powder with 6.66 ml of PBS (phosphate buffered saline) to final concentration of 30 mg/ml.

Preparation of $^3$H-Gemcitabine solution: Ten microliters (10 µCi) of $^3$H-Gemcitabine was dried under a Speedvac to remove ethanol, then mixed with 250 µl of 30 mg/ml gemcitabine to get a final solution with radiospecificity of 0.4 mCi/mmol. The final concentration of this $^3$H-Gemcitabine solution was 30 mg/ml.

Preparation of capecitabine solution from capecitabine tablet: Capecitabine (150 mg/tablet) was dissolved in 40 mM citrate buffer (pH 6.0) containing 5% gum arabic as the vehicle. The final solution contains 36 mg/ml of capecitabine.

Preparation of Herbal Extract From Dry Powder: The preparation of the herbal extract followed SOP#HERB-001-PHY906. Briefly, one gram of different batches of PHY906 dry powder, containing 10% (clinical batch of PHY906) starch excipient, was added to 10 ml of 80° C. H$_2$O and incubated at 80° C. for 30 minutes. The supernatant was separated from the debris by centrifugation (2060 g, 15 min) at room temperature. The concentration of PHY906 supernatant was calculated as 90 mg/ml for clinical batch of PHY906 (1 g/10 ml×0.9), based on the dry weight of the dry powder. Since the excipient amount of 906MT was unknown, the concentration of this preparation was considered as 100 mg/ml. The herbal extract was diluted to 50 mg/ml with water, stored at room temperature, and used within 24 hours. Any residual precipitant that occurred upon standing was vortexed into a suspension and used to treat the animals.

Tumor Cells: The human hepatocellular carcinoma HepG2, human PANC-1 pancreatic cancer and mouse Colon 38 colorectal cancer cell lines were purchased from the American Type Culture Collection (Rockville, Md.). The HepG2 and Colon 38 cell lines were routinely grown in MEME media while PANC-1 cell line was grown in DMEM media, supplemented with 10% fetal bovine serum (FBS). Small chunk of mouse PAN02 tumor from NCI was suspended in PBS solution as a total volume of 0.8 ml. The cells were implanted into the left flank of mice. Tumor transplantation from mice to mice was performed when the tumor reached 1500-2000 mm$^3$.

Mouse Tumor Model: Tumor cells (5×10$^6$ cells in 0.1 ml PBS) were transplanted subcutaneously into the left flank of mice. After 14 days, tumor ranging in size from 300-500 mm$^3$ was selected for drug studies. The length and width of the each tumor was measured with sliding calipers. The tumor size was estimated according to the following formula:

Tumor size (mm$^3$)=length (mm)×width (mm)$^2$/2.

The studies were conducted and the animals were maintained at the Yale Animal Facility Antitumor Activity of Chemotherapeutic Agents in the Presence or Absence of PHY906: A total of 20 tumor-bearing mice were divided into 4 groups (N=5 mice/group):

1) Vehicle

2) PHY906

3) Chemotherapeutic agent

4) PHY906+Chemotherapeutic agent

The first day of drug treatment was defined as day 1. PHY906 (500 mg/kg, bid) was administrated orally to the mice 30 min before chemotherapeutic agents at the days indicated. Chemotherapeutic agents were given either intraperitoneally or orally at the dose and schedule indicated. The tumor size, body weight, and mortality of the mice were monitored daily. Mice were sacrificed when the tumor size reached 10% of body weight.

Plasma Handling: The mouse plasma was separated from the blood by centrifugation at 10,000 g at 4° C. for 10 min.

a) Capecitabine-containing sample: The plasma (50 µl) was extracted with 200 µl of acetonitrile in the presence of 10 µl of 5-iodouracil (IU)(50 µg/ml) as an internal standard. After centrifugation, the supernatant from capecitabine-containing sample was dried by a speedvac, reconstituted with 50 µl of 0.1 M sodium acetate buffer (pH 4.8), and extracted with 1.3 ml of water-saturated ethyl acetate. The organic layer was separated after centrifugation (10,000 g at 4° C. for 10 min), dried by a speedvac and reconstituted with 100 µl of water.

b) Gemcitabine-containing plasma: The plasma (50 µl) was extracted with 200 µl of acetonitrile (ACN) in the presence of 5 µl of 0.1 mM AZT as an internal standard. After centrifugation, the supernatant was dried by a Speedvac, reconstituted with 100 µl of solution containing 2.5% ACN and 97.5% of 15 mM ammonium acetate (pH 5.0).

The resultant analyte was then analyzed by HPLC with UV absorption and/or radioactivity.

Statistical analysis and statistical power of the study (Diggle et al. Analysis of Longitudinal Data, 2nd ed. Oxford: Oxford Science Publications (1994)): A random effects model was employed to analyze data from the similar dosing animal trials. The PROC MIXED procedure in SAS was used to take into account the correlation among observations collected from the same mouse.

The following model was used to analyze the longitudinal data: $y_{ijk} = \mu + \alpha t_k + \beta(I_D t_k) + \gamma(I_P t_k) + \delta(I_D I_P t_k) + e_{ijk}$, where is the relative tumor size of the jth individual with the ith group (no treatment, drug alone, PHY906 alone, and drug+PHY906) at the kth time point, $t_k$ is the kth time point, $\alpha$ is the baseline time effect (no treatment group), $I_D$ and $I_P$ are indicator variables for having the drug treatment and the PHY906 treatment, $\beta$ is the drug-specific linear time effect, $\gamma$ is the PHY906-specifc linear time effect, $\delta$ is the drug-PHY906 synergistic linear time effect, and $e_{ijk}$ is the residual (error) term. We assumed that the errors from different individuals are independent, and errors from the same individual at different time points follow the autoregressive model, AR(1), to take into account the fact the observations from the same individual within the same treatment group are more correlated, and the responses from closer time points are more correlated within the same indivividual. The PROC MIXED in SAS 8.01 was used to perform the statistical analysis.

B. Results

Figure 21:
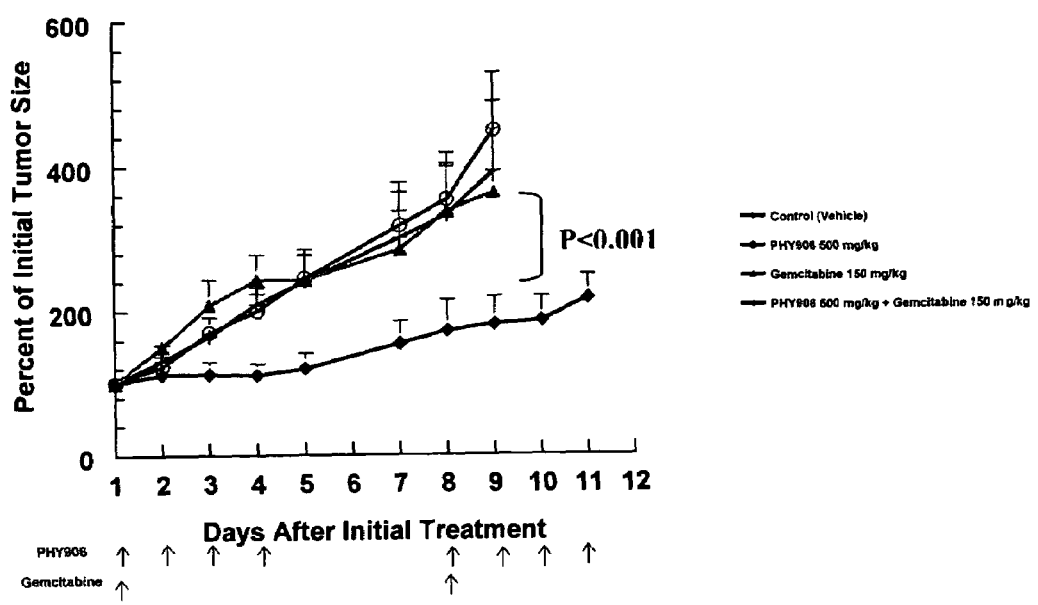
FIG. 21. Effect of PHY906 (500 mg/kg, bid, D1-4 and 8-11) on Tumor Growth in Gemcitabine (150 mg/kg, qd, D1 and 8)-Treated C57/BL6 Mouse Bearing Mouse PAN02 Tumors. Gemcitabine (150 mg/kg) was given intraperitoneally once a day on days 1 and 8. PHY906 (500 mg/kg) was given orally 30 min before gemcitabine twice a day on days 1-4 and days 8-11 (N=5 in each group).
Figure 22:
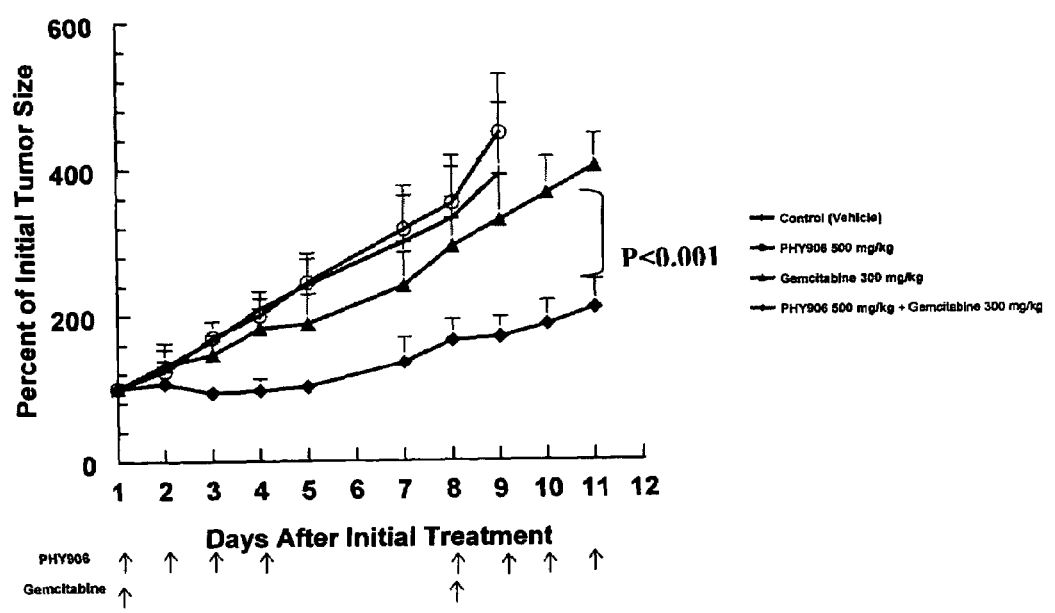
FIG. 22. Effect of PHY906 (500 mg/kg, bid, D1-4 and 8-11) on Tumor Growth in Gemcitabine (300 mg/kg, qd, D1 and 8)-Treated C57/BL6 Mouse Bearing Mouse PAN02 Tumors. Gemcitabine (300 mg/kg) was given intraperitoneally once a day on days 1 and 8. PHY906 (500 mg/kg) was given orally 30 min before gemcitabine twice a day on days 1-4 and days 8-11 (N=5 in each group).
Figure 23:
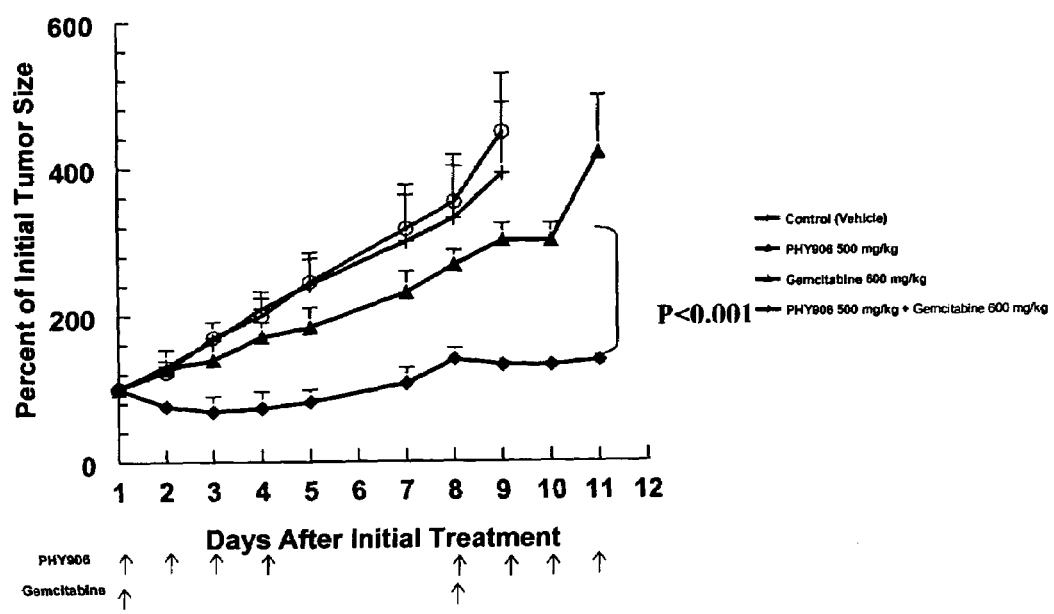
FIG. 23. Effect of PHY906 (500 mg/kg, bid, D1-4 and 8-11) on Tumor Growth in Gemcitabine (600 mg/kg, qd, D1 and 8)-Treated C57/BL6 Mouse Bearing Mouse PAN02 Tumors. Gemcitabine (600 mg/kg) was given intraperitoneally once a day on days 1 and 8. PHY906 (500 mg/kg) was given orally 30 min before gemcitabine twice a day on days 1-4 and days 8-11 (N=5 in each group).

1. Pancreatic Cancer a) Effect of PHY906 in Antitumor Activity of Different Doses of Gemcitabine in Murine PAN02 Bearing C57/BL Mice To determine the best dosing regimen in the combinational use of PHY906 and gemcitabine in order to improved antitumor activity of gemcitabine, three different doses of gemcitabine, 150, 300 and 600 mg/kg, in combination with a fixed dose of PHY906 at 500 mg/kg, were studied in C57/BL6 mice bearing PAN02 murine pancreatic carcinoma (Table 14). As shown in FIGS. 21-23, PHY906 significantly enhanced the antitumor activity of gemcitabine in PAN02 bearing mice (p<0.001 in all three doses of gemcitabine). Apparently, mice treated with gemcitabine at 600 mg/kg showed a better antitumor effect than at the lower gemcitabine doses. Gemcitabine at dose of 150 mg/kg did not have antitumor activity in this mouse model so did PHY906 alone.

TABLE 14

Summary of Treatment Conditions of PHY906 and Gemcitabine in PAN02 Murine Pancreatic Carcinoma Model.

| Experiment No. | Set | Strain of Mouse | Starting Size of Tumor (mm³) | Dose of Gemcitabine (mg/kg) (ip, D1 &8) | Batch of PHY906 | Dose of PHY906[a] (mg/kg) (po, D1-4 &8-11) |
|---|---|---|---|---|---|---|
| 1 | 2 | C57/BL6 | 300-500 | 150 | 906-6 | 500 |
| 2 | 2 | C57/BL6 | 300-500 | 300 | 906-6 | 500 |
| 3 | 2 | C57/BL6 | 300-500 | 600 | 906-6 | 500 |
| 4 | 3 | BDF-1 | 300-500 | 300 | 906-6 | 500 |
| 5 | 3 | BDF-1 | 300-500 | 600 | 906-6 | 500 |
| 6 | 3 | BDF-1 | 300-500 | 300 | 906MT | 1000[b] |

Figure 24:
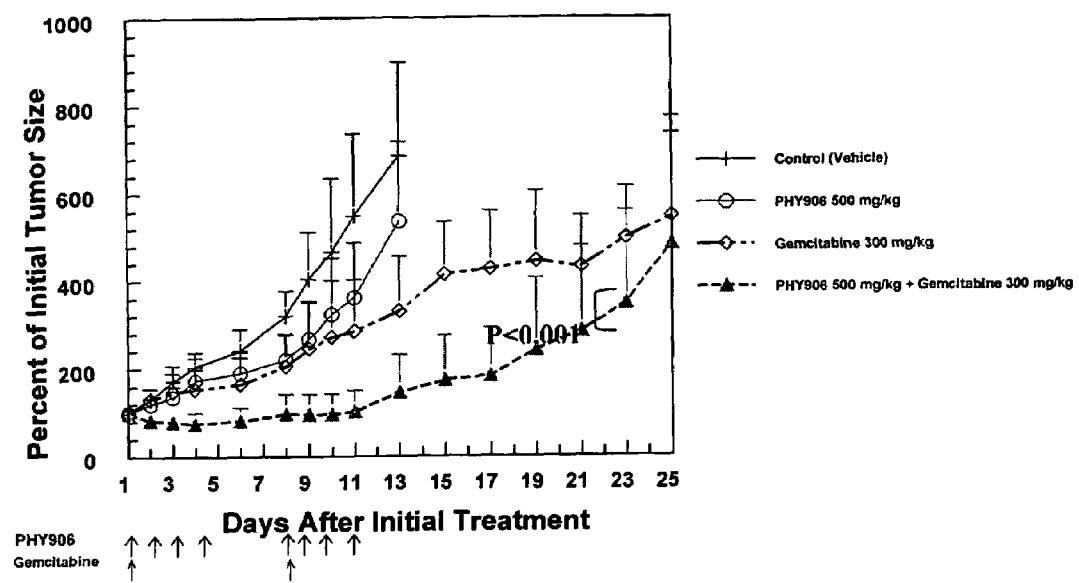
FIG. 24. Effect of PHY906 (500 mg/kg, bid, D1-4 and 8-11) on Tumor Growth in Gemcitabine (300 mg/kg, qd, D1 and 8)-Treated BDF-1 Mouse Bearing Mouse PAN02 Tumors. Gemcitabine (300 mg/kg) was given intraperitoneally once a day on days 1 and 8. PHY906 (500 mg/kg) was given orally 30 min before gemcitabine twice a day on days 1-4 and days 8-11 (N=5 in each group).
Figure 25:
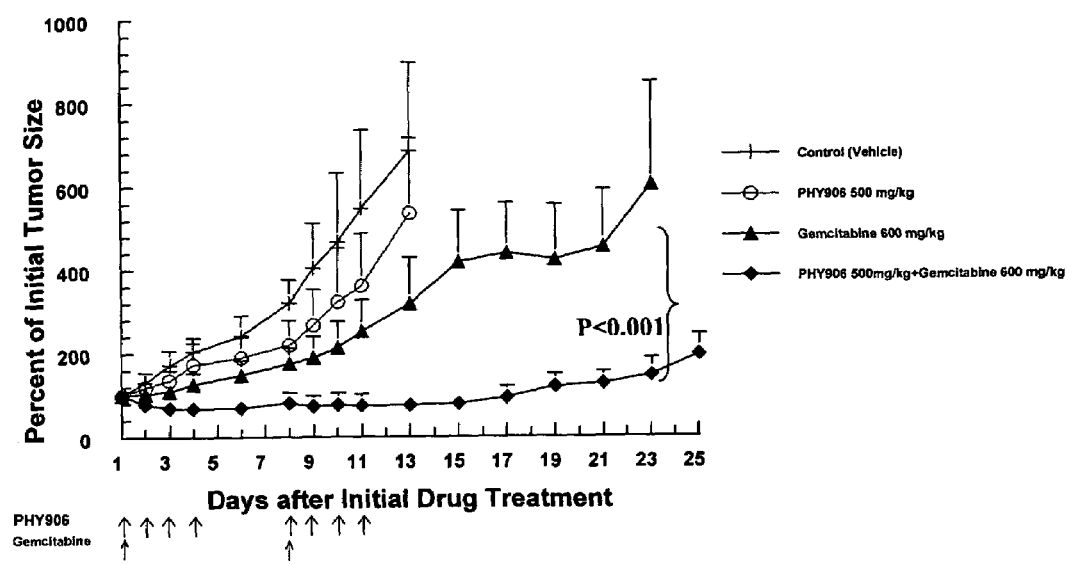
FIG. 25. Effect of PHY906 (500 mg/kg, bid, D1-4 and 8-11) on Tumor Growth in Gemcitabine (600 mg/kg, qd, D1 and 8)-Treated BDF-1 Mouse Bearing Mouse PAN02 Tumors. Gemcitabine (600 mg/kg) was given intraperitoneally once a day on days 1 and 8. PHY906 (500 mg/kg) was given orally 30 min before gemcitabine twice a day on days 1-4 and days 8-11 (N=5 in each group).
Figure 26:
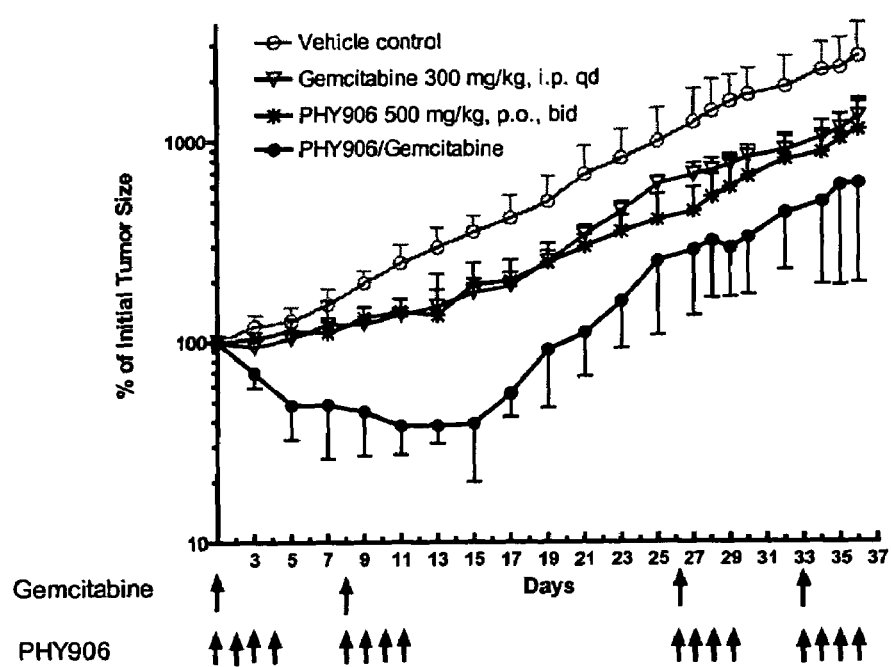
FIG. 26. Effect of PHY906 (500 mg/kg, bid, D1-4,8-11, 26-29 and 33-36) on Tumor Growth in Gemcitabine (300 mg/kg, qd, D1, 8, 26 and 33)-Treated Human PANC-1 Tumor Xenografts. Gemcitabine (300 mg/kg) was given intraperitoneally once a day on days 1, 8, 26 and 33. PHY906 (500 mg/kg) was given orally 30 min before gemcitabine twice a day on days 1-4, 8-11, 26-29 and 33-36 (N=5 in each group).
Figure 27:
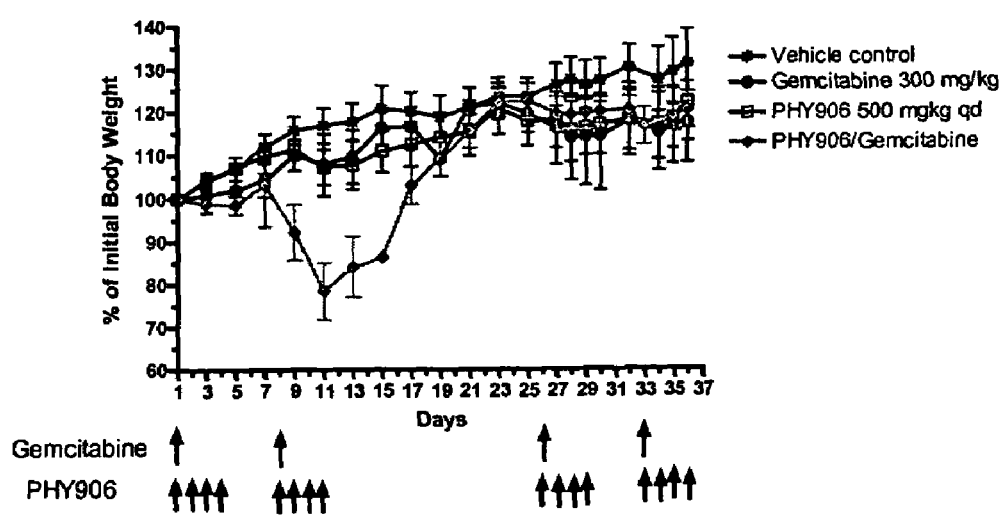
FIG. 27. Effect of PHY906 (500 mg/kg, bid, D1-4, 8-11, 26-29 and 33-36) on Bodyweight Change in Gemcitabine (300 mg/kg, qd, D1, 8, 26 and 33)-Treated Human PANC-1 Tumor Xenografts. Gemcitabine (300 mg/kg) was given intraperitoneally once a day on days 1, 8, 26 and 33. PHY906 (500 mg/kg) was given orally 30 min before gemcitabine twice a day on days 1-4, 8-11, 26-29 and 33-36 (N=5 in each group).

[a]The concentration of PHY906 was calculated based on the exact excipient amount (10%).
[b]The amount of excipient in 906MT was unknown and the concentration was calculated based on the dry weight of dry powder.

b) Effect of PHY906 in Antitumor Activity of Different Doses of Gemcitabine in Murine PAN02 Bearing BDF-1 Mice In addition to the C57/BL6 mice, PHY906 was also tested on the antitumor activity of gemcitabine in different mouse specie. PAN02 pancreas carcinoma was therefore implanted into BDF-1 mice. As shown in FIGS. 24-25, an increase of gemcitabine dosage from 300 mg/kg to 600 mg/kg significantly increased the disparity of tumor growth rates between gemcitabine alone and concomitant use of both PHY906 and gemcitabine treatments. The results indicated that the potentiation of PHY906 in antitumor activity of gemcitabine is obvious, regardless of mouse models. Additionally, a dose of gemcitabine at 600 mg/kg was selected for the subsequent animal experiments.

c) Effect of PHY906 in Antitumor Activity of Gemcitabine in Human PANC-1 Xenografts PHY906 was tested on the antitumor activity of gemcitabine in human PANC-1 bearing nude mice. As shown in FIG. 26, the combination of gemcitabine and PHY906 shrank the tumor size approximately 60% after the first cycle of drug treatment. A dosing cycle is defined as one week whereas four-day PHY906 treatment plus three-day rest. The tumor size maintained stable with 60% tumor shrinkage after the second cycle of combination drug treatment. The mice experienced up to 20% bodyweight lose upon the starting of second dosing cycle, as shown in FIG. 27. The third cycle of combination drug treatment didn't start until day 26 when the tumor sizes bounced back to the original ones at day 21.

d) Effect of Non-Clinical Batches of PHY906 on Gemcitabine in Antitumor Activity in PAN02 Bearing BDF-1 Mice Several non-clinical batches of PHY906 from different manufactures demonstrated different chemical and biological responses. The questions is whether these in vitro differences result in different in vivo responses. 906MT, which had very different chemical and biological activities from the clinical batch of PHY906, was compared with PHY906 in the antitumor activity of gemcitabine in PAN02 bearing BDF-1 mice. Since the amount of excipient in 906MT was unknown, the dose of 906MT was used at 1 g/kg*, based on the dry weight of powder. The dose of gemcitabine was 300 mg/kg bid on Days 1 and 8. The dosing schedule of 906MT was the same as for clinical batch PHY906.

Figure 28:
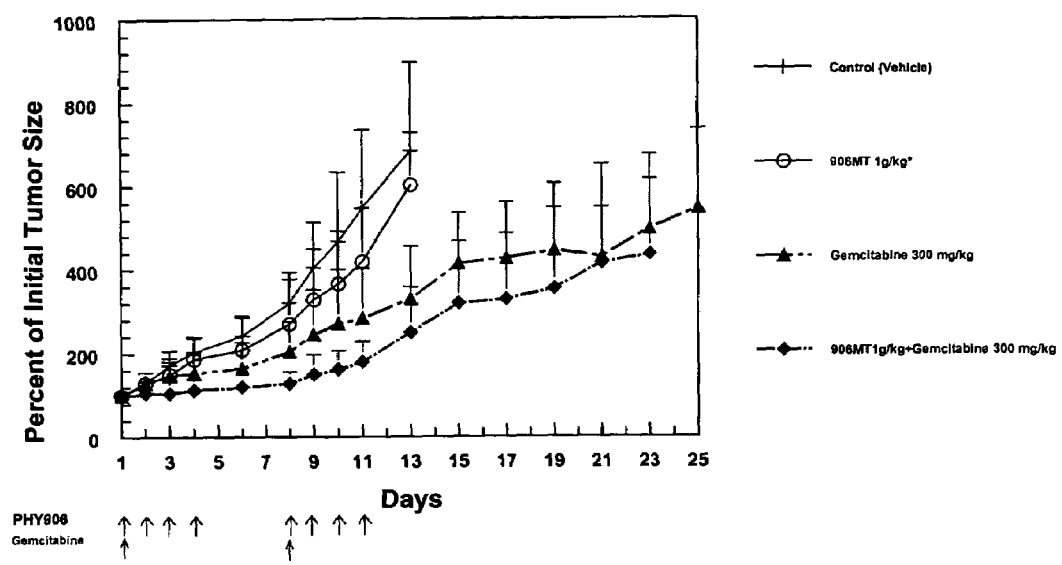
FIG. 28. Effect of 906MT (1 g/kg*, bid, D1-4 and 8-11) on Tumor Growth in Gemcitabine (300 mg/kg, qd, D1 and 8)-Treated BDF-1 Mouse Bearing Mouse PAN02 Tumors. Gemcitabine (300 mg/kg) was given intraperitoneally once a day on days 1 and 8. 906MT (1 g/kg*) was given orally 30 min before gemcitabine twice a day on days 1-4 and days 8-11 (N=5 in each group). 906MT is traditional formulation obtained in the market place. Thus the amount used (1 g/kg*) is approximate.
Figure 29:
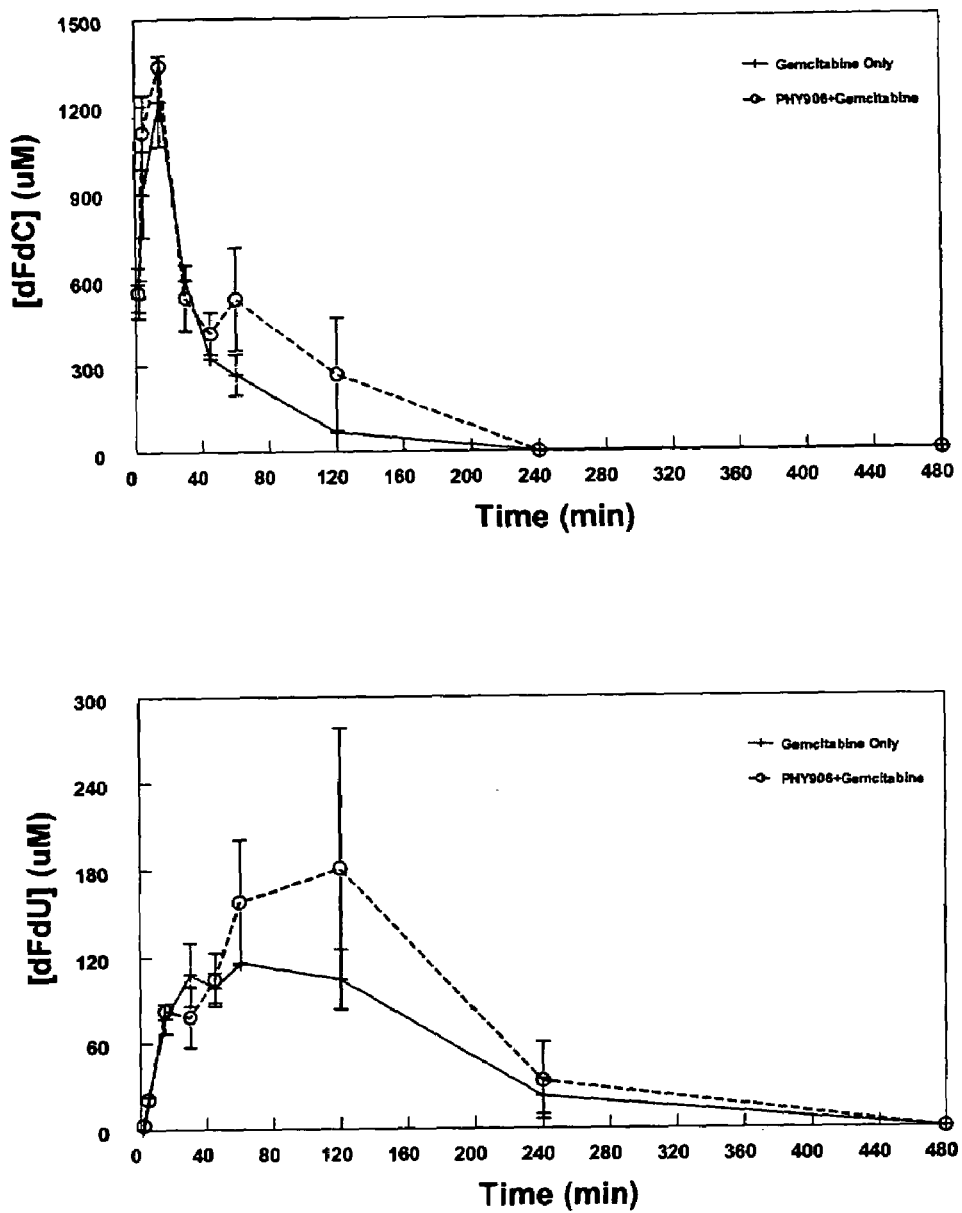
FIG. 29. Pharmacokinetics of (A) Gemcitabine (dFdC) and (B) Its Metabolite (dFdU) in Plasma. One dose of Gemcitabine (600 mg/kg) or/and PHY906 (500 mg/kg) was given orally. PHY906 was given 30 min before gemcitabine. Each mouse was bled twice at different time points, three mice at each time point.

As shown in FIG. 24, PHY906 appeared to have an effect in the antitumor activity of gemcitabine, but 906MT did not demonstrate a significant enhancement in the antitumor activity of gemcitabine, as shown in FIG. 28. These in vivo results are consistent with other in vitro pharmacological results (data not shown). The results indicated that any formulation that contains different ratios or different species of *Scutellaria, Glycyrrhiza, Ziziphus*, and *Paeonia* might not have the same therapeutic effect as PHY906 in chemotherapy.

e) Effect of PHY906 on the Pharmacokinetics of Gemcitabine (dFdC) and Its Metabolite dFdU To determine, for a future clinical trial, if PHY906 would change the metabolism of gemcitabine, a pharmacokinetics analysis in mice bearing pancreatic cancer was performed. Mice were divided into three sets of 15: gemcitabine only, gemcitabine plus PHY906, and vehicle control. Each mouse in the set was bled twice at two different time points. Plasma was processed as described in Materials and Methods and analyzed by HPLC with radioactivity confirmation of peak identity and quantitation. The studies revealed that there was not a dramatic difference in the levels of gemcitabine or its metabolite in circulation (dFdU) in the presence or absence of PHY906, as shown in FIG. 29. Computation of AUCs (area under concentration curve), $C_{max}$ (maximum drug concentration), $T_{max}$ (time of maximum drug concentration) and $T_{1/2}$ (half life) of gemcitabine and dFdU in plasma did not indicate a significant difference of gemcitabine administered alone or in combination with PHY906, as summarized in Table 15.

Previous experiments showed that the maximum tolerable dose of CPT-11 in nude mice was 200 mg/kg, which was used in this study. CPT-11 (200 mg/kg, i.p.) was given on day 0. PHY906 was given twice daily at 500 mg/kg starting on day 0 and continued for 8 days. As shown in 31, PHY906 enhanced the antitumor effect of CPT-11 on human HepG2 xenografts in nude mice. However, unlike the observation in BDF-1 mice, PHY906 showed no beneficial effect on preventing body weight loss or animal death caused by CPT-11 (data not shown). The fact that PHY906 does not protect nude mice from weight loss as it does in normal mice suggests that PHY906 may exert its effects through hematological and/or immunological systems.

b) Effect of PHY906 on the Antitumor Activity of Capecitabine on Human HepG2 Tumor-Bearing Nude Mice Capecitabine was originally developed as an orally available fluoropyrimidine analog that was capable of delivering high concentrations of the active cytotoxic agent, 5-FU, to tumor tissues. After oral administration, capecitabine is metabolized to 5-deoxy-5-fluorocytidine (5'-DFCR) by carboxylesterase in the liver, and then converted to 5'-deoxy-5-fluorouridine (5'-DFUR) by cytidine deaminase in the liver or tumor. Furthermore, 5'-DFUR is catalytically activated to 5'-fluorouracil (5-FU) by pyrimidine phosphorylase, which is

TABLE 15

Effect of PHY906 on the Pharmacokinetic Parameters of Gemcitabine (dFdC) and Its Metabolite (dFdU) in the Plasma of PAN02 Bearing BDF-1 Mice (HPLC-UV/VIS Detection Data)

| Compounds | Detection Method | AUC mg/ml · min | | Cmax mg/ml | | Tmax (min) | | T½ (min) | |
|---|---|---|---|---|---|---|---|---|---|
| | | dFdC alone | dFdC + PHY906 | dFdC alone | dFdC + PHY906 | dFdC alone | dFdC + PHY906 | dFdC alone | dFdC + PHY906 |
| dFdC | UV | 10.8 | 15.4 | 0.23 | 0.25 | 15 | 15 | 27.0 | 31.0 |
| dFdC | Radioactivity | 15.6 | 25.0 | 0.36 | 0.40 | 15 | 15 | 26.5 | 34.2 |
| dFdU | UV | 3.1 | 4.4 | 0.014 | 0.022 | 60 | 120 | 98.3 | 69.8 |
| dFdU | Radioactivity | 5.8 | 8.5 | 0.031 | 0.048 | 60 | 120 | 93.0 | 49.2 | f) Effect of PHY906 on Gemcitabine+Oxaliplatin Treated NCr-Nude Mice Bearing Human PANC-1 Tumor.

Due to the poor response of monotherapy of gemcitabine in pancreatic cancer, several combination therapies with gemcitabine have been conducted in various phases of clinical trials. Among them is the combination therapy of oxaliplatin and gemcitabine.

Figure 30:
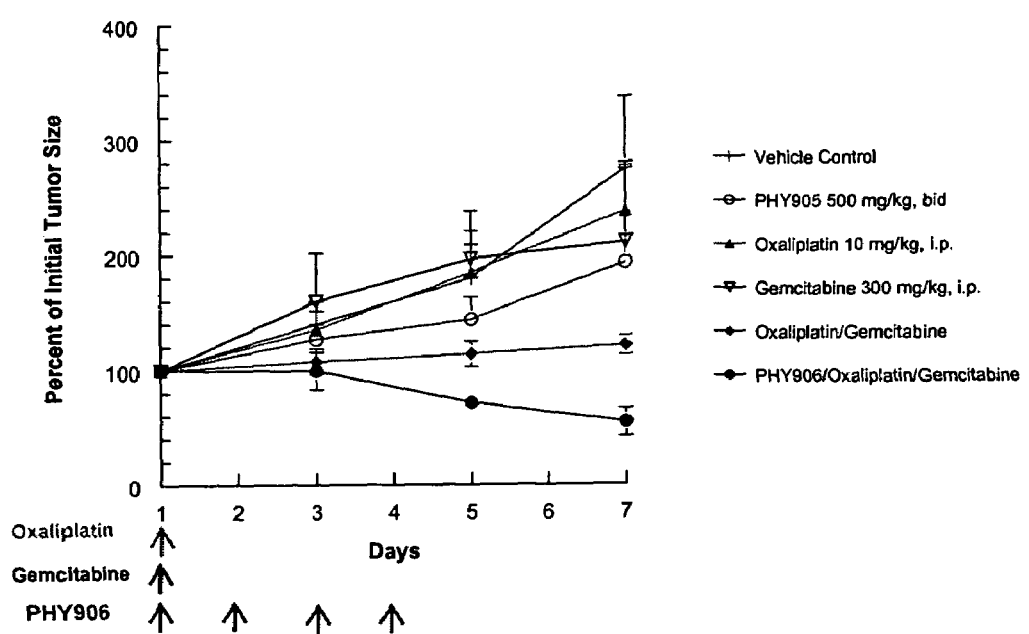
FIG. 30. Antitumor Effect of PHY906 on Gemcitabine+ Oxaliplatin Treated NCr-Nude Mice Bearing Human PANC-1 Tumor. Oxaliplatin (10 mg/kg) was given intraperitoneally 30 min prior to gemcitabine (300 mg/kg) intraperitoneally once a day on day 1. PHY906 (500 mg/kg) was given orally 30 min before oxaliplatin twice a day on days 1-4 (N=5 in each group).
Figure 31:
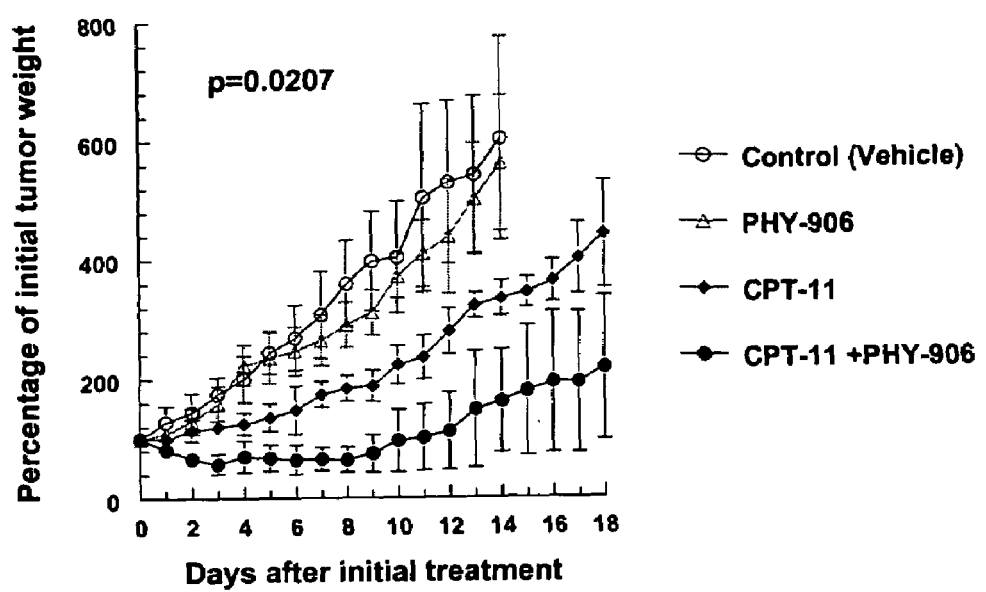
FIG. 31. Effect of PHY906 on the Tumor Growth in CPT-11 Treated NCr-Nude Mice Bearing Human HepG2 Tumor. CPT-11 (200 mg/kg) was given intraperitoneally on day 0 only. PHY906 was given orally 30 min before CPT-11 on day 0 and continued twice a day for 8 days at 500 mg/kg (N=5 in each group).

PHY906 was found not only to slow tumor progress with the combination therapy of oxaliplatin and gemcitabine, but it also reduced the tumor size to 50% at day 7 of initial drug treatment in human PANC-1 xenografts mouse model, as shown in FIG. 30.

2. Hepatocellular Carcinoma a) Effect of PHY906 on the Antitumor Activity of CPT-11 on Human HepG2 Tumor-Bearing Nude Mice Previous studies indicated that PHY906, in combination with various chemotherapeutic agents, potentiated the antitumor effects of chemotherapeutic agents in colorectal and pancreatic cancer in vivo models. Based upon the known pharmacological profiles of herbs contained in PHY906, it was speculated that the enhancing effects might act through immunological and/or hematological systems in normal mice. Therefore, experiments were designed to test the hypothesis in nude mice, which are deficient in immunological and hematological systems. Human hepatocellular carcinoma HepG2 cells were implanted into NCr-nude mice to test the effect of PHY906 on the antitumor activity of CPT-11.

rich in the tumor or liver (Berg et al., Semin. Oncol., 25: 53-59, 1998; Schwetz et al., JAMA, 286: 2085, 2001). Capecitabine was studied by Lozano et al to treat 55 patients with nonresectable hepatobiliary carcinoma; however, only a 13% response rate was observed (Aguayo et al., Seminars In Oncology, 28: 503-513, 2001; Leung et al., Seminars In Oncology, 28: 514-520, 2001; Lozano et al, Oral Capecitabine (Xeloda) for the Treatment of Hepatobillary Cancers (Hepatocellular Carcinoma, Cholangiocarcinoma, and Gallbladder Cancer). 19. 2000. Proceedings of ASCO.

Figure 32:
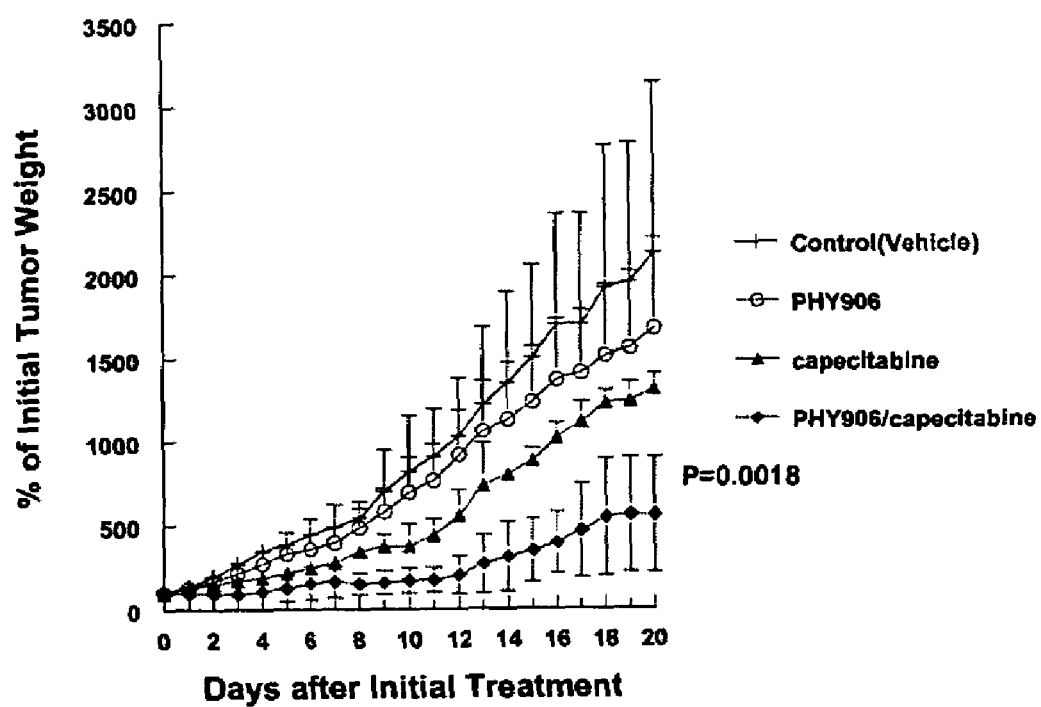
FIG. 32. Effect of PHY906 on the Tumor Growth in Capecitabine Treated NCr-Nude Mice Bearing Human HepG2 Tumor. Capecitabine (360 mg/kg) was given orally twice a day starting on day 0 for 14 consecutive days. PHY906 was given orally 30 min before capecitabine twice a day intermittently on days 0-3 and days 7-10 at 500 mg/kg (N=5 in each group).
Figure 33:
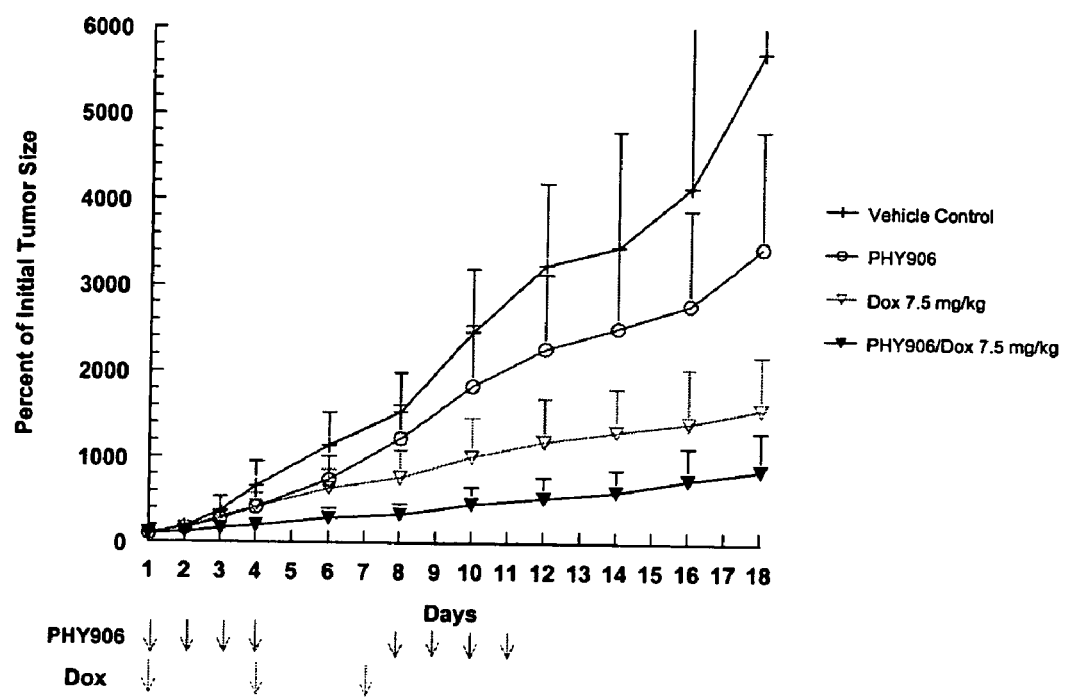
FIG. 33. Antitumor Effect of PHY906 on Doxorubicin Treated NCr-Nude Mice Bearing Human HepG2 Tumor. Doxorubicin (7.5 mg/kg) was given intraperitoneally once a day on days 1, 4 and 7. PHY906 (500 mg/kg) was given orally 30 min before doxorubicin twice a day on days 1-4 and 8-11 (N=5 in each group).
Figure 34:
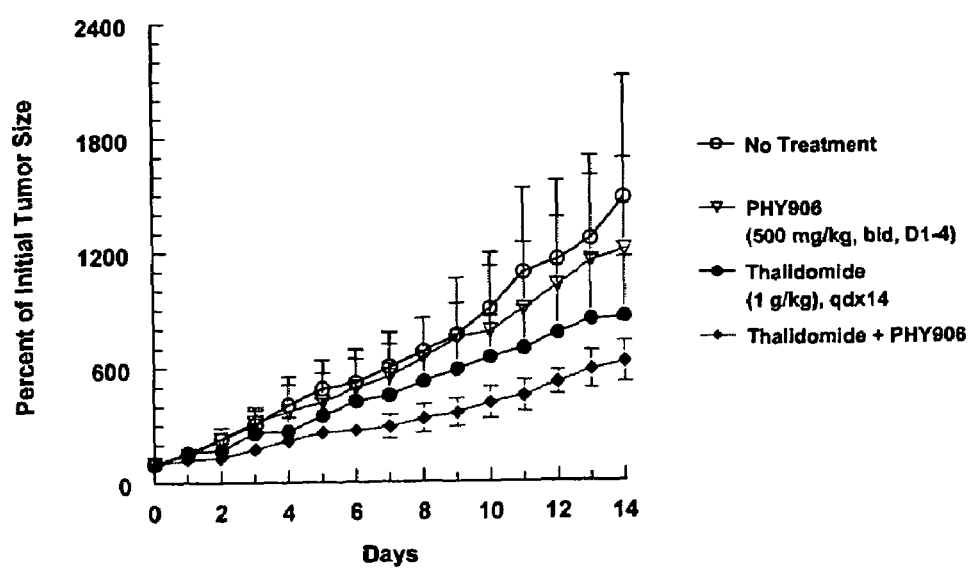
FIG. 34. Antitumor Effect of PHY906 on Thalidomide Treated NCr-Nude Mice Bearing Human HepG2 Tumor. Thalidomide (1 g/kg) was given intraperitoneally once a day continuously on days 1-14. PHY906 (500 mg/kg) was given orally 3 hours before thalidomide twice a day on days 1-4 (N=5 in each group).

Based on the enhancement in antitumor activities of 5-FU and CPT-11/5-FU/LV by PHY906 in the animal studies, an experiment was conducted to study whether PHY906 could enhance the antitumor activity of capecitabine, an oral prodrug of 5-FU. Total 20 NCr nude mice transplanted with HepG2 human hepatoma cells were divided into 4 groups (N=5 mice/group): Group (A) vehicle control; Group (B) treated with PHY906 (500 mg/kg, bid, day 0-3 and 7-10); Group (C) treated with capecitabine (360 mg/kg, bid ×14D); and Group (D) treated with PHY906 (500 mg/kg, bid, days 0-3,7-10) plus capecitabine (360 mg/kg, bid ×14D). The schedule of PHY906 used in this experiment was same as that in the previous clinical phase I/IIa trial for the alleviation of CPT-11/5-FU/LV induced cytotoxicity. PHY906 was found to enhance the antitumor activity of capecitabine, as shown in FIG. 32. A similar observation was found with lower doses of capecitabine (data not shown).

c) Effect of PHY906 on the Antitumor Activity of Doxorubicin on Human HepG2 Tumor-Bearing Nude Mice To examine whether PHY906 enhances the antitumor activity of doxorubicin, PHY906 (500 mg/kg, po, bid) was given to in conjunction with doxorubicin (7.5 mg/kg, qd, D1, 4, 7) to mice with HepG2 xenografts on days 1-4 and 8-11. As shown in FIG. 33, PHY906 showed enhancement of the antitumor activity of doxorubicin.

d) Effect of PHY906 on the Antitumor Activity of Thalidomide on Human HepG2 Tumor-Bearing Nude Mice Mice bearing human HepG2 tumor were divided into four groups: A) control group; B) PHY906 treatment group: mice were administrated with PHY906 (500 mg/kg) orally twice a day on days 1-4; C) thalidomide group: mice were administrated with thalidomide (1 g/kg) intraperitoneally once a day for 14 consecutive days; and D) PHY906 and thalidomide group: PHY906 was given 30 min before thalidomide. It was found that PHY906 enhanced the antitumor activity of thalidomide in human HepG2 xenografts mouse model, as shown in FIG. 34.

3. Colorectal Cancer

U.S. application Ser. No. 10/220,876 and PCT Application PCT/US01/07353 (which are incorporated by reference in their entirety) indicated that PHY906 enhanced the antitumor activity of CPT-11, 5-FU, CPT-11/5-FU/LV, L-OddC, VP-16 in mice bearing Colon 38 tumor. Other regimens, such as oxaliplatin and oxaliplatin/5-FU/LV, in colorectal cancer were also investigated. Oxaliplatin, a synthetic diaminocyclohexane platinum compound and a third generation drug of cisplatin, causes platinum-DNA adduct formation and destroys the integrity of the DNA. Oxaliplatin is the first platinum compound to show efficacy in colorectal cancer (Raymond et al., Annals of Oncology, 9: 1053-1071, 2004; Mathe et al., Biomedicine & Pharmacotherapy, 43: 237-250, 2004). The combination therapy of oxaliplatin/5-FU/LV has recently received FDA approval as firstline treatment in colorectal cancer patients. The response rate of oxaliplatin/5-FU/LV (~50%) is superior than that of 5-FU/LV in colorectal cancer patients.

Figure 38:
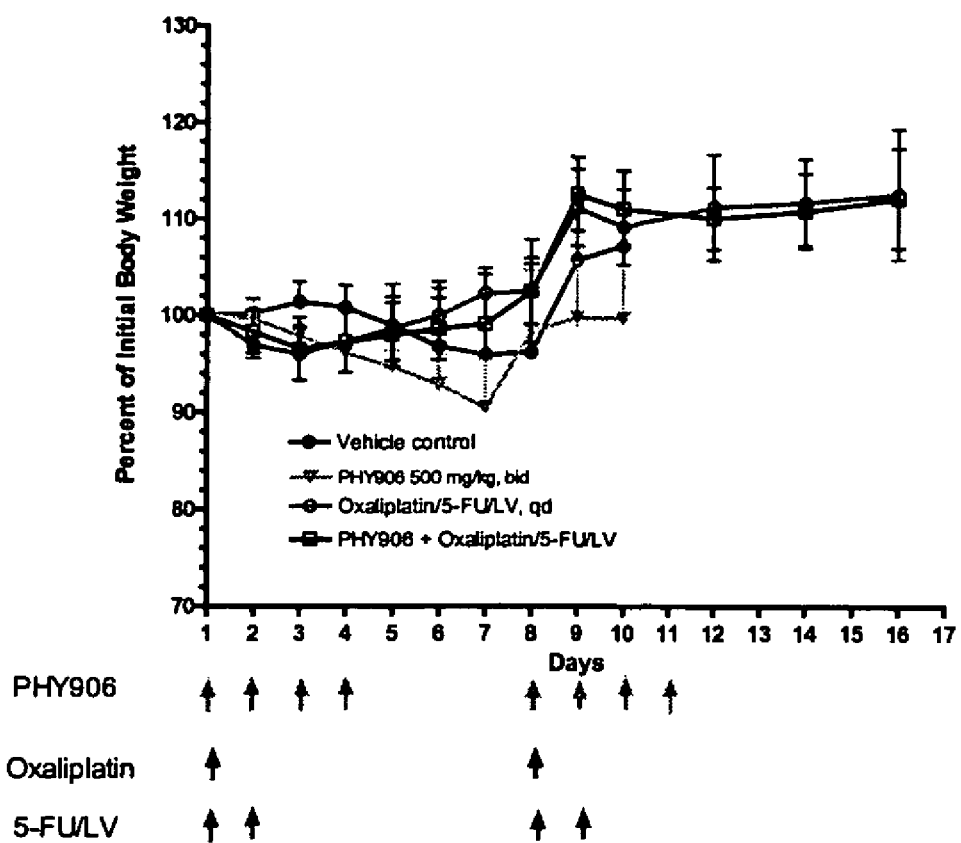
FIG. 38. Effect of PHY906 on Bodyweight of Colon 38 Bearing BDF-1 Mice Treated with Oxaliplatin, 5-FU/LV and Oxaliplatin/5-FU/LV. Oxaliplatin (5 mg/kg, D1) was given intraperitoneally on day 1. 5-FU and LV (50 mg/kg each) were given intraperitoneally on days 1, 2, 8 and 9. PHY906 was given orally 30 min before 5-FU/LV or oxaliplatin twice a day on days 1-4 and days 8-11 at 500 mg/kg (N=5 in each group).

The effect of PHY906 was examined on the antitumor activities of oxaliplatin, 5-FU/LV, and oxaliplatin/5-FU/LV in Colon 38 tumor bearing BDF-1 mice. Mice were divided into eight groups (N=5 in each group): (A) control vehicle; group (B) treated with oxaliplatin; group (C) treated with 5-FU/LV; group (D) treated with oxaliplatin/5-FU/LV; group (E) treated with PHY906; group (F) treated with PHY906 plus oxaliplatin; group (G) treated with PHY906 plus 5-FU/LV; and group (H) treated with PHY906 plus oxaliplatin plus 5-FU/LV. The results indicated that PHY906 enhanced the antitumor activities of oxaliplatin, and oxaliplatin/5-FU/LV, as shown in FIGS. 35 and 36, respectively. The dose used in the combination therapy of oxaliplatin/5-FU/LV resulted in 100% of mortality in animals. However, the data indicated that PHY906 not only reduced the mortality to 60%, but also delayed the onset of animal death caused by oxaliplatin/5-FU/LV, as shown in FIG. 37. None of animals among the drug treated groups, with exception of that treated with oxaliplatin/5-FU/LV, experienced bodyweight loss during the treatment. Due to the mortality, it could not be found out whether PHY906 had a protection against the bodyweight loss caused by oxaliplatin/5-FU/LV, as shown in FIG. 38.

C. Discussion

The effect of PHY906 was examined on the antitumor activities of oxaliplatin, 5-FU/LV, oxaliplatin/5-FU/LV, gemcitabine/oxaliplatin, doxorubicin, and thalidomide in mice. The results indicate that PHY906 enhanced the antitumor activities of oxaliplatin, oxaliplatin/5-FU/LV, gemcitabine/oxaliplatin, doxorubicin, and thalidomide as shown in FIGS. 30, 33, 34, 35, and 36. The results also indicate that PHY906 not only reduced the mortality to 60%, but also delayed the onset of animal death caused by oxaliplatin/5-FU/LV, as shown in FIG. 37.

As discussed previously, PHY906 is a traditional Chinese botanical formulation comprised of four different herbs, and it has been used for over 1800 years to treat gastrointestinal ailments, some of which are commonly observed side-effects in cancer patients undergoing chemotherapy. PHY906 was found to reduce chemotherapy-induced toxicities, including body weight loss and mortality, in addition to enhancing the antitumor efficacy of a broad-spectrum of anticancer agents, such as CPT-11, 5-FU, CPT-11/5-FU/LV, VP-16, L-OddC, and oxaliplatin in mouse colorectal cancer models.

PHY906 was co-administered with either the oral 5-FU prodrug capecitabine, doxorubicin, thalidomide or CPT-11 in human hepatocellular xenografts mouse models and with gemcitabine, oxaliplatin, gemcitabine/oxaliplatin in mouse pancreatic cancer models. The studies show that PHY906 significantly enhanced the therapeutic index of the chemotherapeutic agents. The studies also revealed that co-administration of PHY906 and CPT-11/5-FU/LV and PHY906 and capecitabine and PHY906 and gemcitabine in animal models did not alter the pharmacokinetic profile of CPT-11, 5-FU, capecitabine, gemcitabine, or their respective metabolites.

The biochemical studies revealed that the PHY906 formulation possesses a wide range of pharmacological activities. The potential mechanism(s) of action of PHY906 include (1) enhancement of cellular uptake of chemotherapeutic agents via inhibition of MDR; (2) inhibition of NF-κB activity; (3) inhibition of MMP activity; and (4) inhibition of angiogenesis.

These preclinical in vivo studies have provided rationale for developing PHY906 in the clinical setting. Currently a phase I/II open-label dose escalation clinical trial has been opened to patient enrollment to evaluate the role of PHY906 in combination with capecitabine in the treatment of hepatocellular carcinoma.

D. Summary

PHY906, a Chinese medicinal formula consisting of 4 different herbs, has been in use for some 1800 years to treat gastrointestinal (GI) ailments including diarrhea, nausea and vomiting. These side effects are quite common in patients undergoing cancer chemotherapy, thereby raising the possibility of using PHY906 to alleviate such symptoms in cancer patients and improve their quality of life. In a tumor-bearing mouse model, PHY906 significantly decreased host toxicity induced by both CPT-11-based and oxaliplatin-based chemotherapies by reducing mortality and loss in body weight. Of note, PHY906 enhanced the antitumor activity of various chemotherapeutic agents including CPT-11, CPT-11/5-FU/LV, thalidomide, capecitabine, doxorubicin, gemcitabine, oxaliplatin, and gemcitabine/oxaliplatin in colorectal, pancreatic, and liver tumor mouse models. PHY906 did not significantly change the pharmacokinetics or tissue distribution of CPT-11-, CPT-11/5-FU/LV-, or capecitabine-based or gemcitabine treatments. The mechanism of action of PHY906 is multi-factorial, including modulation of various cytokines, enhancing cell permeability and transport of active chemical(s), inhibition of MMP activity, and regulating NF-κB expression. A comprehensive panel of chemical and biological fingerprints has been developed to ensure product consistency of PHY906. This herbal preparation was studied as a potential cytotoxicity protective agent in a phase I/IIa clinical trial in colorectal cancer patients treated with CPT-11/5-FU/LV (Saltz regimen) in firstline or CPT-11 alone in secondline treatment of patients with advanced colorectal cancer. A second clinical trial is under way to determine whether PHY906 enhances the antitumor activity of capecitabine in patients with hepatocellular cancer.

It should be understood that the foregoing discussion and examples merely present a detailed description of certain preferred embodiments. It therefore should be apparent to those of ordinary skill in the art that various modifications and equivalents can be made without departing from the spirit and scope of the invention. All journal articles, other references, patents, and patent applications that are identified in this patent application are incorporated by reference in their entirety.

The foregoing detailed description has been given for clearness of understanding only and no unnecessary limitations should be understood therefrom as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES FOR WHICH A COMPLETE CITATION IS NOT PROVIDED IN THE TEXT OF THE SPECIFICATION

All references cited here are incorporated in their entirety.

Bienvenu J A, Monneret G, Gutowski M C. et al. Cytokine assays in human sera and tissues Toxicology 129: 55-61 (1998).

Bleiberg, H.: CPT-11 in Gastrointestinal Cancer. European Journal of Cancer, Vol. 35, No. 3, 371-379, 1999.

Bleiberg, H., Cvitkovic, E.: Characterization and clinical management of CPT-11 (irinotecan)-induced adverse events: The European perspective. Eur. J. Cancer 32A(Suppl 3):S18-S23, 1996.

Calabresi P. and Chabner B A: Chemotherapy of Neoplastic Diseases, Goodman & Gilman's The Pharmocological Basis of Therapeutics, Ninth Edition, Section X: 1225-1232, 1996.

Chabner B A, Allegra C J, Curt G A, Calabresi P.: Antineoplastic Agents, Goodman & Gilman's The Pharmacological Basis of Therapeutics, Ninth Edition, Chapter 51:1233-1287.

Chen J. J. W, Wu R, Yang P C, et al. Profiling expression patterns and isolating differentially expressed genes by cDNA microarray system with colorimetry detection. Genomics 51:313-324 (1998).

Chu, X-Y, Kato, Y, Ueda, K. et al. Biliary Excretion Mechanism of CPT-11 and Its Metabolites in Humans: Involvement of Primary Active Transporters. Cancer Res. 58:5137-5143, 1998.

Douillard J., Cunningham D., Roth A., Germa J., James R., Karasek P., Jandik P., Iveson T., Carmichael J., Gruia G., Dembak M., Slbaud D., Rougier P.: A randomized phase III trial comparing Irinotecan+5FU/Follnic Acid (FA) to the same schedule of 5FU/FA in patients (pts) with metastatic colorectal cancer (MCRC) as front line chemotherapy (CT), Proc. ASCO, Vol. 18, 233a, 1999.

Gilman, M. 1993. Ribonuclease protection assay. In Current Protocols in Molecular Biology, Vol. 1. (Ausubel, F. M., R. Brent, R. E. Kingston, D. D. Moore, J. G. Seidman, J. A. Smith and K. Stuhl, eds.), pp 4.7.1-4.7.8, John Wiley and Sons, Inc., New York.

Guo X, Lerner-Tung M, Chen H X, Chang C N, Zhu J L, Chang C P, Pizzorno G, Lin, TS, Cheng Y C. 5-Fluoro-2 pyrimidinone, A liver aldehyde oxidase-activated prodrug of 5-fluorouracil. Biochem Pharm, 49, 1111-1116 (1995)

Gupta E, Mick R, Ramirez J, Wang X, Lestingi T M, Vokes E E, Ratain M J: Pharmacokinetic and pharmacodynamic evaluation of the topoisomerase inhibitor irinotecan in cancer patients. J Clin Oncol 15:1502-1510, 1997.

Haaz M. C., Rivory, L., Riche, C., et al. Metabolism of irinotecan (CPT-11) by human hepatic microsomes: participation of cytochrome P-450 3A and drug interactions. Cancer Res 58:468-472 (1998).

Hani Oka Hiroshi, Taki No Ko Suke: Application of 212 formula of Kampo Medicine. Kabusiki Kaishya, Tokyo, Japan, 1998.

Hsu H. and Hsu C., Commonly used Chinese herbal formulas; Companion Handbook, Ohai Press.

Joulia, J., Pinguet, F., Ychou, M., Duffour, J., Astre, C. and Bressolle, F.: Plasma and Salivary Pharmacokinetics of 5-Fluorouracil (FU) in Patients with Metastatic Colorectal Cancer Receiving FU Bolus Plus Continuous Infusion with High-dose Folinic Acid. European Journal of Cancer, Vol. 35, No. 2, 26-301, 1999.

Kaneda N., Nagata H., Furuta T., Yokokura T.: Metabolism and pharmacokinetics of the camptothecin analogue CPT-11 in the mouse. Cancer Res 50:1715-1720, 1990.

Kivisto K. T., Kroemer H. K. and Eichelbaum M. The role of human cytochrome P450 enzymes in the metabolism of anticancer agents: implications for drug interactions. Br J. Clin Pharmacol 40:523-530 (1995).

Koima K., et. al. Long-term administration of Asho-saiko-to@increase cytochrome P-450 mRNA level in mouse liver. Biol. Pharm. Bull. 21:426-428, 1998.

Lombardi V. R. M, Garcia M and Cacabelos L. R. R. Characterization of cytokine production, screening of lymphocyte subset patterns and in vitro apoptosis in healthy and Alzheimer's Disease (AD) individuals. Journal of Neuroimmunol 97:163-171(1999).

Miller C L and Eaves C J. Expansion in vitro of adult murine hematopoietic stem cells with transplantable lympho-myeloid reconstituting ability. Proc. Natl. Acad. Sci. 94:13648-13653 (1997).

Mori K., Hirose T., Machida S., Tominaga K.: Kampo medicines for the prevention of irinotecan-induced diarrhea in advanced non-small cell lung cancer. Gan To Kagaku Ryoho 25:1159-63, 1998.

Marita M., Nagai E., Hagiwara H., Aburada M., Yokoi T., Kamataki T.: Inhibition of beta-glucuronidase by natural glucuronides of kampo medicines using glucuronide of SN-38 (7-ethyl-10-hydroxycamptothecin) as a substrate. Xenobiotica 23:5-10, 1993.

Peters, G. and van Groeninger, C.: Clinical relevance of biochemical modulation of 5-fluorouracil. Annals of Oncology 2: 469-480, 1991.

Pinedo, H. and Peters, G. Fluorouracil: Biochemistry and Pharmacology. Journal of Clinical Oncology, Vol. 6, No. 10 (October), 1633-1664, 1988.

Pizzorno G., Wiegand R., Lentz S. and Handschumacher R., Brequinar Potentiates 5-Fluorouracil antitumor activity in a Murine model colon 38 tumor by tissue-specific modulation of uridine nucleotide pools. Cancer Res., 52: 1660-1665, 1992

Roby C. A., Anderson G D and Dryer D A et al. St John's Wort: Effect on CYP3A4 activity. Clin. Pharmacol. Ther. 67, 451-457 (2000).

Saliba F, Hagipantelli R, Misset J-L, Bastian G, vassal G, Bonnay M, Herait P, Cote C, Mahjoubi M, Mignard D, Cvitkovic E: Pathophysiology and therapy in irinotecan-induced delayed-onset diarrhea in patients with advanced colorectal cancer: A prospective assessment. J Clin Oncol 16:2745-2751, 1998.

Saltz L B, Locker P K, Plrotta N, Elfring G L, Miller L L: Weekly Irinotecan (CPT-11), Leucovorin (LV), and Fluorouracil (FU) is superior to daily x5 LV/FU in patients (PTS) with previously untreated metastatic colorectal cancer (CRC), Proc. ASCO, Vol. 18, 233a, 1999.

Stucky-Marshall, L.: New Agents in Gastrointestinal Malignancies: Part 1: Irinotecan in Clinical Practice, Cancer Nursing, 22(3): 212-219, 1999.

Takasuna K, Takehiro H, Hirohashi M, Kato M, et al. Involvement of b-glucuronidase in intestinal microflora in the intestinal toxicity of the antitumor camptothecin derivative irinotecan hydrochloride (CPT-11) in rats. Cancer Res. 56:3752-3757 (1996).

Takasuna K, Takehiro H, Hirohashi M, et al. Inhibition of intestinal microflora □-glucuronidase modifies the distribution of the active metabolite of the antitumor agent, irinotecan hydrochloride (CPT-11) in rats. Cancer Chemother Pharmacol. 42:280-286 (1998).

Wasserman E., Myara A., Lokiec F., Goldwasser F., Trivin F., Mahjoubi M., Misset J., Cvitkovic E.: Severe CPT-11 toxicity in patients with Gilbert's syndrome: Two case reports. Ann Oncol 8:1049-1051, 1997.

Wierda D. and Matamoros M. Partial characterization of bone marrow hemopoiesis in mice after cisplatin administration. Toxicol & Applied Pharmacol 75:25-34(1984).

Xu Guo-Jun, Introduction to the Chinese Materia Medica, China Pharmaceutical Science Publication Inc., Beijin, China, 1996, p. 398.

The invention claimed is:

1. A composition comprising:
   i) a pharmaceutically acceptable carrier;
   ii) an herbal preparation consisting essentially of *Scutellaria, Glycyrrhiza, Ziziphus* and *Paeonia*; and
   iii) a chemotherapeutic formulation comprising one or more chemotherapeutic compounds selected from the group consisting of doxorubicin, thalidomide, capecitabine, gemcitabine, and oxaliplatin.

2. A composition of claim 1, wherein the chemotherapeutic formulation further comprises 5-fluorouracil (5FU) and leucovorin (LV).

3. The composition of claim 1, wherein the herbal preparation consists of *Scutellaria baicalensis, Glycyrrhiza uralensis, Ziziphus jujuba,* and *Paeonia lactiflora*.

4. A method of relieving side effects of a chemotherapeutic compound in a mammal comprising administering a composition comprising: i) a pharmaceutically acceptable carrier; ii) an herbal preparation consisting essentially of *Scutellaria baicalensis, Glycyrrhiza uralensis, Ziziphus jujuba* and *Paeonia lactiflora*; and iii) a chemotherapeutic formulation comprising the chemotherapeutic compound selected from the group consisting of doxorubicin, thalidomide, capecitabine, gemcitabine, and oxaliplatin.

\* \* \* \* \*